United States Patent
Towler et al.

(10) Patent No.: US 10,815,144 B2
(45) Date of Patent: Oct. 27, 2020

(54) GLASSES, CEMENTS AND USES THEREOF

(71) Applicants: Mark Robert Towler, Toronto (CA);
Adel Moh'd Fawzi A. R. Alhalawani, Toronto (CA)

(72) Inventors: Mark Robert Towler, Toronto (CA);
Adel Moh'd Fawzi A. R. Alhalawani, Toronto (CA)

( * ) Notice: Subject to any disclaimer, the term of this patent is extended or adjusted under 35 U.S.C. 154(b) by 100 days.

(21) Appl. No.: 16/318,064

(22) PCT Filed: Jul. 14, 2017

(86) PCT No.: PCT/CA2017/050854
§ 371 (c)(1),
(2) Date: Jan. 15, 2019

(87) PCT Pub. No.: WO2018/014120
PCT Pub. Date: Jan. 25, 2018

(65) Prior Publication Data
US 2019/0233322 A1     Aug. 1, 2019

Related U.S. Application Data

(60) Provisional application No. 62/364,479, filed on Jul. 20, 2016.

(51) Int. Cl.
*C03C 3/062* (2006.01)
*A61L 24/12* (2006.01)
(Continued)

(52) U.S. Cl.
CPC .............. *C03C 3/062* (2013.01); *A61K 6/864* (2020.01); *A61K 6/889* (2020.01); *A61L 24/12* (2013.01);
(Continued)

(58) Field of Classification Search
CPC ...................................................... C03C 3/097
See application file for complete search history.

(56) References Cited

U.S. PATENT DOCUMENTS

| | | | |
|---|---|---|---|
| 7,981,972 B2 | 7/2011 | Towler et al. | |
| 9,352,069 B2 | 5/2016 | Dickinson et al. | |

(Continued)

FOREIGN PATENT DOCUMENTS

| | | |
|---|---|---|
| CA | 2872430 A1 | 11/2013 |
| WO | 2007020613 A1 | 2/2007 |

(Continued)

OTHER PUBLICATIONS

N.Y. Mikhailenko et al., "Solubility of calcium phosphate glasses and glass ceramic materials in water and physiological media" Glas. Ceram. 2013, 70:3-4, 158-163.

(Continued)

*Primary Examiner* — Michael F Pepitone
(74) *Attorney, Agent, or Firm* — Bereskin & Parr LLP/S.E.N.C.R.L., s.r.l.; Michael Fenwick

(57) ABSTRACT

Various embodiments of tantalum- and/or niobium-containing glasses and cements as well as uses thereof are described herein. For example, in an embodiment, the glasses comprise a transition metal pentoxide such as tantalum pentoxide and/or niobium pentoxide present in the glass in an amount of less than 2.0 mol %, based on the total composition of the glass, glass polyalkenoate cements prepared from such glasses and uses of such cements, for example, for sternal closure or fixation, stabilization and/or repair of a fracture in a bone in the wrist, elbow, knee, shoulder, spine and/or hip.

19 Claims, 40 Drawing Sheets

(51) Int. Cl.
- *C03C 4/00* (2006.01)
- *A61K 6/864* (2020.01)
- *A61K 6/889* (2020.01)
- *C03C 3/078* (2006.01)
- *C03C 3/097* (2006.01)
- *C08L 33/08* (2006.01)

(52) U.S. Cl.
CPC .............. *C03C 3/078* (2013.01); *C03C 3/097* (2013.01); *C03C 4/0021* (2013.01); *A61L 2430/02* (2013.01); *C03C 2204/00* (2013.01); *C03C 2205/06* (2013.01); *C08L 33/08* (2013.01)

(56) References Cited

U.S. PATENT DOCUMENTS

| | | |
|---|---|---|
| 2008/0182920 A1 | 7/2008 | Towler et al. |
| 2008/0208340 A1 | 8/2008 | Boyd et al. |
| 2011/0123832 A1 | 5/2011 | Matsumoto et al. |
| 2013/0209963 A1* | 8/2013 | Schweiger ........... A61C 13/083 433/215 |
| 2016/0083631 A1* | 3/2016 | Jia ........................ C08L 33/08 525/303 |
| 2016/0235884 A1 | 8/2016 | Dickinson et al. |

FOREIGN PATENT DOCUMENTS

| | | |
|---|---|---|
| WO | 2008104964 A2 | 9/2008 |
| WO | 2011121087 A1 | 10/2011 |
| WO | 2013164696 A1 | 11/2013 |

OTHER PUBLICATIONS

T. Miyazaki et al., "Mechanism of bonelike apatite formation on bioactive tantalum metal in a simulated body fluid" Biomaterials 2002, 23:3, 827-832.

G. Mohandas et al., "Porous tantalum and tantalum oxide nanoparticles for regenerative medicine" Acta Neurobiol. Exp. (Wars). 2014, 74, 188-196.

N. Moritz et al., "Characterisation of bioactive glass coatings on titanium substrates produced using a CO2 laser" J. Mater. Sci. Mater. Med. 2004, 15:7, 787-794.

M. Navarro et al., "Biomaterials in orthopaedics," J. R. Soc. Interface 2008, 5, 1137-1158.

J.W. Nicholson, "Adhesive dental materials—a review" Int. J. Adhes. Adhes. 1998, 18:4, 229-236.

J.W. Nicholson, "Chemistry of glass-ionomer cements: a review" Biomaterials 1998, 19:6, 485-494.

C. Persson et al., "Radiopacity of tantalum-loaded acrylic bone cement" Proc. Inst. Mech. Eng. H. 2006, 220:7, 787-791.

G.M. de Pietro et al., "Thermal, structural, and crystallization properties of new tantalum alkali-germanate glasses" J. Am. Ceram. Soc. 2015, 98:7, 2086-2093.

D. Ring and J.B. Jupiter, "Treatment of osteoporotic distal radius fractures" Osteoporos. Int. 2005, 16 Supple 2, S80-S84.

M. Roy et al., "Comparison of tantalum and hydroxyapatite coatings on titanium for applications in load bearing implants" Adv. Eng. Mater. 2010, 12:11 B637-B641.

K.B. Sagomonyants et al., "Porous tantalum stimulates the proliferation and osteogenesis of osteoblasts from elderly female patients" J. Orthop. Res. 2011, 29:4, 609-616.

H. Sakano et al., "Treatment of the unstable radius fracture with external fixation and a hydroxyapatite spacer" J. Hand Surg. 2001, 26:5, 923-930.

J.L. Orbay and D.L. Fernandez, "Volar fixed-angle plate fixation for unstable distal radius fractures in the elderly patient" J. Hand Surg. Am. 2004, 29:1, 96-102.

R.B. Saper and R. Rash, "Zinc: an essential micronutrient" Am. Fam. Physician 2009, 79:9, 768-772.

C. Schimmer et al., "Gentamicin-collagen sponge reduces sternal wound complications after heart surgery: a controlled, prospectively randomized, double-blind study" J. Thorac. Cardiovasc. Surg. 2012, 143:1, 194-200.

C. Schimmer et al., "Prevention of sternal dehiscence and infection in high-risk patients: a prospective randomized multicenter trial" Ann. Thorac. Surg. 2008, 86:6, 1897-904.

D.C. Smith, "Development of glass-ionomer cement systems" Biomaterials 1998, 19:6, 467-478.

A. Stamboulis et al., "Characterisation of commercial ionomer glasses using magic angle nuclear magnetic resonance (MAS-NMR)" Biomaterials 2004, 25, 3907-3913.

S.-P. Szu wt al., "Effect of precursors on the structure of phosphosilicate gels: 29Si and 31P MAS-NMR study" J. Non. Cryst. Solids. 1992, 143, 21-30.

S.K. Tomlinson et al., "Investigation of the dual setting mechanism of a novel dental cement using infrared spectroscopy" Vib. Spectrosc. 2007, 45:1, 10-17.

M.R. Towler et al., "Zinc ion release from novel hard tissue biomaterials," Biomed. Mater. Eng. 2004, 14:4, 565-572.

E.A. Wasson and J.W. Nicholson, "New aspects of the setting of glass-ionomer cements" J. Dent. Res. 1993, 72:2, 481-483.

E.A. Wasson and J.W. Nicholson, "Studies on the setting chemistry of glass-ionomer cements" Clin. Mater. 1991, 7:4, 289-293.

J.A. Williams et al., "The effect of the disc support system on biaxial tensile strength of a glass ionomer cement" Dent. Mater. 2002, 18:5, 376-379.

A.W. Wren et al., "Comparison of a SiO2—CaO—ZnO—SrO glass polyalkenoate cement to commercial dental materials: ion release, biocompatibility and antibacterial properties" J. Mater. Sci. Mater. Med. 2013, 24:9, 2255-2264.

W. Wren et al., "Gallium containing glass polyalkenoate anti-cancerous bone cements: Glass characterization and physical properties" J. Mater. Sci. Mater. Med. 2012, 23:8, 1823-1833.

A.W. Wren et al., "A spectroscopic investigation into the setting and mechanical properties of titanium containing glass polyalkenoate cements" J. Mater. Sci. Mater. Med. 2010, 21:8, 2355-2364.

A.D. Wilson and B.E. Kent, "The glass-ionomer cement, a new translucent dental filling material" Appl. Chem. Biotechnol. 1971, 21, 313.

N. Zainuddin et al., "A long-term study on the setting reaction of glass ionomer cements by (27)AI MAS-NMR spectroscopy" Dent. Mater. 2009, 25:3, 290-5.

A.M.F. Alhalawani, "A glass polyalkenoate cement carrier for bone morphogenetic proteins" J. Mater. Sci. Mater. Med. 2015, 26, 151.

A.M.F. Alhalawani et al., "A novel glass polyalkenoate cement for fixation and stabilisation of the ribcage, post sternotomy surgery: An ex-vivo study," J. Funct. Biomater. 2013, 4, 329-357.

A.M.F. Alhalawani et al., "The role of poly(acrylic acid) in conventional glass polyalkenoate cements" J. Polym. Eng. 2016 36:3, 221-237.

A.M.F. Alhalawani et al., "Influence of gallium on the surface properties of zinc based glass polyalkenoate cements" Mater. Chem. Phys. 2014, 147:3 360-364.

A.M.F. Alhalawani and M.R. Towler, "A novel tantalum-containing bioglass. Part I. Structure and solubility" Materials Science and Engineering C 2017, 72, 202-211.

A.M.F. Alhalawani et al., "A novel tantalum-containing bioglass. Part II. Development of a bioadhesive for sternal fixation and repair" Materials Science and Engineering C 2017, 71, 401-411.

A.M.F. Alhalawani and M.R. Towler, "A review of sternal closure techniques" J. Biomater. Appl. 2013, 28:4 483-97.

A.M.F. Alhalawani and M.R. Towler, "The effect of ZnO↔Ta2O5 substitution on the structural and thermal properties of SiO2—ZnO—SrO—CaO—P2O5 glasses" Mater. Charact. 2016, 114, 218-224.

A.O. Akinmade and J.W. Nicholson, "Glass-ionomer cements as adhesives," J. Mater. Sci. Mater. Med. 1993, 4:2 95-101.

V.K. Balla et al., "Porous tantalum structures for bone implants: Fabrication, mechanical and in vitro biological properties" Acta Biomater. 2010, 6:8 3349-59.

V.K. Balla et al., "Tantalum—a bioactive metal for implants" JOM 2010, 62:7, 61-64.

(56) References Cited

OTHER PUBLICATIONS

J. Black, "Biologic performance of tantalum" Clin. Mater. 1994, 16:3 167-173.
D. Boyd et al., "Zinc-based glass polyalkenoate cements with improved setting times and mechanical properties" Acta Biomater. 2008, 4:2, 425-431.
D. Boyd et al., "TEM analysis of apatite surface layers observed on zinc based glass polyalkenoate cements" J. Mater. Sci. 2008, 43:3, 1170-1173.
D. Boyd et al., "The role of Sr2+ on the structure and reactivity of SrO—CaO—ZnO—SiO2 ionomer glasses" J. Mater. Sci. Mater. Med. 2008, 19, 953-957.
D.S. Brauer et al., "Solubility of glasses in the system P2O5—CaO—MgO—Na2O—TiO2: Experimental and modeling using artificial neural networks" J. Non. Cryst. Solids. 2007, 353:3, 263-270.
G. Calas et al., "Structure-property relationships in multicomponent oxide glasses" Comptes Rendus Chim. 2002, 5:12, 831-843.
Y.-Y. Chang, et al., "Antibacterial properties and cytocompatibility of tantalum oxide coatings" Surf. Coatings Technol. 2014, 259, Part B, 193-198.
O.M. Clarkin et al., "Comparison of an experimental bone cement with a commercial control, Hydroset(TM)" J. Mater. Sci. Mater. Med. 2009, 20:7, 1563-1570.
D.J. Cohen and L.V. Griffin, "A biomechanical comparison of three sternotomy closure techniques" Ann. Thorac. Surg. 2002, 73:2, 563-568.
A. Coughlan et al., "Zinc and silver glass polyalkenoate cements: An evaluation of their antibacterial nature" Biomed. Mater. Eng. 2010, 20, 99-106.
M. Darling and R. Hill, "Novel polyalkenoate (glass-ionomer) dental cements based on zinc silicate glasses" Biomaterials 1994, 15:4, 299-306.
H. Darwish et al., "Electrical and physical properties of Na2O—CaO—MgO—SiO2 glass doped with NdF3" J. Mater. Sci. Mater. Electron. 2013, 24, 1028-1036.
S.A. Earnshaw et al., "Closed reduction of Colles fractures: Comparison of manual manipulation and finger-trap traction" J. Bone & Jt. Surg. 2002, 84, 354-358.
T.M. Eidem et al., "Drug-eluting cements for hard tissue repair: A comparative study using vancomycin and RNPA1000 to inhibit growth of *Staphylococcus aureus*" J. Biomater. Appl. 2014, 28:8, 1235-1246.
M. Eigen, "Chapter 12—Oxide Glasses" in Structural Chemistry of Glasses, Elsevier Science Ltd., Oxford, 2002, 463-511.
P.W.M. Fedak and A. Kasatkin, "Enhancing sternal closure using Kryptonite bone adhesive: Technical report" Surg. Innov. 2011, 18:4 NP8-11.
P.W. Fedak et al., "Kryptonite bone cement prevents pathologic sternal displacement," Ann Thorac Surg 2010, 90:3, 979-985.
F. Fitoussi et al., "Treatment of displaced intra-articular fractures of the distal end of the radius with plates" J. Bone Jt. Surg. 1997, 79:9, 1303-12.
M. Ford et al., "Design of a screw-plate system to minimize loosening in sternal fixation", Bioeng. Conf. (NEBEC), 2011 IEEE 37th Annu. Northeast, 1-2 (2011).

O. Friberg et al., "Influence of more than six sternal fixation wires on the incidence of deep sternal wound infection" Thorac. Cardiovasc. Surg. 2006, 54:7, 468-473.
L. Grech et al., "Investigation of the physical properties of tricalcium silicate cement-based root-end filling materials" Dent. Mater. 2013, 29:2, e20-8.
D.P. Green, "Pins and plaster treatment of comminuted fractures of the distal end of the radius" J. Bone & Jt. Surg. 1975, 57, 304-310.
M.R. Guida et al., "Preliminary work on the antibacterial effect of strontium in glass ionomer cements" J. Mater. Sci. Lett. 2003, 22, 1401-1403.
N. Hidaka et al., "Calcium phosphate bone cement for treatment of distal radius fractures: A preliminary report" J Orthop Sci. 2002, 7:2, 182-7.
M. Holland et al., "Sternal closure with kryptonite—an innovative approach to a lingering pain in the chest" Can J Cardiol 2010, 26, Suppl D, 155 N031.
A. Hoppe et al., "A review of the biological response to ionic dissolution products from bioactive glasses and glass-ceramics" Biomaterials 2011, 32:11, 2757-2774.
M.G. Jakubietz et al., "The use of beta-tricalcium phosphate bone graft substitute in dorsally plated, comminuted distal radius fractures" J. Orthop. Surg. Res. 2011, 6:24.
S. Jolly wt al., "Cabled butterfly closure: a novel technique for sternal closure" Ann. Thorac. Surg. 2012, 94:4, 1359-1361.
J.R. Jones, "Review of bioactive glass: from Hench to hybrids" Acta Biomater. 2013, 9:1, 4457-86.
H. Kapoor et al., "Displaced intra-articular fractures of distal radius: a comparative evaluation of results following closed reduction, external fixation and open reduction with internal fixation" Injury 2000, 31:2, 75-9.
B.A. Khader and M.R. Towler, "Common treatments and procedures used for fractures of the distal radius and scaphoid: A review" Mater Sci Eng C Mater Biol Appl. 2017, 74, 422-433.
T. Kosuge et al., "Thermal stability and heat capacity changes at the glass transition in K2O—WO3—TeO2 glasses" J. Non. Cryst. Solids 1998, 242:2-3, 154-164.
G. Lewis et al., "Evaluation of two novel aluminum-free, zinc-based glass polyalkenoate cements as alternatives to PMMA bone cement for use in vertebroplasty and balloon kyphoplasty" J. Mater. Sci. Mater. Med. 2010, 21:1, 59-66.
L.F. López Almodóvar et al., "Transverse plate fixation of sternum: a new sternal-sparing technique" Ann. Thorac. Surg. 2008, 86:3, 1016-1017.
P.J. Marie et al., "Mechanisms of action and therapeutic potential of strontium in bone" Calcif. Tissue Int. 2001, 69:3, 121-129.
S. Matsuya et al., "IR and NMR analyses of hardening and maturation of glass-ionomer cement" J. Dent. Res. 1996, 75:12, 1920-1927.
S. Matsuya et al., "Structure of bioactive glass and its application to glass ionomer cement" Dent. Mater. J. 1999, 18:2, 155-166.
M.N. Mavros et al., "Gentamicin collagen sponges for the prevention of sternal wound infection: a meta-analysis of randomized controlled trials" J. Thorac. Cardiovasc. Surg. 2012, 144:5, 1235-1240.
J.F. McCabe et al., "An investigation of test-house variability in the mechanical testing of dental materials" J. Dent. 1990, 18:2, 90-97.

\* cited by examiner

GLASSES, CEMENTS AND USES THEREOF

CROSS-REFERENCE TO RELATED APPLICATIONS

This application is a National Stage of co-pending International Application No. PCT/CA2017/050854 filed Jul. 14, 2017, which claims the benefit of priority to U.S. provisional application No. 62/364,479 filed on Jul. 20, 2016, the contents of both of which are incorporated herein by reference in their entirety.

FIELD

The present disclosure relates to tantalum- and/or niobium-containing glasses and cements as well as uses of such cements, for example, in sternal closure or for fixation, stabilization and/or repair of a fracture in a bone in the wrist, elbow, knee, shoulder, spine and/or hip.

BACKGROUND

Bioactive glasses are candidate materials for a wide variety of biomedical applications as they can bond to bone and be formulated to release bioactive ions into the local environment, resulting in antimicrobial activity and enhanced cell response [1, 2].

Silicate-glasses are inorganic amorphous solids composed of $SiO_4^{3-}$ tetrahedral units. In other words, silicon is coordinated to 4 oxygen atoms and each oxygen atom is coordinated to 2 silicon units so that the structure is a three-dimensional (3-D) network of corner connected $[SiO_{4/2}]$ tetrahedra [3]. These $SiO_4^{3-}$ tetrahedral units form the backbone of the glass structure while modifying cations charge balance the silicate chains.

The ionicity of the Si—O bond, resulting from the difference in the electronegativity of Si and O, allows for the formation of Si—O—Si bonds [4], forming the backbone of various bioglass systems. Si can also bond to other atoms depending on the glass composition [5, 6]. Bond formation corresponds to a state of electronegativity equalization stated by Sanderson [7]. When a bond is formed between two atoms, X and Z, with different electronegativities, there is an electron flow from the less to the more electronegative atom.

Further, it is accepted that silica glasses undergo modification in response to the addition of other cations/atoms [8]. As an example, the alkali ions locate themselves in the structure near the non-bridging oxygen (NBO) when added to silica glasses resulting in the formation of meta, pyro and ortho-silicates. $[SiO_{4/2}]^0$, $[SiO_{3/2}O]^-$.$[SiO_{2/2}O_2]^{2-}$. $[SiO_{1/2}O_3]^{3-}$ and $[SiO_4]^{4-}$, which are present in silicate glasses, are designated as $Q^4$, $Q^3$, $Q^2$, $Q^1$ and $Q^0$ respectively, where the superscripts indicate the number of bridging oxygens (BOs) centered on the given Si atom through which it is connected to other Si atoms in the glass structure [9].

The solubility of a bioglass network is related, for example, to alkali ion content [9]; the addition of glass former cations will result in a systematic decrease in the solubility of these systems. For example, Hoppe et al. [1] disclose information on the degradation kinetics of these biomaterials and the specific effect of the released ionic dissolution products, for example Strontium ($Sr^{2+}$) and Zinc ($Zn^{2+}$) ions, impart on biological performance.

Transition metals can play a dual role in oxide glasses [10]. In some concentrations the transition metal may enter the network structure while in other concentration amounts, they may allow the oxygen ions of their former cation to break the oxygen bridges in the system, therefore acting as a glass modifier. Tantalum (Ta) is a transition metal that has been used as a bone implant [11, 12, 13] due to its physical and biological properties. The Ta ion is reported to be bioactive and biocompatible due to the formation of a stable tantalum pentoxide ($Ta_2O_5$) component on its surface [14, 15].

Studies [11, 16] have shown that Ta surfaces exhibit lower contact angles and higher surface energies than titanium (Ti) or hydroxyapatite (HA) surfaces offering a favorable biological environment for adhesion, growth and differentiation of human cells. Some processing challenges are known [13, 17].

Glass polyalkenoate cements (GPCs) were initially developed in the early 1970's for use in restorative dentistry [18]. GPCs are formed by an acid-base reaction between a water-soluble poly(acrylic) acid (PAA) and an acid-degradable fluoro-alumino-silicate bioactive glass [19, 20]. A polysalt matrix is formed in GPCs through the degradation of the glass, leading to the release of free cations which associate with the carboxylic anions from the PAA [21, 22]. The crosslinking mechanism is a continuous process during which acrylate networks are established, leading to the increase in strength over time [23]. The acid component facilitates the adhesion of the GPC to bone and plays an instrumental role in controlling the setting reaction and the resultant physical and mechanical properties [20, 24].

GPCs have been used in dentistry for over 40 years. They adhere to tooth structure and are both biocompatible and bioactive [25, 26]. They do not set with an exotherm nor do they undergo significant volumetric shrinkage with maturation [27]. However, all commercial GPCs contain, and subsequently release, aluminum ions ($Al^{3+}$) from the glass phase during setting which can have a deleterious effect on the recipient of the cement.

To address this issue, attempts have been made to modify the chemistry of the glass phase in order to increase their utility in orthopedic applications [28, 29, 30] such as vertebroplasty/kyphoplasty [31], arthroplasty [32] and sternal fixation [33, 34]. These amendments to the glass reagent can also impart an antibacterial effect to the resultant cements as they mature, due to the release of ions such as $Zn^{2+}$ and $Sr^{2+}$[35, 36].

Zinc is the second most prevalent trace element in the human body and is used for correct functioning of the immune system, healthy bone metabolism, growth and repair, as well as effective wound healing and antibacterial efficacy [37]. Strontium has been shown to be involved in the bone metabolism and to play a physiological role in growth and mineralization of bone tissue [38], therefore up-regulating osteoblastic bone formation.

Tantalum is used for orthopedic devices [39, 40, 41] due to its physical and biological properties. Their wettability, high surface energy and enhanced cell-material interactions suggest that Ta, as a metallic bio-inert material, offers a favorable biological environment for adhesion, growth and differentiation of human cells. Further, the incorporation of Ta into acrylic bone cements has been reported to increase radiopacity [42].

Median sternotomy surgery is the gold standard for cardiac procedures. Various techniques have been used for sternal fixation including wiring [43, 44, 45], plate-screw systems [46, 47] and cementing [48, 49, 50].

These techniques were critiqued in a review authored by Alhalawani & Towler [33]. Generally speaking, all of the techniques that have been utilized for sternal fixation have complications restricting their widespread adoption. Sternal wound complications (SWC) occur in 0.4-5% of patients undergoing cardiac surgery, and pose a serious risk to affected patients. In particular, deep SWCs (osteomyelitis and mediastinitis) are associated with a mortality rate between 14-47% [51, 52]. Dehiscence causes up-to 40% mortality and morbidity after median sternotomy with an incidence rate of 0.3-8% [45, 53].

The use of Gallium-containing GPCs for sternal fixation has been disclosed [34, 54, 55]. However, the adhesive properties of the GPCs deteriorated with increased Ga content when evaluated in a bovine sternal model [34].

Despite the widespread use of pharmacologic agents for treating osteoporosis, the number of fractures that occur in the elderly population continues to rise at a steady rate [56, 57]. For example, in the United States, there are nearly 1.3 million fractures every year resulting in a healthcare burden of about $10 billion per year [58, 59]. These fractures most commonly involve the upper extremities, usually at the distal radius, the proximal humerus or the spine [58, 60]. These injuries may, for example cause significant morbidity to the patient, stress for family caregivers, and/or financial burden to the health care system [57]. Current fixation and stabilisation of these injuries is not optimised and has changed little over the years. Treatment of distal radius fracture, for example, usually involves extended cast or sling immobilization, or surgical open reduction and internal fixation with pins, plates and screws followed by immobilization for 6 weeks [60, 61]. Cast or sling immobilization may be disruptive to the patient's life and may, for example, threaten their independence [62]. Non-operative management of this type may, for example, be complicated by non-union, malunion, and stiffness [60]. Surgical intervention carries with it the usual operative risks which are increased in the elderly population [60]. Development of new fracture treatment methods using modern biotechnology is desirable.

Various techniques such as dorsal and volar plating, fragment-specific plating, screw osteo-synthesis and external fixation, have been used for distal radius fracture fixation, however it still remains a challenge, especially for the elderly [63]. Stabilizing distal radius fractures using injectable adhesives including calcium phosphate cements (CPCs) has been reported [63b, 64].

SUMMARY

In one aspect, the present disclosure provides at least one example embodiment of a glass comprising, consisting essentially of or consisting of silicon dioxide ($SiO_2$), zinc oxide (ZnO), calcium oxide (CaO), strontium oxide (SrO), phosphorous pentoxide ($P_2O_5$) and a transition metal pentoxide selected from tantalum pentoxide ($Ta_2O_5$), niobium pentoxide ($Nb_2O_5$) and mixtures thereof, wherein the transition metal pentoxide is present in the glass in an amount of less than 2.0 mol %.

In another aspect, the present disclosure provides at least one example embodiment of a glass comprising, consisting essentially of or consisting of silicon dioxide ($SiO_2$), zinc oxide (ZnO), calcium oxide (CaO), strontium oxide (SrO), phosphorous pentoxide ($P_2O_5$) and tantalum pentoxide ($Ta_2O_5$), wherein the $Ta_2O_5$ is present in the glass in an amount of less than 2.0 mol %.

In an embodiment,
the $SiO_2$ is present in an amount of from about 35.0 mol % to about 60.0 mol %;
the ZnO is present in an amount of from about 25.0 mol % to about 40.0 mol %;
the CaO is present in an amount of from about 2.0 mol % to about 12.0 mol %;
the SrO is present in an amount of from about 5.0 mol % to about 15.0 mol %; and
the $P_2O_5$ is present in an amount of from about 1.0 mol % to about 5.0 mol %.

In another embodiment,
the $SiO_2$ is present in an amount of about 48 mol %;
the ZnO is present in an amount of from about 35.5 mol % to about 35.8 mol %;
the CaO is present in an amount of about 6 mol %;
the SrO is present in an amount of about 8 mol %; and
the $P_2O_5$ is present in an amount of about 2 mol %.

In an embodiment, the transition metal pentoxide is present in an amount of from about 0.2 mol % to about 0.5 mol %. In another embodiment, the ZnO is present in an amount of about 35.5 mol %; and the transition metal pentoxide is present in an amount of about 0.5 mol %. In a further embodiment, the ZnO is present in an amount of about 35.8 mol %; and the transition metal pentoxide is present in an amount of about 0.2 mol %. In an embodiment, the transition metal pentoxide is tantalum pentoxide ($Ta_2O_5$). In an embodiment, the $Ta_2O_5$ is present in an amount of from about 0.2 mol % to about 0.5 mol %. In another embodiment, the ZnO is present in an amount of about 35.5 mol %; and the $Ta_2O_5$ is present in an amount of about 0.5 mol %. In a further embodiment, the ZnO is present in an amount of about 35.8 mol %; and the $Ta_2O_5$ is present in an amount of about 0.2 mol %.

In another aspect, the present disclosure provides at least one example embodiment of a glass comprising, consisting essentially of or consisting of silicon dioxide ($SiO_2$), zinc oxide (ZnO), calcium oxide (CaO), strontium oxide (SrO), phosphorous pentoxide ($P_2O_5$) and tantalum pentoxide ($Ta_2O_5$), wherein the Ta content is greater than zero and is less than 12.0 wt %, based on the total weight of the glass, and wherein the Ta content is determined from the Ta4d peak in an X-ray photoelectron spectrum of the glass.

In an embodiment,
the O content is from about 25.0 wt % to about 50.0 wt %;
the Si content is from about 15.0 wt % to about 30.0 wt %;
the Zn content is from about 15.0 wt % to about 30.0 wt %;
the Ca content is from about 1.0 wt % to about 6.0 wt %;
the Sr content is from about 5.0 wt % to about 25.0 wt %; and
the P content is from about 2.0 wt % to about 8.0 wt %, based on the total weight of the glass, wherein the O, Si, Zn, Ca, Sr and P contents are determined from the O1s, Si2p, Zn2p3, Ca2p, Sr3p1 and P2p peaks, respectively in the X-ray photoelectron spectrum of the glass.

In another embodiment,
the O content is from about 38.0 wt % to about 38.5 wt %;
the Si content is from about 23.0 wt % to about 24.5 wt %;
the Zn content is from about 23.0 wt % to about 25.5 wt %;
the Ca content is from about 2.5 wt % to about 3.0 wt %;
the Sr content is from about 7.0 wt % to about 8.0 wt %; and
the P content is from about 1.0 wt % to about 1.5 wt %, based on the total weight of the glass, wherein the O, Si, Zn, Ca, Sr and P contents are determined from the O1s, Si2p, Zn2p3, Ca2p, Sr3p1 and P2p peaks, respectively in the X-ray photoelectron spectrum of the glass.

In an embodiment, the Ta content as determined from the Ta4d peak in the X-ray photoelectron spectrum of the glass is from about 1.6 wt % to about 3.0 wt %, based on the total weight of the glass. In another embodiment, the Zn content is about 24.9 wt %; and the Ta content is about 1.6 wt %, based on the total weight of the glass, wherein the Zn and Ta contents are determined from the Zn2p3 and Ta4d peaks, respectively in the X-ray photoelectron spectrum of the glass. In a further embodiment, the Zn content is about 23.2 wt %; and the Ta content is about 3.0 wt %, based on the total weight of the glass, wherein the Zn and Ta contents are determined from the Zn2p3 and Ta4d peaks, respectively in the X-ray photoelectron spectrum of the glass.

In another aspect, the present disclosure provides at least one example embodiment of a glass polyalkenoate cement prepared from mixing a glass of the present disclosure with an aqueous solution of a polyalkenoic acid.

In an embodiment, the polyalkenoic acid is poly(acrylic acid). In another embodiment, the poly(acrylic acid) has a weight average molecular weight ($M_w$) of about 30,000 to about 500,000, optionally about 213,000.

In a further embodiment, the poly(acrylic acid) has a median particle size of less than about 1,000 µm, optionally less than about 90 µm.

In an embodiment, the glass has an average particle size of about 5 µm to about 45 µm, optionally about 10 µm to about 11.5 µm.

In an embodiment, the glass is annealed prior to mixing with the aqueous solution of the polyalkenoic acid.

In an embodiment, the ratio by weight of the glass:aqueous solution of polyalkenoic acid is from about 1:5 to about 1.5:1. In an embodiment, the ratio by weight of the glass:aqueous solution of polyalkenoic acid is from about 1:1.5 to about 1.5:1, optionally about 1:1. In another embodiment, the ratio by weight of the polyalkenoic acid:water is from about 1:1.5 to about 1.5:1, optionally about 1:1.

In an embodiment, the working time of the cement is from about 1 minute to about 3 minutes or about 2 minutes. In an embodiment, the working time of the cement is from about 1 minute to about 5 minutes. In another embodiment, for example, where the cement is for injectable use, the working time of the cement is from about 10 minutes to about 30 minutes.

In an embodiment, the setting time of the cement, measured in accordance with ISO 9917-1:2007, is equal to or less than about 20 minutes, optionally about 190 seconds to about 210 seconds. In an embodiment, the setting time of the cement, measured in accordance with ISO 9917-1:2007, is from about 10 minutes to about 60 minutes. In another embodiment, for example, where the cement is for injectable use, the setting time of the cement, measured in accordance with ISO 9917-1:2007, is from about 1 hour to about 3 hours.

In another aspect, the present disclosure provides at least one example embodiment of a use of a cement of the present disclosure for repairing a bone or tooth in need thereof.

In an embodiment, the use is for repairing a bone. In another embodiment, the use is for fixation/closure and repair of a sternum that has been divided into at least two segments. In a further embodiment, the cement is for use in combination with an additional technique for sternal closure. In a further embodiment, the additional technique for sternal closure comprises application of sternal cable ties or wires and the cement is for use prior to application of the sternal cable ties or wires. In a further embodiment, the fixation/closure and repair is of a sternum that has been divided during a median sternotomy.

In another aspect, the present disclosure provides at least one example embodiment of a method of fixation/closure and repair of a sternum that has been divided into at least two segments, the method comprising applying a cement of the present disclosure to the segments and closing the sternum.

In an embodiment, the method further comprises applying an additional technique for sternal closure. In another embodiment of the present disclosure, the additional technique for sternal closure comprises applying sternal cable ties or wires. In a further embodiment, the method comprises applying the cement prior to applying the sternal cable ties or wires.

In an embodiment, the fixation/closure and repair is of a sternum that has been divided during a median sternotomy.

In an embodiment, the use is for fixation, stabilization and/or repair of a fracture in a bone in the wrist, elbow, knee, shoulder, spine and/or hip. In another embodiment, the cement is for use as a percutaneous injection.

In an embodiment, the poly(acrylic acid) has a weight average molecular weight ($M_w$) of about 213,000. In an embodiment, the ratio by weight of the glass:aqueous solution of polyalkenoic acid is about 1:1.5.

In an embodiment, the poly(acrylic acid) has a weight average molecular weight ($M_w$) of about 50,000. In an embodiment, the ratio by weight of the glass:aqueous solution of polyalkenoic acid is about 1:2.3.

In another aspect, the present disclosure provides at least one example embodiment of a kit for the preparation of a glass polyalkenoate cement, comprising:
a glass of the present disclosure;
a polyalkenoic acid; and
optionally instructions for mixing the glass with an aqueous solution of the polyalkenoic acid to prepare the cement.

In an embodiment, the polyalkenoic acid is poly(acrylic acid). In another embodiment, the kit further comprises water.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The present disclosure will now be described in greater detail with reference to the drawings in which.

DETAILED DESCRIPTION

I. Definitions

Figure 1:
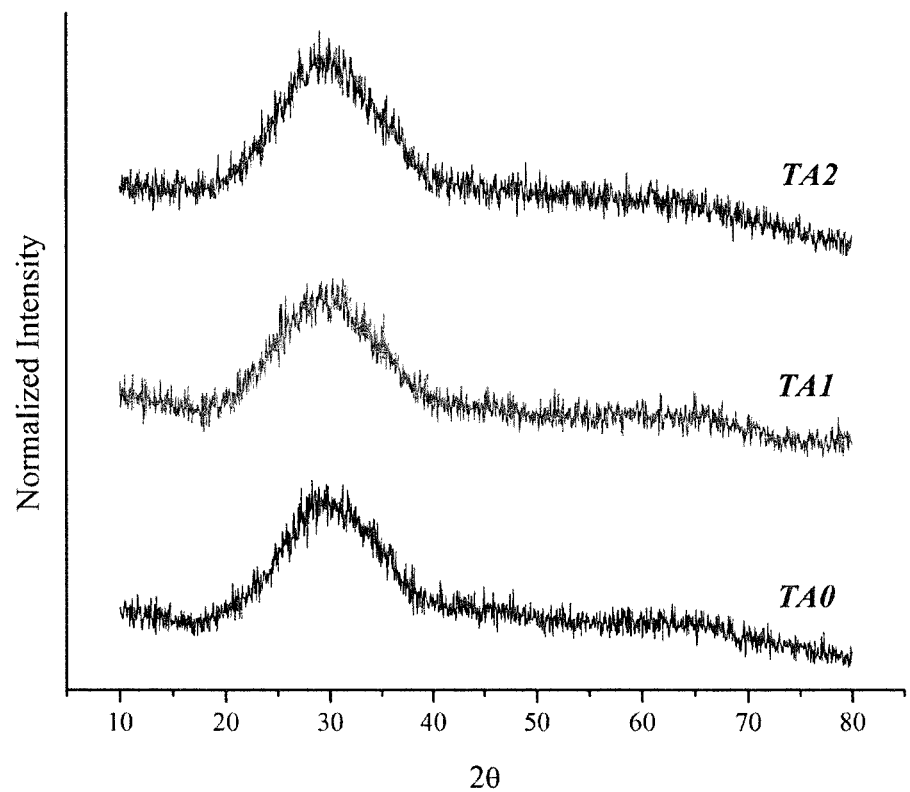
FIG. 1 shows X-ray Diffraction (XRD) traces for glasses comprising 0.2 mol % $Ta_2O_5$(TA1) and 0.5 mol % $Ta_2O_5$ (TA2) according to example embodiments of the disclosure in comparison to a control glass which did not contain $Ta_2O_5$(TA0).

Unless otherwise indicated, the definitions and embodiments described in this and other sections are intended to be applicable to all embodiments and aspects of the present disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

As used in this application, the singular forms "a", "an" and "the" include plural references unless the content clearly dictates otherwise. For example, an embodiment including "a glass" should be understood to present certain aspects with one glass or two or more additional glasses.

In embodiments comprising an "additional" or "second" component, such as an additional or second glass, the second component as used herein is chemically different from the other components or first component. A "third" component is different from the other, first, and second components, and further enumerated or "additional" components are similarly different.

The term "pharmaceutically acceptable" means compatible with the treatment of subjects, for example, animals such as humans.

II. Glasses

Bioglasses are employed for surgical augmentation in a range of hard tissue applications. Tantalum is a bioactive and biocompatible transition metal that has been used as a bone implant but has known challenges associated with its fabrication and processing. Tantalum has a range of biological and physical properties that make its incorporation into bioactive glass systems useful for various clinical applications. The studies that are presented herein describe the synthesis, characterization and properties of low tantalum-containing glasses. An $XTa_2O_5$-containing $48SiO_2$-(36-X)$ZnO$-$6CaO$-$8SrO$-$2P_2O_5$ glass series was synthesized, with X being 0, 0.2 or 0.5 mol %. The addition of small amounts of $Ta_2O_5$ did not cause crystallization of the glasses but increasing $Ta_2O_5$ content at the expense of ZnO was found to result in an increased number of bridging oxygens (BOs). This, along with the data recorded by differential thermal analysis (DTA) and magic angle spinning-nuclear magnetic resonance (MAS-NMR), shows that Ta acts as a glass former in this series. Solubility experiments showed that minor changes in the glass structure caused by Ta incorporation (0.5 mol %) exhibited greater cumulative % weight loss, pH values and cumulative $Zn^{2+}$ and $Sr^{2+}$ ion concentration over a period of 30 days of maturation, when compared to $Ta_2O_5$-free glasses. The results described herein show that replacing ZnO with $Ta_2O_5$ in silicate glasses in amounts of 0.2 or 0.5 mol % results in the formation of stronger bonds within the glass network without any adverse effects on the solubility of the glasses prepared from them. While not wishing to be limited by theory, glasses prepared with 0.2 or 0.5 mol % $Nb_2O_5$ are predicted to have similar properties to the corresponding Ta glasses due to the similarities in chemical and physical properties between these two elements.

Accordingly, in one aspect, the present disclosure provides at least one example embodiment of a glass comprising, consisting essentially of or consisting of silicon dioxide ($SiO_2$), zinc oxide (ZnO), calcium oxide (CaO), strontium oxide (SrO), phosphorous pentoxide ($P_2O_5$) and a transition metal pentoxide selected from tantalum pentoxide ($Ta_2O_5$), niobium pentoxide ($Nb_2O_5$) and mixtures thereof, wherein the transition metal pentoxide is present in the glass in an amount of less than 2.0 mol %.

In an embodiment, the glass comprises silicon dioxide ($SiO_2$), zinc oxide (ZnO), calcium oxide (CaO), strontium oxide (SrO), phosphorous pentoxide ($P_2O_5$) and a transition metal pentoxide selected from tantalum pentoxide ($Ta_2O_5$), niobium pentoxide ($Nb_2O_5$) and mixtures thereof, wherein the transition metal pentoxide is present in the glass in an amount of less than 2.0 mol %. In an embodiment, the glass consists essentially of silicon dioxide ($SiO_2$), zinc oxide (ZnO), calcium oxide (CaO), strontium oxide (SrO), phosphorous pentoxide ($P_2O_5$) and a transition metal pentoxide selected from tantalum pentoxide ($Ta_2O_5$), niobium pentoxide ($Nb_2O_5$) and mixtures thereof, wherein the transition metal pentoxide is present in the glass in an amount of less than 2.0 mol %. In an embodiment, the glass consists of silicon dioxide ($SiO_2$), zinc oxide (ZnO), calcium oxide (CaO), strontium oxide (SrO), phosphorous pentoxide ($P_2O_5$) and a transition metal pentoxide selected from tantalum pentoxide ($Ta_2O_5$), niobium pentoxide ($Nb_2O_5$) and mixtures thereof, wherein the transition metal pentoxide is present in the glass in an amount of less than 2.0 mol %.

In an embodiment, the transition metal pentoxide is niobium pentoxide ($Nb_2O_5$). In another embodiment, the transition metal pentoxide is a mixture of niobium pentoxide ($Nb_2O_5$) and tantalum pentoxide ($Ta_2O_5$). In a further embodiment, the transition metal pentoxide is tantalum pentoxide ($Ta_2O_5$).

Accordingly, in another aspect, the present disclosure provides at least one example embodiment of a glass comprising, consisting essentially of or consisting of silicon dioxide ($SiO_2$), zinc oxide (ZnO), calcium oxide (CaO), strontium oxide (SrO), phosphorous pentoxide ($P_2O_5$) and tantalum pentoxide ($Ta_2O_5$), wherein the $Ta_2O_5$ is present in the glass in an amount of less than 2.0 mol %.

In an embodiment, the glass comprises silicon dioxide ($SiO_2$), zinc oxide (ZnO), calcium oxide (CaO), strontium oxide (SrO), phosphorous pentoxide ($P_2O_5$) and tantalum pentoxide ($Ta_2O_5$), wherein the $Ta_2O_5$ is present in the glass in an amount of less than 2.0 mol %. In another embodiment, the glass consists essentially of silicon dioxide ($SiO_2$), zinc oxide (ZnO), calcium oxide (CaO), strontium oxide (SrO), phosphorous pentoxide ($P_2O_5$) and tantalum pentoxide ($Ta_2O_5$), wherein the $Ta_2O_5$ is present in the glass in an amount of less than 2.0 mol %. In a further embodiment, the glass consists of silicon dioxide ($SiO_2$), zinc oxide (ZnO), calcium oxide (CaO), strontium oxide (SrO), phosphorous pentoxide ($P_2O_5$) and tantalum pentoxide ($Ta_2O_5$), wherein the $Ta_2O_5$ is present in the glass in an amount of less than 2.0 mol %.

In an embodiment, the $SiO_2$ is present in an amount of from about 35.0 mol % to about 60.0 mol %; the ZnO is present in an amount of from about 25.0 mol % to about 40.0 mol %; the CaO is present in an amount of from about 2.0 mol % to about 12.0 mol %; the SrO is present in an amount of from about 5.0 mol % to about 15.0 mol %; and the $P_2O_5$ is present in an amount of from about 1.0 mol % to about 5.0 mol %.

In another embodiment,
the $SiO_2$ is present in an amount of about 48 mol %;
the ZnO is present in an amount of from about 35.5 mol % to about 35.8 mol %;
the CaO is present in an amount of about 6 mol %;
the SrO is present in an amount of about 8 mol %; and
the $P_2O_5$ is present in an amount of about 2 mol %.

In an embodiment, the transition metal pentoxide is present in an amount of up to about 1.0 mol % or about 0.5 mol %. In another embodiment, the transition metal pentoxide is present in an amount of from about 0.2 mol % to about 0.5 mol %. For example, in embodiments wherein the transition metal pentoxide is $Ta_2O_5$, the $Ta_2O_5$ is present in an amount of up to about 1.0 mol % or about 0.5 mol %. For example, in a further embodiment, the $Ta_2O_5$ is present in an amount of from about 0.2 mol % to about 0.5 mol %.

In an embodiment, the ZnO is present in an amount of about 35.5 mol %; and the transition metal pentoxide is present in an amount of about 0.5 mol %. In another embodiment, the ZnO is present in an amount of about 35.8 mol %; and the transition metal pentoxide is present in an amount of about 0.2 mol %. For example, in embodiments wherein the transition metal pentoxide is $Ta_2O_5$, the ZnO is present in an amount of about 35.5 mol %; and the $Ta_2O_5$ is present in an amount of about 0.5 mol %. For example, in another embodiment, the ZnO is present in an amount of about 35.8 mol %; and the $Ta_2O_5$ is present in an amount of about 0.2 mol %.

In another aspect, the present disclosure provides at least one example embodiment of a glass comprising, consisting essentially of or consisting of silicon dioxide ($SiO_2$), zinc oxide (ZnO), calcium oxide (CaO), strontium oxide (SrO), phosphorous pentoxide ($P_2O_5$) and tantalum pentoxide ($Ta_2O_5$), wherein the Ta content is greater than zero and is less than 12.0 wt %, based on the total weight of the glass, and wherein the Ta content is determined from the Ta4d peak in an X-ray photoelectron spectrum of the glass.

In an embodiment, the glass comprises silicon dioxide ($SiO_2$), zinc oxide (ZnO), calcium oxide (CaO), strontium oxide (SrO), phosphorous pentoxide ($P_2O_5$) and tantalum pentoxide ($Ta_2O_5$), wherein the Ta content is greater than zero and is less than 12.0 wt %, based on the total weight of the glass, and wherein the Ta content is determined from the Ta4d peak in an X-ray photoelectron spectrum of the glass. In another embodiment, the glass consists essentially of silicon dioxide ($SiO_2$), zinc oxide (ZnO), calcium oxide (CaO), strontium oxide (SrO), phosphorous pentoxide ($P_2O_5$) and tantalum pentoxide ($Ta_2O_5$), wherein the Ta content is greater than zero and is less than 12.0 wt %, based on the total weight of the glass, and wherein the Ta content is determined from the Ta4d peak in an X-ray photoelectron spectrum of the glass. In a further embodiment, the glass consists of silicon dioxide ($SiO_2$), zinc oxide (ZnO), calcium oxide (CaO), strontium oxide (SrO), phosphorous pentoxide ($P_2O_5$) and tantalum pentoxide ($Ta_2O_5$), wherein the Ta content is greater than zero and is less than 12.0 wt %, based on the total weight of the glass, and wherein the Ta content is determined from the Ta4d peak in an X-ray photoelectron spectrum of the glass.

In an embodiment,
the O content is from about 25.0 wt % to about 50.0 wt %;
the Si content is from about 15.0 wt % to about 30.0 wt %;
the Zn content is from about 15.0 wt % to about 30.0 wt %;
the Ca content is from about 1.0 wt % to about 6.0 wt %;
the Sr content is from about 5.0 wt % to about 25.0 wt %; and
the P content is from about 2.0 wt % to about 8.0 wt %,
based on the total weight of the glass, wherein the O, Si, Zn, Ca, Sr and P contents are determined from the O1s, Si2p, Zn2p3, Ca2p, Sr3p1 and P2p peaks, respectively in the X-ray photoelectron spectrum of the glass.

In another embodiment,
the O content is from about 38.0 wt % to about 38.5 wt %;
the Si content is from about 23.0 wt % to about 24.5 wt %;
the Zn content is from about 23.0 wt % to about 25.5 wt %;
the Ca content is from about 2.5 wt % to about 3.0 wt %;
the Sr content is from about 7.0 wt % to about 8.0 wt %; and
the P content is from about 1.0 wt % to about 1.5 wt %,
based on the total weight of the glass, wherein the O, Si, Zn, Ca, Sr and P contents are determined from the O1s, Si2p, Zn2p3, Ca2p, Sr3p1 and P2p peaks, respectively in the X-ray photoelectron spectrum of the glass.

In another embodiment, the Ta content is greater than zero and is less than or equal to about 6.0 wt % or about 3.0 wt %, based on the total weight of the glass, wherein the Ta content is determined from the Ta4d peak in the X-ray photoelectron spectrum of the glass. In an embodiment, the Ta content as determined from the Ta4d peak in the X-ray photoelectron spectrum of the glass is from about 1.6 wt % to about 3.0 wt %, based on the total weight of the glass.

In an embodiment, the Zn content is about 24.9 wt %; and the Ta content is about 1.6 wt %, based on the total weight of the glass, wherein the Zn and Ta contents are determined from the Zn2p3 and Ta4d peaks, respectively in the X-ray photoelectron spectrum of the glass.

In another embodiment, the Zn content is about 23.2 wt %; and the Ta content is about 3.0 wt % or about 2.7 wt %, based on the total weight of the glass, wherein the Zn and Ta contents are determined from the Zn2p3 and Ta4d peaks, respectively in the X-ray photoelectron spectrum of the glass.

In an embodiment, the glasses of the present disclosure are prepared by a method comprising mixing the desired amounts of suitable glass precursors (e.g. powdered analytical grade silica, zinc oxide, calcium carbonate, strontium carbonate, ammonium dihydrogen phosphate and the transition metal oxide such as tantalum oxide), melting the mixture at a suitable temperature, for example about 1650° C. for a suitable time, for example about 1.5 hours then shock quenching the melt in water to obtain frit. The frit can optionally be dried in an oven at a suitable temperature, for example about 100° C. for a suitable time, for example about 1 hour, optionally ground using any suitable means, for example using a ball mill under suitable conditions, for example at about 400 rounds per minute for about 15 minutes, then optionally sieved through a suitable mesh, for example an about 45 µm mesh. Optionally, the method further comprises annealing the glass under suitable conditions, for example for a duration and at a temperature suitable to relieve internal stresses within the glass network and avoid crystallization such as a time of about 6 hours to about 24 hours or about 12 hours at a temperature of about 10° C. to about 20° C. or about 15° C. below a glass transition temperature obtained for the glass using differential thermal analysis (DTA).

III. Cements

With over a million median sternotomy surgeries performed worldwide every year, sternal wound complications have posed a serious risk to the affected patients. A rigid therapeutic sternal fixation device has therefore been used. In the studies shown herein, the incorporation of up to 0.5 mol % of tantalum pentoxide ($Ta_2O_5$), in exchange for zinc oxide (ZnO), into $SiO_2$—ZnO—CaO—SrO—$P_2O_5$ glass system is described. The effect of Ta incorporation on the physical, chemical and biocompatibility properties of the glass polyalkenoate cements (GPCs) prepared from them have also been described. The incorporation of elements such as Zn and Sr into an Al-free GPC offers, for example, the possibility of synergistic slow release at the implant site for antibacterial and bone regenerating biomaterials. The data obtained have showed that low amounts of $Ta_2O_5$ incorporation (0.2 or 0.5 mol %) into the reference glass system results in improved working times, radiopacity, ion solubility, and long-term mechanical stability. The cements have also shown clear antibacterial and antifungal activity against both Gram-negative (*Escherichia coli*) and Gram-positive prokaryotes (*Staphylococcus aureus* and *Streptococcus epidermidis*), as well as eukaryotes (*Fusarium solani*). Cytotoxicity testing showed that Ta incorporation results in no observed toxicity and may simulate osseointegration in animal models. These new metallic-containing biomaterial adhesives may, for example, be useful for sternal fixation and repair. As a permanent implant, the formulated adhesives can be used in conjunction with sternal cable ties to offer advantageous fixation for patients and may reduce post-operative complications such as bacterial infections and/or pain from micro-motion. While not wishing to be limited by theory, cements prepared with 0.2 or 0.5 mol % $Nb_2O_5$ are predicted to have similar properties to the corresponding Ta cements due to the similarities in chemical and physical properties between these two elements therefore glasses containing, similar amounts of $Nb_2O_5$ may also be useful, for example, in the preparation of niobium-containing cements that have rheological properties suitable for orthopedic applications.

Accordingly, in another aspect, the present disclosure provides at least one example embodiment of a glass polyalkenoate cement prepared from mixing a glass of the present disclosure with an aqueous solution of a polyalkenoic acid.

The polyalkenoic acid can be any suitable polyalkenoic acid. For example, it will be appreciated by a person skilled in the art that in clinical applications, a pharmaceutically acceptable polyalkenoic acid is used. In an embodiment, the polyalkenoic acid is selected from poly(acrylic acid), poly(itaconic acid), poly(maleic acid), copolymers thereof and combinations thereof. In another embodiment of the present disclosure, the polyalkenoic acid is poly(acrylic acid). It will be appreciated by a person skilled in the art that the molecular weight of the polyalkenoic acid such as poly(acrylic acid) is selected such that it is high enough that the cement has suitable setting and mechanical properties and low enough such that it is mixable. The molecular weight may also vary, for example, depending on the use of the cement. For example, cements that are used in percutaneous injections may have a lower molecular weight than cements used, for example, in sternal fixation. In an embodiment, the poly(acrylic acid) has a weight average molecular weight ($M_w$) of about 30,000 to about 500,000. In another embodiment, the poly(acrylic acid) has a weight average molecular weight ($M_w$) of about 35,000 to about 250,000. In another embodiment, the poly(acrylic acid) has an $M_w$ of about 200,000 to about 250,000 or about 213,000. In a further embodiment, the poly(acrylic acid) has a $M_w$ of about 35,000 to about 75.000 or about 50,000.

In a further embodiment, the poly(acrylic acid) has a median particle size of less than about 1,000 µm. It is an embodiment that the poly(acrylic acid) has a median particle size of less than about 90 µm.

In an embodiment, the glass has an average particle size of about 5 µm to about 45 µm. In another embodiment of the present disclosure, the glass has an average particle size of about 10 µm to about 11.5 µm.

In an embodiment, the glass is annealed prior to mixing with the aqueous solution of the polyalkenoic acid. It will be appreciated by a person skilled in the art that annealing hardens the glass surface thus may slow down its reaction with the acid chains of the polyalkenoic acid. Accordingly, cements in which the glass is annealed prior to mixing with the aqueous solution of the polyalkenoic acid may, for example, have longer working and/or setting times.

It will be appreciated by a person skilled in the art that in preparing cements for clinical use, the water is pharmaceutically acceptable water.

The ratio by weight of the glass:aqueous solution of polyalkenoic acid may vary depending on the use of the cement. In an embodiment, the ratio by weight of the glass:aqueous solution of polyalkenoic acid is from about 1:5 to about 1.5:1. In another embodiment of the present disclosure, the ratio by weight of the glass:aqueous solution of polyalkenoic acid is from about 1:1.5 to about 1.5:1. In another embodiment, the ratio by weight of the glass:aqueous solution of polyalkenoic acid is about 1:1.5 to about 1:1. In another embodiment, the ratio by weight of the glass:aqueous solution of polyalkenoic acid is about 1:1.5. In another embodiment, the ratio by weight of the glass:aqueous solution of polyalkenoic acid is about 1:1. In a further embodiment, the ratio by weight of the glass:aqueous solution of polyalkenoic acid is from about 1:4 to about 1:2. In another embodiment, the ratio by weight of the glass:aqueous solution of polyalkenoic acid is from about 1:4 to about 1:2.33. In another embodiment, the ratio by weight of the glass:aqueous solution of polyalkenoic acid is about 1:2.3. In another embodiment, the ratio by weight of the glass:aqueous solution of polyalkenoic acid is about 1:4.

In an embodiment, the ratio by weight of the polyalkenoic acid:water is from about 1:1.5 to about 1.5:1. In another embodiment, the ratio by weight of the polyalkenoic acid:water is about 1:1.

It will be appreciated by a person skilled in the art that the setting and working times may vary, for example, based on the amount of the Ta and/or the ratio of the glass:aqueous solution of polyalkenoic acid. The selection of a suitable setting time may also depend, for example, on the use of the cement, for example for sternal fixation versus for injection. The selection of a suitable setting time for a particular use can be made by the person skilled in the art. In an embodiment, the working time of the cement is from about 1 minute to about 3 minutes. In another embodiment of the present disclosure, the working time of the cement is about 2 minutes. In an embodiment, the working time of the cement is from about 1 minute to about 5 minutes, about 3 minutes to about 5 minutes or about 4.2 minutes. In another embodiment, for example, where the cement is for injectable use, the working time of the cement is from about 10 minutes to about 30 minutes, about 15 minutes to about 25 minutes or about 19.4 minutes.

In an embodiment, the setting time of the cement, measured in accordance with ISO 9917-1:2007, is equal to or less than about 20 minutes. In another embodiment, the setting time of the cement, measured in accordance with ISO 9917-1:2007, is about 190 seconds to about 210 seconds. In an embodiment, the setting time of the cement, measured in accordance with ISO 9917-1:2007, is from about 10 minutes to about 60 minutes, about 45 minutes to about 60 minutes or about 53 minutes. In another embodiment, for example, where the cement is for injectable use, the setting time of the cement, measured in accordance with ISO 9917-1:2007, is from about 1 hour to about 3 hours, about 120 minutes to about 200 minutes or about 164 minutes.

IV. Methods and Uses

The glasses and cements of the present disclosure are new therefore the present disclosure includes all uses for the glasses and cements of the present disclosure, including but not limited to use in therapeutic methods and as research tools whether alone or in combination with another technique.

The data obtained have showed that low amounts of $Ta_2O_5$ incorporation (0.2 or 0.5 mol % were tested) into the reference glass system used in the cements of the present disclosure results in improved working times, radiopacity, ion solubility, and long-term mechanical stability. The cements have also shown clear antibacterial and antifungal activity against both Gram-negative (*Escherichia coli*) and Gram-positive prokaryotes (*Staphylococcus aureus* and *Streptococcus epidermidis*), as well as eukaryotes (*Fusarium solani*). Cytotoxicity testing showed that Ta incorporation results in no observed toxicity and may simulate osseo-integration in animal models. These new metallic-containing biomaterial adhesives may, for example, be useful for sternal fixation and repair. As a permanent implant, the formulated adhesives can be used in conjunction with sternal cable ties to offer advantageous fixation for patients and may reduce post-operative complications such as bacterial infections and/or pain from micro-motion. Studies described in greater detail herein below relating to percutaneous upper extremity fracture fixation, a full arm cadaver test for injectability, biomechanical testing of cadaveric bones, and using an in vivo ovine model have shown that cements containing low amounts of $Ta_2O_5$ incorporation may, for example, be useful in sternal fixation and for fixation, stabilization and/or repair of a fracture in a bone such as in the wrist, elbow, knee, shoulder, spine and/or hip. While not wishing to be limited by theory, cements prepared with 0.2 or 0.5 mol % $Nb_2O_5$ are predicted to have similar properties to the corresponding Ta cements due to the similarities in chemical and physical properties between these two elements therefore glasses containing, similar amounts of $Nb_2O_5$ may also be useful, for example, in the preparation of niobium-containing cements that have rheological properties suitable for orthopedic applications.

Accordingly, in another aspect, the present disclosure provides at least one example embodiment of a method of repairing a bone or tooth in need thereof, the method comprising applying a cement of the present disclosure to a site of the bone or tooth in need of repair. In another aspect, the present disclosure provides at least one example embodiment of a use of a cement of the present disclosure for repairing a bone or tooth in need thereof. In another aspect, the present disclosure provides at least one example embodiment of a cement of the present disclosure for use to repair a bone or tooth in need thereof.

In another aspect, the present disclosure provides at least one example embodiment of a method of repairing a bone or tooth in need thereof, the method comprising:
  preparing a glass polyalkenoate cement by mixing a glass of the present disclosure with an aqueous solution of a polyalkenoic acid; and
  applying the cement to a site of the bone or tooth in need of repair.

In another aspect, the present disclosure provides at least one example embodiment of a use of a glass of the present disclosure for the preparation of a cement for repairing a bone or tooth in need thereof. In another aspect, the present disclosure provides at least one example embodiment of a glass of the present disclosure for use to prepare a cement for repairing a bone or tooth in need thereof. It will be appreciated by a person skilled in the art that embodiments relating to preparing the cement can be varied as described herein for the cements of the present disclosure.

In an embodiment, the methods or uses are for repairing a bone. In another embodiment, the methods or uses are for repairing a tooth.

In an embodiment, the bone in need of repair is a sternum that has been divided into at least two segments. Accordingly, in another aspect, the present disclosure provides at least one example embodiment of a method of fixation/closure and repair of a sternum that has been divided into at least two segments, the method comprising applying a cement of the present disclosure to the segments and closing the sternum. In another aspect, the present disclosure provides at least one example embodiment of a use of a cement of the present disclosure for fixation/closure and repair of a sternum that has been divided into at least two segments. In another aspect, the present disclosure provides at least one example embodiment of a cement of the present disclosure for use in fixation/closure and repair of a sternum that has been divided into at least two segments.

In another aspect, the present disclosure provides at least one example embodiment of a method of fixation/closure and repair of a sternum that has been divided into at least two segments, the method comprising:

preparing a glass polyalkenoate cement by mixing a glass of the present disclosure with an aqueous solution of a polyalkenoic acid;

applying the cement to the segments; and closing the sternum.

In another aspect, the present disclosure provides at least one example embodiment of a use of a glass of the present disclosure for the preparation of a cement for fixation/closure and repair of a sternum that has been divided into at least two segments. In another aspect, the present disclosure provides at least one example embodiment of a glass of the present disclosure for use to prepare a cement for fixation/closure and repair of a sternum that has been divided into at least two segments. It will be appreciated by a person skilled in the art that embodiments relating to preparing the cement can be varied as described herein for the cements of the present disclosure.

In an embodiment, the sternum has been divided into two segments. In another embodiment, the fixation/closure and repair is of a sternum that has been divided during a median sternotomy.

In an embodiment of the methods of the present disclosure, the method further comprises applying an additional technique for sternal closure. Similarly, in an embodiment of the uses of the present disclosure, the cement is for use in combination with an additional technique for sternal closure. Additional techniques for sternal closure are known to the person skilled in the art. For example, in an embodiment of the present disclosure, the additional technique for sternal closure comprises applying sternal cable ties or wires.

The cements of the present disclosure may, for example, decrease or stop micromotion (i.e. where both segments of the sternum move against each other), which is an issue known to result from using sternal cable ties or wires in isolation and is the main source of pain when sternotomy is repaired with means such as sternal cable ties or wires in isolation. Accordingly, applying or using the cement prior to applying the sternal cable ties or wires may, for example, offer additional stability. Accordingly, in an embodiment of the methods of the present disclosure, the method comprises applying the cement prior to applying the sternal cable ties or wires. Similarly, in an embodiment of the uses of the present disclosure, the cement is for use prior to the use of the sternal cable ties or wires.

The cements of the present disclosure may also be useful, for example, in fracture fixation, stabilization and/or repair in a wrist, spine (e.g. vertebroplasty or kyphoplasty), shoulder, elbow, knee and/or hip or in total joint replacement. Accordingly, in an embodiment, the bone in need of repair is fracture in a bone in the wrist, elbow, knee, shoulder, spine and/or hip. Accordingly, in another aspect, the present disclosure provides at least one example embodiment of a method of fixation, stabilization and/or repair of a fracture in a bone in the wrist, elbow, knee, shoulder, spine and/or hip, the method comprising applying a cement of the present disclosure to the fracture and setting the cement under conditions to fixate, stabilize and/or repair the fracture. In another aspect, the present disclosure provides at least one example embodiment of a use of a cement of the present disclosure in fixation, stabilization and/or repair of a fracture in a bone in the wrist, elbow, knee, shoulder, spine and/or hip. In another aspect, the present disclosure provides at least one example embodiment of a cement of the present disclosure for use in fixation, stabilization and/or repair of a fracture in a bone in the wrist, elbow, knee, shoulder, spine and/or hip.

In another aspect, the present disclosure provides at least one example embodiment of a method of fixation, stabilization and/or repair of a fracture in a bone in the wrist, elbow, knee, shoulder, spine and/or hip, the method comprising:

preparing a glass polyalkenoate cement by mixing a glass of the present disclosure with an aqueous solution of a polyalkenoic acid;

applying the cement to the fracture; and setting the cement under conditions to fixate, stabilize and/or repair the fracture.

In another aspect, the present disclosure provides at least one example embodiment of a use of a glass of the present disclosure for the preparation of a cement for fixation, stabilization and/or repair of a fracture in a bone in the wrist, elbow, knee, shoulder, spine and/or hip. In another aspect, the present disclosure provides at least one example embodiment of a glass of the present disclosure for use to prepare a cement for fixation, stabilization and/or repair of a fracture in a bone in the wrist, elbow, knee, shoulder, spine and/or hip. It will be appreciated by a person skilled in the art that embodiments relating to preparing the cement can be varied as described herein for the cements of the present disclosure.

In an embodiment, applying the cement to the fracture comprises percutaneously injecting the cement into the fracture. Similarly, in an embodiment, the cement is for use as a percutaneous injection. In another embodiment, the cement is injected via a syringe connected to a suitable gauge of needle such as a 14 gauge or a 16 gauge needle. The gauge of the needle may depend, for example, on the viscosity of the wet cement and therefore may depend, for example, on the ratio by weight of the glass:aqueous solution of polyalkenoic acid of the cement. For example, in an embodiment, the ratio by weight of the glass:aqueous solution of polyalkenoic acid is about 1:2.3 and the needle is a 14 gauge needle. In another embodiment, ratio by weight of the glass:aqueous solution of polyalkenoic acid is about 1:4 and the needle is a 16 gauge needle. In a further embodiment, the injection is carried out under fluoroscopic guidance.

In an embodiment, the fracture is selected from a distal fracture of the radius, a proximal fracture of the humerus and a distal fracture of the femur.

In an embodiment, the bone in need of repair is a bone in need of total joint replacement. Accordingly, in another aspect, the present disclosure provides at least one example embodiment of a method of total joint replacement comprising applying a layer of a cement of the present disclosure to a surface of a bone and affixing a joint prosthesis to the bone via the cement layer. In another aspect, the present disclosure provides at least one example embodiment of a cement of the present disclosure for attaching a joint prosthesis to a bone in a total joint replacement. In another aspect, the present disclosure provides at least one example embodiment of a cement of the present disclosure for use to attach a joint prosthesis to a bone in a total joint replacement. Cemented-type joint prostheses used in total joint replacements are known to the person skilled in the art.

In another aspect, the present disclosure provides at least one example embodiment of a method of total joint replacement, comprising:

preparing a glass polyalkenoate cement by mixing a glass of the present disclosure with an aqueous solution of a polyalkenoic acid;

applying a layer of the cement to a surface of a bone; and affixing a joint prosthesis to the bone via the cement layer.

In another aspect, the present disclosure provides at least one example embodiment of a glass of the present disclosure for the preparation of a cement for attaching a joint prosthesis to a bone in a total joint replacement. In another aspect, the present disclosure provides at least one example embodiment of a glass of the present disclosure for use to prepare a cement for attaching a joint prosthesis to a bone in a total joint replacement. It will be appreciated by a person skilled in the art that embodiments relating to preparing the cement can be varied as described herein for the cements of the present disclosure.

The cements of the present disclosure may also be useful, for example, in dental applications such as dental restoration or luting applications.

In an embodiment, the tooth in need of repair is a tooth missing a tooth structure. Accordingly, in another aspect, the present disclosure provides at least one example embodiment of a method of dental restoration of a missing tooth structure, comprising filling the missing tooth structure with a cement of the present disclosure. In another aspect, the present disclosure provides at least one example embodiment of a use of a cement of the present disclosure for filling a missing tooth structure. In another aspect, the present disclosure provides at least one example embodiment of a cement of the present disclosure for use to fill a missing tooth structure.

In another aspect, the present disclosure provides at least one example embodiment of a method of dental restoration of a missing tooth structure, the method comprising:

preparing a glass polyalkenoate cement by mixing a glass of the present disclosure with an aqueous solution of a polyalkenoic acid; and filling the missing tooth structure with the cement.

In another aspect, the present disclosure provides at least one example embodiment of a use of a glass of the present disclosure for the preparation of a cement for filling a missing tooth structure. In another aspect, the present disclosure provides at least one example embodiment of a glass of the present disclosure for use to prepare a cement to fill a missing tooth structure. It will be appreciated by a person skilled in the art that embodiments relating to preparing the cement can be varied as described herein for the cements of the present disclosure.

In an embodiment, the tooth in need of repair is a tooth in need of a prosthesis or appliance. In another aspect, the present disclosure provides at least one example embodiment of a method of attaching a prosthesis or appliance to a tooth comprising applying a layer of a cement of the present disclosure to a surface of a tooth and luting the prosthesis or appliance to the tooth via the cement layer. In another aspect, the present disclosure provides at least one example embodiment of a use of a cement of the present disclosure as a luting agent for attaching a prosthesis or appliance to a tooth. In another aspect, the present disclosure provides at least one example embodiment of a cement of the present disclosure for use as a luting agent for attaching a prosthesis or appliance to a tooth. Prostheses and appliances used in dental applications are known to the person skilled in the art and include, for example, brackets or braces used in orthodontic applications.

In another aspect, the present disclosure provides at least one example embodiment of a method of attaching a prosthesis or appliance to a tooth, the method comprising:

preparing a glass polyalkenoate cement by mixing a glass of the present disclosure with an aqueous solution of a polyalkenoic acid;

applying a layer of the cement to a surface of a tooth; and luting the prosthesis or appliance to the tooth via the cement layer.

In another aspect, the present disclosure provides at least one example embodiment of a glass of the present disclosure for the preparation of a cement luting agent for attaching a prosthesis or appliance to a tooth. In another aspect, the present disclosure provides at least one example embodiment of a glass of the present disclosure for use to prepare a cement luting agent for attaching a prosthesis or appliance to a tooth. It will be appreciated by a person skilled in the art that embodiments relating to preparing the cement can be varied as described herein for the cements of the present disclosure.

V. Kits

In another aspect, the present disclosure provides at least one example embodiment of a kit for the preparation of a glass polyalkenoate cement, comprising:

a glass of the present disclosure;

a polyalkenoic acid; and optionally instructions for mixing the glass with an aqueous solution of the polyalkenoic acid to prepare the cement.

In an embodiment, the polyalkenoic acid is poly(acrylic acid).

In an embodiment, the kit further comprises water. It will be appreciated by a person skilled in the art that in the kits of the present disclosure, the water is housed in a separate vessel than the glass of the present disclosure.

It will also be appreciated by a person skilled in the art that embodiments of the glass in the kits of the present disclosure can be varied as described herein for the embodiments of the glasses of the present disclosure.

The following non-limiting examples are illustrative of the present disclosure:

EXAMPLES

Example 1: Investigating the Effect of Tantalum Substitution for Zinc on the Structure and Solubility of $SiO_2$—$ZnO$—$SrO$—$CaO$—$P_2O_5$ Bioglass In a previous article [6], a wholly new silicate-glass series was synthesized in which ZnO was substituted with 2-8 mol % $Ta_2O_5$. In that work, it was showed that Ta incorporation into silicate-based glasses was possible by the melt-quenching process. It was also observed that Ta behaved as a glass former whereas Zn acted as a glass intermediate, depending on its content, in that particular glass system. However, these novel glasses cannot be used to prepare glass polyalkenoate cements (GPCs) for use in sternal fixation because data (see Example 3, below) showed that high Ta-containing glasses have, for example rheology (setting and working times) that are deemed unsuitable for sternal applications. The work herein relates to formulated glass that was synthesized containing lower $Ta_2O_5$ contents (0.2 or 0.5 mol %). This example also characterizes the structure and solubility of the glass system under study.

I. Experimental (a) Glass Synthesis

Three glasses were used for this study (Table 1); a $Ta_2O_5$-free $SiO_2$—ZnO—CaO—SrO—$P_2O_5$ glass (TA0) and two $Ta_2O_5$-containing glasses (TA1 and TA2). The desired amounts of analytical grade silica, zinc oxide, calcium carbonate, strontium carbonate, ammonium dihydrogen phosphate and tantalum oxide (Fisher Scientific, Ottawa, ON, Canada; Sigma-Aldrich, Oakville, ON, Canada) were weighed out and hand-mixed using a spatula. Platinum (Pt) crucibles and a Lindberg/Blue M model furnace (Lindberg/Blue M, Asheville, N.C. USA) with a UP550 controller were used for melting the sieved powders (1650° C., 1.5 h). The melts were shock quenched in water to obtain frit which was then dried in an oven (100° C., 1 h), ground using a ball mill (400 rounds per minute, 15 min), sieved once more through a 45 µm mesh and annealed for 12 h to relieve internal stresses within the glass network. The glass powders of the selected compositions were then used for subsequent characterization.

TABLE 1

Composition of the glass series.

| | $SiO_2$ | ZnO | CaO | SrO | $P_2O_5$ | $Ta_2O_5$ |
|---|---|---|---|---|---|---|
| | Mol % | | | | | |
| TA0 | 48.0 | 36.0 | 6.0 | 8.0 | 2.0 | 0.0 |
| TA1 | 48.0 | 35.8 | 6.0 | 8.0 | 2.0 | 0.2 |
| TA2 | 48.0 | 35.5 | 6.0 | 8.0 | 2.0 | 0.5 |
| | Wt % | | | | | |
| TA0 | 35.8 | 36.4 | 7.5 | 14.7 | 5.7 | 0.0 |
| TA1 | 35.5 | 35.8 | 7.4 | 14.5 | 5.7 | 1.1 |
| TA2 | 35.0 | 35.1 | 7.3 | 14.3 | 5.6 | 2.7 |

(b) Glass Structural and Thermal Characterization

X-Ray Diffraction (XRD):

A Bruker D2 Phaser desktop X-ray diffractometer (Bruker AXS Inc., WI, USA) was used to obtain X-ray diffraction patterns from the glasses at room temperature (23±1° C.). Glass powder samples were packed into stainless steel sample holders. With the X-ray generator set at 30 kV and 30 mA, a copper anode was used to produce a divergent beam with an average Kα wavelength of 1.541874 Å. The range of 10-80° 2θ with a step size of 0.02° 2θ and a count time of 10 s per step were used for the measurements. X'Pert Highscore™ data analysis software version 1.0 d (PANalytical, Almelo, The Netherlands) was employed to find peak parameters.

Particle Size Analysis (PSA):

The particle size distribution (PSD) of each glass series was recorded using a Multisizer 4 Particle size analyzer (Beckman Coulter, Fullerton, Calif., USA). The glass powder samples (n=5) were evaluated in the range of 2 to 60 µm with a run length of 60 s. A background analysis was performed and subtracted. The fluid used in this case was a sodium chloride (NaCl) electrolyte solution at a temperature range of 10-37° C. The relevant volume statistics were calculated on each glass composition. The average diameters (n=5) at the 10%, 50%, and 90% of the cumulative volume distribution ($d_{10}$, $d_{50}$ and $d_{90}$, respectively) were recorded.

Scanning Electron Microscopy-Energy Dispersive Spectroscopy (SEM-EDS):

Sample imaging was carried out with an FEI Co. Quanta 200F Environmental Scanning Electron Microscope equipped with an EDAX Genesis Energy-Dispersive Spectrometer (Oxford Instruments X-max, Netherlands). Secondary electron (SE) and backscattered electron (BSE) images were taken on glass particles and polished disc surfaces. All EDS spectra were collected at 20 kV using a beam current of 26 nA. Quantitative EDS spectra was subsequently converted into relative concentration data (n=3).

Differential Thermal Analysis (DTA):

A combined differential thermal analyzer-thermal gravimetric analyzer (DTA-TGA; SDT 2960 Simultaneous DSC-TGA, TA Instruments, DW, USA) was used to study the thermal properties of the glasses. A heating rate of 20° C./min was employed using an air atmosphere with alumina in a matched platinum crucible as a reference and then cooled to room temperature at the same rate. Sample measurements were carried out every 6 s between 30° C. and 1200° C. Data analysis was performed using NETZSCH Proteus software, V. 6 (Netzsch-Geratebau GmbH, Selb, Germany).

X-Ray Photoelectron Spectroscopy (XPS):

The powders' chemical compositions as well as local chemical environment were analyzed using a PHI Quantera Scanning X-ray photoelectron Microprobe (XPS). The XPS data sets were collected with Al Kα X-rays (monochromatic, beam size=100 µm) at an output power of 26.2 watts, with a photon energy of 1486.6 eV and a step size of ~0.025 eV. Survey scans (~0.5 eV step size) were performed with a pass energy of 140 eV to gain qualitative information such as peak identification and peak position. Peaks identified in all survey scans were used to adjust high resolution scan binding energy range, pass energy (26 eV) and beam dwelling time (~100 ms). The beam sweeps for each high resolution scan were adjusted to yield a signal-to-noise ratio of >100:1. The analyzed area was 1-2 mm in diameter.

Magic Angle Spinning-Nuclear Magnetic Resonance (MAS-NMR): $^{29}$Si MAS-NMR spectra were recorded at 7.05 T (tesla) on a Varian Unity Inova 300 FT-NMR spectrometer (Palo Alto, Calif., USA), equipped with a cross polarization-magic angle spinning (CP-MAS) probe. The glass samples were placed in a zirconia sample tube with a diameter of 7 mm. The sample spinning speed at the magic angle to the external magnetic field was 5 kHz. $^{29}$Si MAS NMR spectra were taken at 59.59 MHz with 7.0-ls pulse length (pulse angle, p/2), 100-second recycle delays, where the signals from 2126, 1837 and 1880 pulses were accumulated for TA-0, TA-1 and TA-2, respectively. $^{29}$Si NMR chemical shifts are reported in ppm, with PDMS (polydimethylsiloxane) as the external reference (−34 ppm vs. TMS 0 ppm). All NMR spectra were recorded in a room for exclusive use of NMR, where the room temperature was kept at 300 K by means of an air-conditioner. Data analysis of the NMR spectra was performed by nonlinear curve-fitting using ORIGIN software (Microcal software Inc., Northhampton, Mass., USA).

(c) Effect of Glass Structure on Ion Release and Solubility

Disc Sample Preparation and Degradation Analysis:

Disc samples were prepared by weighing 0.1 g powder into a stainless steel die (sample diameter 1.5×6φ mm) which was pressed under 2.5 tons of pressure for 30 seconds. Disc samples were kept amorphous by annealing at $T_g$+10° C. for 12 h. The surface area of each glass disc was then calculated from the dimensions measured using an electronic precision caliper (Cedarlane Laboratories Ltd., Hornby, ON, Canada). Disc samples were then weighed and immersed in measured quantities (10 ml) of de-ionized (DI) water. All samples were maintained at 37° C. At various time points (1, 7 and 30 days), the DI water was removed for pH and ion release analysis. Then the discs were removed, dried in an incubator for 24 h, and weighed before being immersed in fresh volumes of DI water. This study was conducted in triplicate, and the data plotted as cumulative degradation (percentage weight loss per unit area, as a function of time). Eq. 1 was then used to obtain the % weight loss per unit area:

$$\% \text{ of weight loss} = \frac{M_o - M_t}{A} \times 100 \quad (1)$$

where, in the above equation, $M_o$ is the initial weight in g, $M_t$ is the weight at time t in g and A is the surface area in $cm^2$.

pH Analysis:

The pH measurements were collected using a Corning 430 pH meter (Corning Life Sciences, Acton, Mass.). Prior to testing, the pH electrode was calibrated using pH buffer solutions 4.00±0.02 and 7.00±0.02 (Fisher Scientific, Pittsburgh, Pa.). Sterile DI water (pH=6.0) was used as a control and was measured at each time period.

Ion Release Profiles:

Each sample (n=3) was immersed in 10 ml of DI water for 1, 7 and 30 days prior to testing. The ion release profile of each specimen was measured using atomic absorption spectroscopy (AAS) on a Perkin-Elmer Analyst 800 (Perkin Elmer, Mass., USA). AAS calibration standards for Sr and Zn elements were prepared from a stock solution (Sigma-Aldrich, Oakville, ON, Canada) on a gravimetric basis. Three target calibration standards were prepared for each ion and DI water was used as a control. Owing to the much greater expected concentration of ions, samples were diluted in DI water at 1:10 ratio. The final cumulative concentration was calculated from the results of the measurements taking into account the dilution factor.

II. Results and Discussion (a) Glass Structural and Thermal Characterization

X-ray Diffraction patterns were recorded for each of the formulated glasses and are presented in FIG. 1. XRD showed that all fired glasses were fully amorphous; i.e. that no crystalline species were observed to be present in any one of TA0, TA1 or TA2 during glass forming. The results presented herein indicate that changes in the properties of the glasses will be attributed to $Ta_2O_5$ incorporation rather than phase changes/separation in the glasses.

Particle size analysis (PSA) was conducted for each glass composition and the results are presented in Table 2. The PSA results were comparable for all glasses under study implying that changes through the series would be related to chemistry, not physicality, of the glasses.

TABLE 2

Particle size analysis data for the glass series.

| | Average (µm) | $d_{10}$ (µm) | $d_{50}$ (µm) | $d_{90}$ (µm) |
|---|---|---|---|---|
| TA0 | 11.5 | 6.4 | 8.8 | 20.2 |
| TA1 | 11.1 | 6.4 | 8.6 | 18.9 |
| TA2 | 10.3 | 6.4 | 8.4 | 16.1 |

Figure 2:
FIG. 2 shows a scanning electron microscopy (SEM) image (top) and the corresponding energy dispersive spectroscopy (EDS) qualitative spectra (bottom) for TA0. Scale bar in SEM image shows 100 µm.
Figure 2:
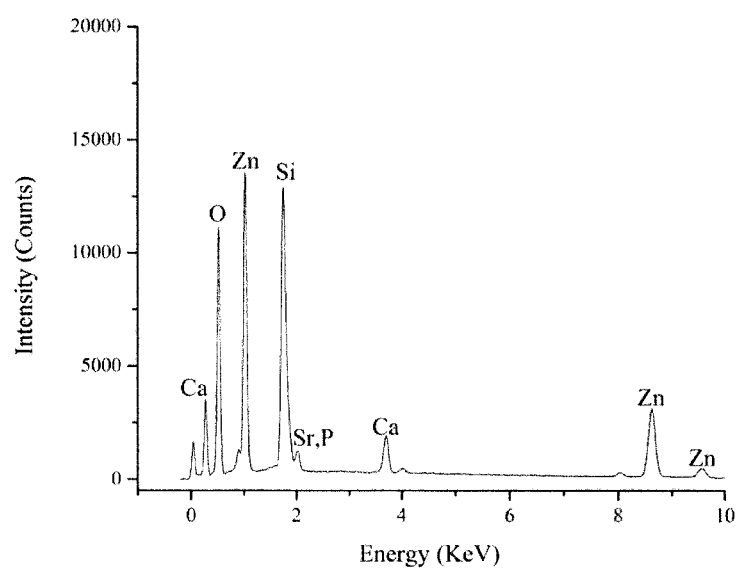
Figure 3:
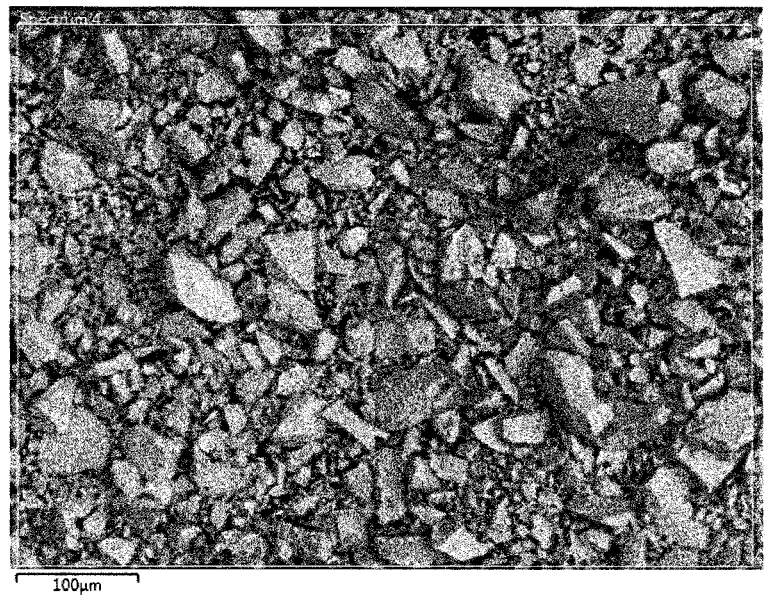
FIG. 3 shows an SEM image (top) and the corresponding EDS qualitative spectra (bottom) for TA1. Scale bar in SEM image shows 100 µm.
Figure 3:
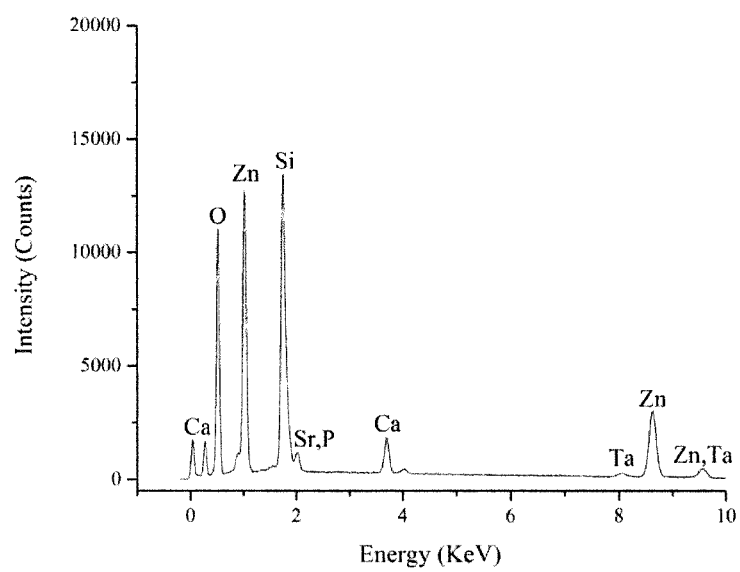
Figure 4:
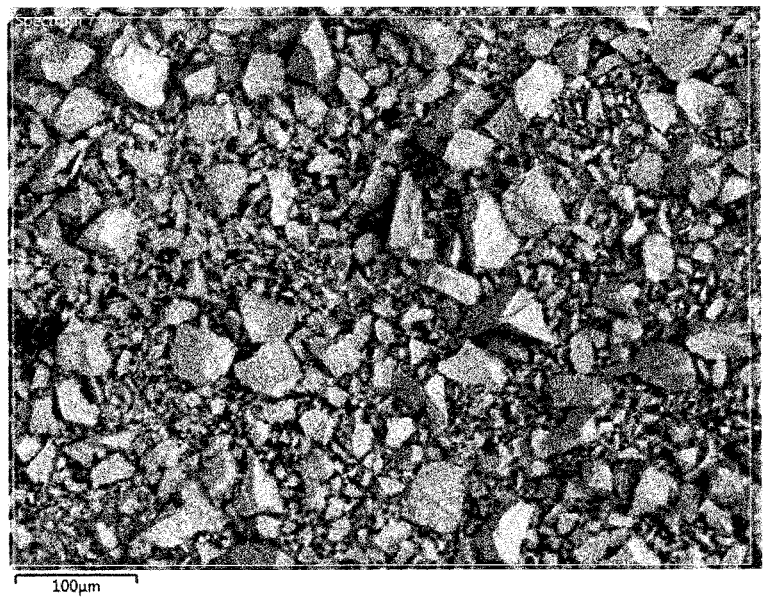
FIG. 4 shows an SEM image (top) and the corresponding EDS qualitative spectra (bottom) for TA2. Scale bar in SEM image shows 100 μm.
Figure 4:
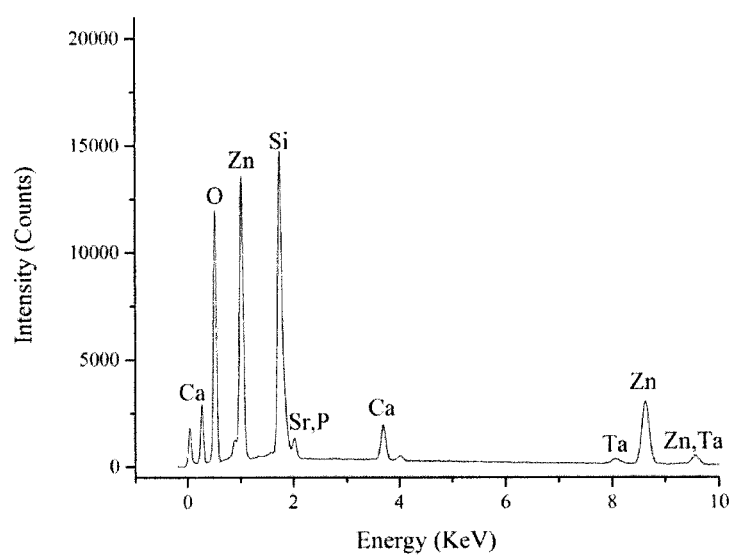

SEM was employed to provide compositional contrast images that result from different atomic number elements and their distribution within the glasses. EDS analysis was also performed to provide qualitative spectra and quantitative relative proportions (wt %) of the particular elements from the SEM backscattered images. SEM (top images) and EDS (bottom images) results of the glass series are presented in FIG. 2 (TA0), FIG. 3 (TA1) and FIG. 4 (TA2) which show similar morphology for the glasses through the series. Thus, the incorporation of $Ta_2O_5$ did not cause any observed changes in the morphology or the mean particle size of the glass series. The chemical composition (n=3) of the glass series from quantitative EDS is in Table 3. Qualitative EDS spectra showed that TA0 contains Si, Zn, Ca, Sr, and P, while TA1 and TA2 were found to have the same elements but with the addition of Ta, thus confirming the starting formulation of each glass.

TABLE 3

Quantitative EDS of the glass series.

| | TA0 (wt %) | TA1 (wt %) | TA2 (wt %) |
|---|---|---|---|
| O | 41.8 | 42.2 | 41.8 |
| Si | 14.4 | 14.9 | 14.9 |
| Zn | 31.8 | 30.6 | 29.9 |
| Ca | 2.9 | 2.7 | 2.7 |
| Sr | 7.8 | 7.4 | 7.4 |
| P | 1.5 | 1.4 | 1.4 |
| Ta | 0 | 0.7 | 1.9 |

It was found that Ta increased from 0.0 to 1.9 wt % while Zn decreased from 31.8 to 29.9 wt %, with increasing $Ta_2O_5$ content from 0.0 to 2.7 wt %, respectively. The Si:Zn ratio was ~1:1 in the original glass (wt %, Table 1), however the EDS results showed a 1:2 rate. While not wishing to be limited by theory, this may be attributed to the high signal present for O and/or the ion diffusion through the glass. Initial quantitative analysis of the glass composition by using EDS led to the following observations:

(1) The EDS results are usually collected at low vacuum therefore the oxygen content recorded by EDS represents BO and NBO and may also represent oxygen in the surrounding environment. This may result in a significant discrepancy in predicting the elemental bulk composition.

(2) EDS provides the quantitative relative proportions of the particular elements but not the oxides, therefore EDS results cannot be solely used for comparing the chemical composition of the processed and formulated glass.

(3) The penetration depth of the EDS is ~2-5 µm, hence the results also include bulk composition data. This advantage of EDS analysis may however be associated with masking and overlapping issues resulting in significant discrepancy and compositional heterogeneity.

Figure 5:
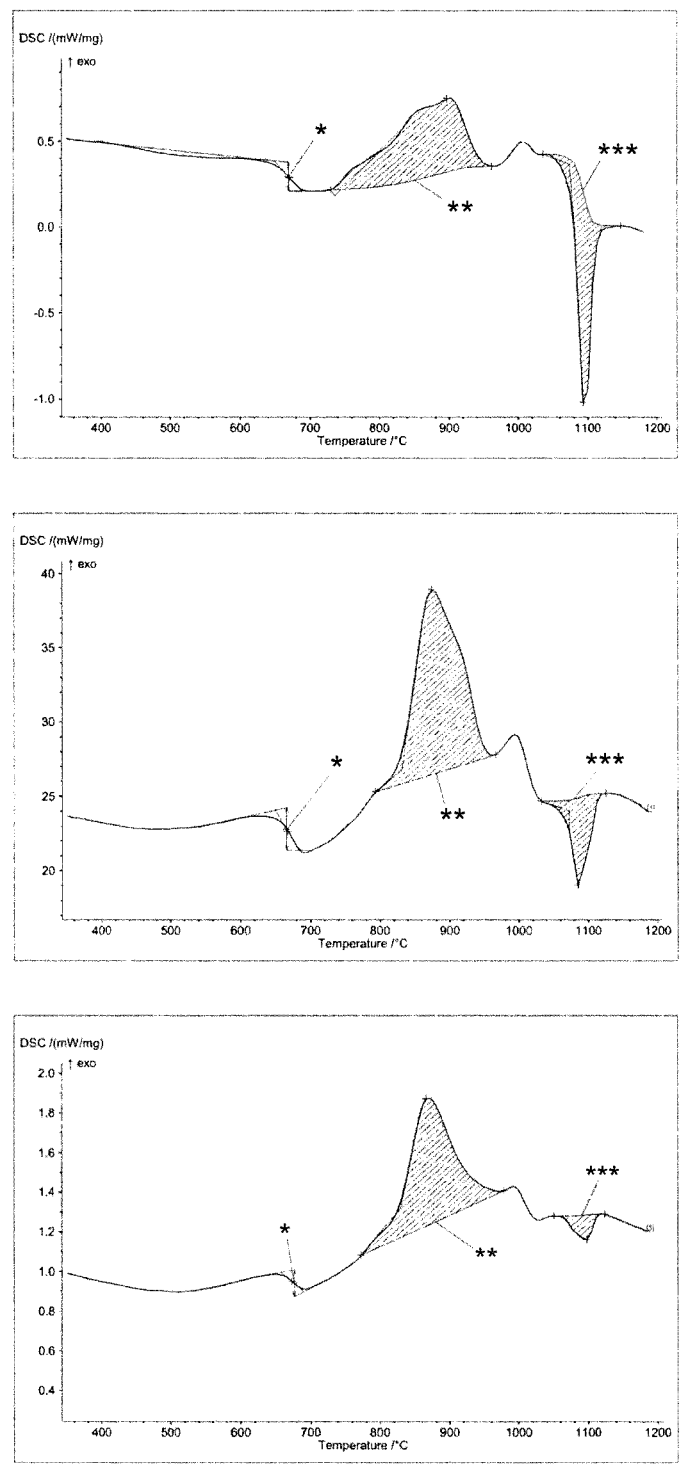
FIG. 5 shows differential thermal analysis (DTA) curves of the glass series: TA0 (top), TA1 (middle) and TA2 (bottom).

Thermal profiles of the glasses are presented in FIG. 5 (from top to bottom: TA0, TA1 and TA2) and associated data is in Table 4. In FIG. 5, the glass transition is labelled "*", the crystallization is labelled "" and the melting is labelled "*" in each of the thermal profiles.

TABLE 4

Data from differential thermal analysis of glass series.

| Glass Transition | Crystallization | Melting |
|---|---|---|
| TA0 | | |
| Onset: 648.7° C. | Area: 161.5 J/g | Area: −87.76 J/g |
| Mid: 669.7° C. | Peak*: 896.7° C. | Peak*: 1093.5° C. |
| Inflection: 670.6° C. | Onset: 735.9° C. | Onset: 1073.9° C. |

TABLE 4-continued

Data from differential thermal analysis of glass series.

| Glass Transition | Crystallization | Melting |
|---|---|---|
| End: 688.8° C. Delta Cp*: 0.511 J/(g*K) | Width: 150.8° C. Height: 0.4276 mW/mg | Width: 24.3° C. Height: 1.233 mW/mg |

TA1

| | | |
|---|---|---|
| Onset: 649.7° C. Mid: 666.1° C. Inflection: 667.9° C. End: 684.4° C. Delta Cp*: 8,709 J/(g*K) | Area: 2796 J/g Peak*: 873.9° C. Onset: 831.7° C. Width: 88.3° C. Height: 12.52 mW/mg | Area: −526 J/g Peak*: 1085.2° C. Onset: 1072.4° C. Width: 33.8° C. Height: 5.88 mW/mg |

TA2

| | | |
|---|---|---|
| Onset: 658.2° C. Mid: 676.5° C. Inflection: 673.3° C. End: 690.1° C. Delta Cp*: 0.407 J/(g*K) | Area: 145.6 J/g Peak*: 866.3° C. Onset: 829.4° C. Width: 81.6° C. Height: 0.6429 mW/mg | Area: −10.97 J/g Peak*: 1097.5° C. — Width: 34.7° C. Height: 0.1269 mW/mg |

The glass transition temperature was observed at 670° C., 666° C. and 677° C. for TA0, TA1 and TA2, respectively. Previous studies [6, 65] have shown that the addition of transition metals, such as $Ta_2O_5$, to bio-glasses increases the glass transition temperature ($T_g$) and facilitates incorporation of the transition metal oxide inside the glass network. While not wishing to be limited by theory, the shift in $T_g$ implies increased glass stability, which, while not wishing to be limited by theory, may be attributed to the formation of BO groups. The glass transition is followed by an exothermic peak caused by glass crystallization ($T_c$). TA1 and TA2 showed an exothermic crystallization reaction at around 874° C. and 866° C., respectively while TA0 showed a broad peak around that region, observed at 897° C. While not wishing to be limited by theory, the slow crystallization of TA0 can be attributed to 'interfering' nucleation and oxidation transitions as well as the slow diffusion rates of the reactants in TA0. Finally, the melting temperature for TA0 appears at 1094° C. For TA1 and TA2, endothermic peaks appeared at 1085° C. and 1098° C., respectively. While not wishing to be limited by theory, this last endothermic process for TA1 and TA2 was assigned to initial decomposition and melting of some of the glass elements. The glass melting temperature of TA1 and TA2 was not observed, as substituting ZnO with $Ta_2O_5$ increased melting temperature. Increasing Ta content caused a marked increase in the peak maxima of DTA curves at higher temperatures. While not wishing to be limited by theory, this may indicate increased stability and homogeneity of the glass reactants.

Figure 6:
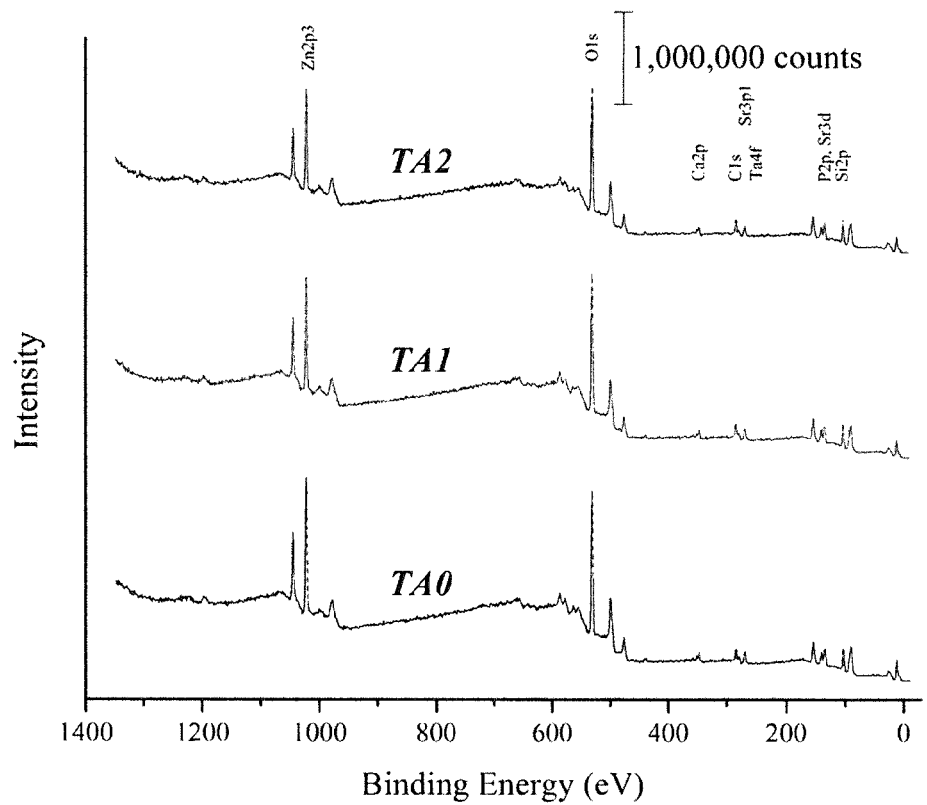
FIG. 6 shows X-ray photoelectron spectroscopy (XPS) survey scans of the glass series: TA2 (top), TA1 (middle) and TA0 (bottom).

X-ray photoelectron spectroscopy was employed to derive information on the elemental composition and speciation of matter by assessing the electronic structure of the atoms residing within the surface region of the matter being analyzed. The survey spectrum of the glasses formulated is shown in FIG. 6. Besides the Si2p, Zn2p3, P2p, Ca2p, Sr3d5, Ta4d and O1s peaks, a C1s peak can be seen in the survey scans which, while not wishing to be limited by theory, may be attributed to 'adventitious carbon' present due to the adsorption of impurities during the glass firing process. The presence of this peak is common and does not affect the interpretation of the results. The XPS survey scan results (FIG. 6) are in good agreement with EDS data. TA0 was found to contain Si2p, Zn2p3, P2p, Ca2p, Sr3d5, and O1s, while TA1 and TA2 contain each of these elements in addition to Ta4d, reflecting the initial glass formulation.

Elemental compositions of the O1s, Si2p, Zn2p3, P2p, Ca2p, Sr3d5, and Ta4d peaks are presented in Table 5. Presenting the elemental composition of the C1s peak can make it difficult to compare relative changes between EDS and XPS results therefore the elemental composition of the C1s peak is not presented. The elemental composition of all other peaks was adjusted accordingly. Comparing the glass composition obtained from both EDS and XPS with the initial batch formulation (Table 1), it is clear that XPS gives better approximation, particularly when comparing the Ta, Zn and Si content. The wt % of Si and Zn are almost equal in the expected glass compositions (Table 1) to those from the XPS results whereas the EDS quantitative analysis showed a Zn content that is almost twice as large as that of the Si. Further, EDS and XPS show that Ta and O content increases while the content of Zn decreases as a function of $Ta_2O_5$, thus they present a similar trend to the precursor glass formulations. XPS is a surface technique and therefore explanations offered around the glass composition are subject to the assumption that the bulk of the glass is similar in composition of the surface. However, although EDS quantitative analysis presents the composition of the bulk of the glass, the XPS results record compositions closer to those from the initial batch calculation.

TABLE 5

Elemental composition (wt %) of the glass series as determined by XPS.

| | O1s | Si2p | Zn2p3 | Ca2p | Sr3p1 | P2p | Ta4d |
|---|---|---|---|---|---|---|---|
| TA0 | 37.7 | 23.3 | 26.9 | 3.0 | 7.8 | 1.4 | 0.0 |
| TA1 | 38.1 | 23.5 | 24.9 | 2.9 | 7.5 | 1.1 | 1.6 |
| TA2 | 38.3 | 23.9 | 23.2 | 2.8 | 7.1 | 1.1 | 3.0 |

Figure 7:
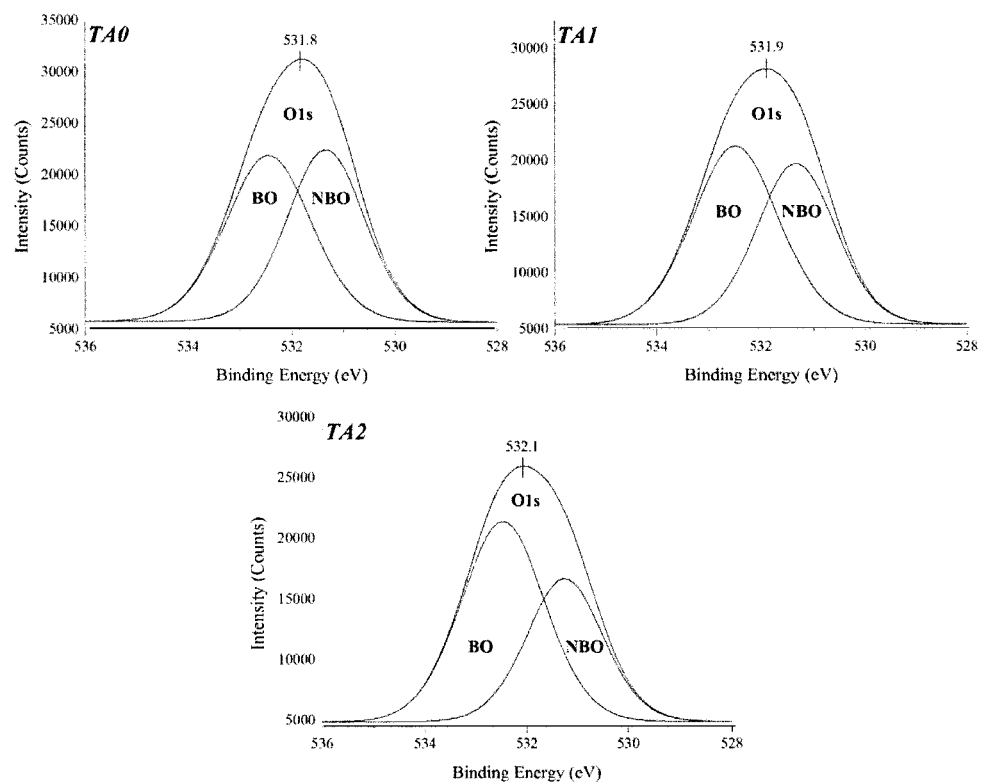
FIG. 7 shows curve fitting of the O1s spectra for the glass series with respect to bridging oxygen (BO) and non-bridging oxygen (NBO) contributions: TA0 (top left), TA1 (top right) and TA2 (bottom).

High resolution O1s spectra were also obtained from XPS to determine the effect of $Ta_2O_5$ substitution. The O1s spectra were curve fitted with respect to BO and NBO contributions and are presented in FIG. 7. It is clear from FIG. 7 that the binding energy of the O1s spectrum shifts slightly from 531.8 to 532.1 eV, as a function of $Ta_2O_5$ content. While not wishing to be limited by theory, this may be indicative of increasing the BO content in the glass, further suggesting that tantalum acts as a network former in these glasses. Table 6 presents the peak positions for the BO and the NBO and their corresponding atomic % (at %). BO and NBO remained at 531.3 eV and 532.5 eV regardless of $Ta_2O_5$ content. However, increasing $Ta_2O_5$ content was found to increase the at % of BO peaks on the expense of NBO content, thus increasing the BO/NBO ratio. While not wishing to be limited by theory, these results may suggest decreased bioactivity, as the $Ta_2O_5$ content increases, resulting from the formation of additional Si—O—BO that are known to have a negative effect on the ion exchange process.

TABLE 6

Peak positions (eV) for the BO and the NBO peaks and their corresponding at %, obtained from the curve fitting of the O1s peak, of the glass series.

| | TA0 | TA1 | TA2 |
|---|---|---|---|
| O1s (NBO) | 531.3 | 531.3 | 531.3 |
| at % | 45.2 | 45.2 | 39.6 |
| O1s (BO) | 532.5 | 532.5 | 532.5 |
| at % | 54.8 | 54.8 | 60.4 |

Figure 8:
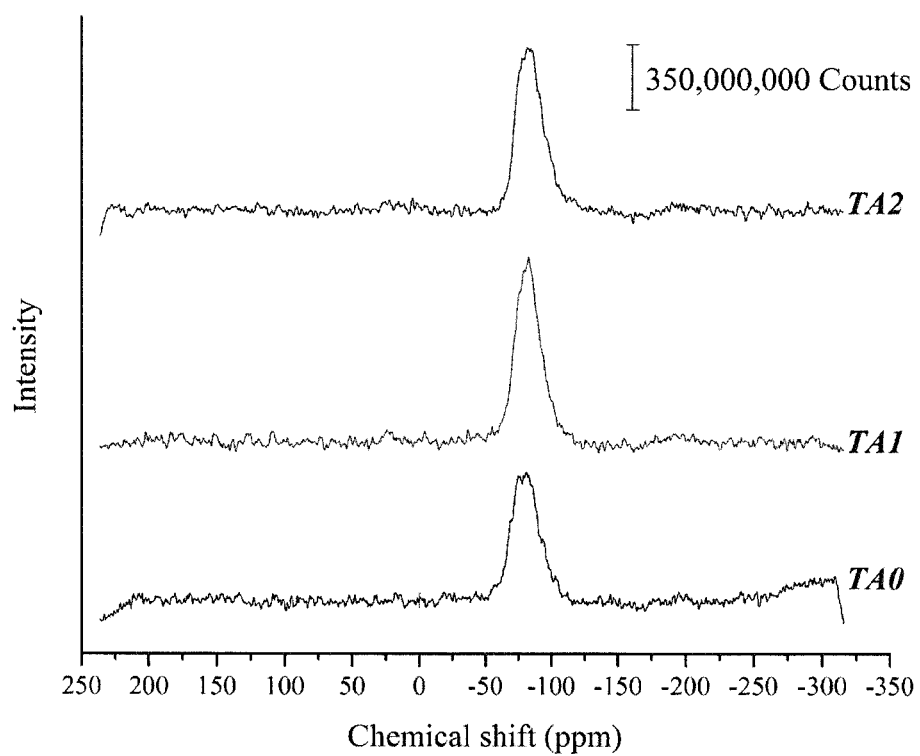
FIG. 8 shows magic angle spinning-nuclear magnetic resonance (MAS-NMR) spectra of the glass series: TA2 (top), TA1 (middle) and TA0 (bottom) in the chemical shift region of from 225 ppm to −325 ppm. Scale bar shows 350,000,000 counts.

MAS-NMR was employed to further investigate the structural effects of $Ta_2O_5$ incorporation. Chemical shift in MAS-NMR represents structural changes around the Si atom which lies in the region of −60 to −120 ppm for $SiO_4$ tetrahedra [66]. FIG. 8 shows the MAS-NMR spectra of the TA0, TA1 and TA2 samples. All glass samples showed similar broad resonances at ~−80 ppm. It was seen that there are slight chemical shift differences with the chemical shift of TA0 (−80.1)>TA1 (−82.4)>TA2 (−83.5). A shift in ppm in a negative direction, as presented with TA1 and TA2, is indicative of an increase in BO species attached to the silicon, within the glass which is in line with the XPS results presented hereinabove. Previous studies have indicated that chemical shifts in the region between −60 and −120 ppm represent structural changes around the Si atom in a four coordinate state and suggested the presence of $Q^1$, $Q^2$ and $Q^3$ species at −78, −85 and −95 ppm respectively [66]. All glasses show a broad peak around −80 ppm. While not wishing to be limited by theory, this may suggest that the formulated glasses contain both $Q^1/Q^2$. However, the broadness of the spectral envelope in all peaks suggests the presence of multiple Q-species and indicates that silicon is present in distorted environments within the glass structure.

(b) Glass Solubility Properties

Figure 9:
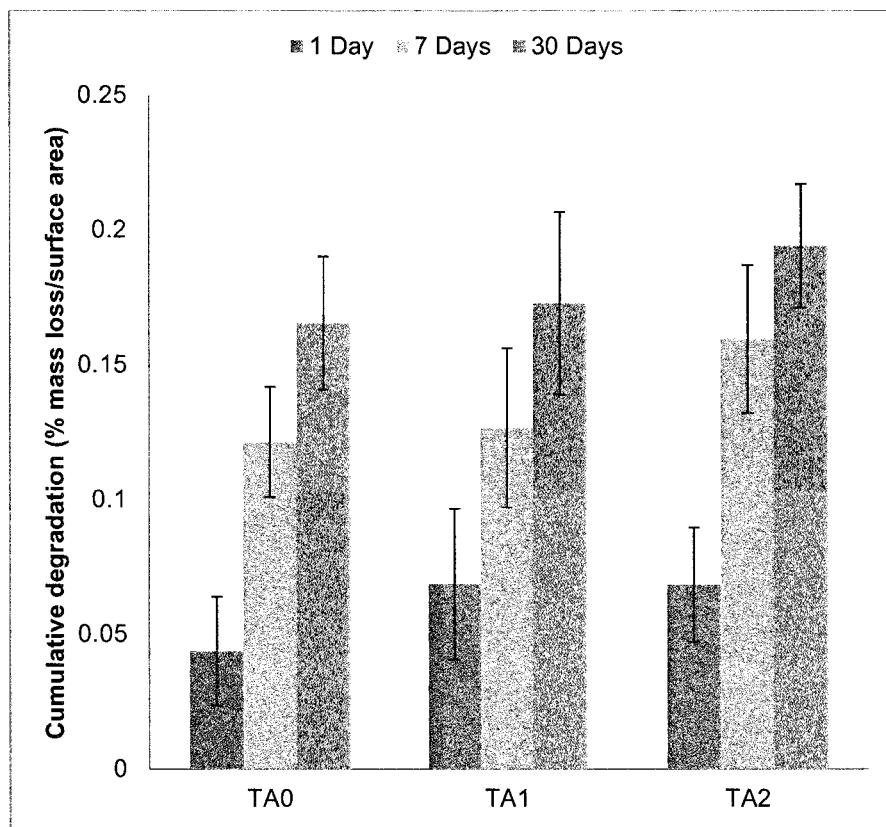
FIG. 9 is a plot of percentage weight loss of the glass series in deionized water as a function of time for TA0 (left), TA1 (middle) and TA2 (right). Error bars represent standard deviation from the mean.
Figure 10:
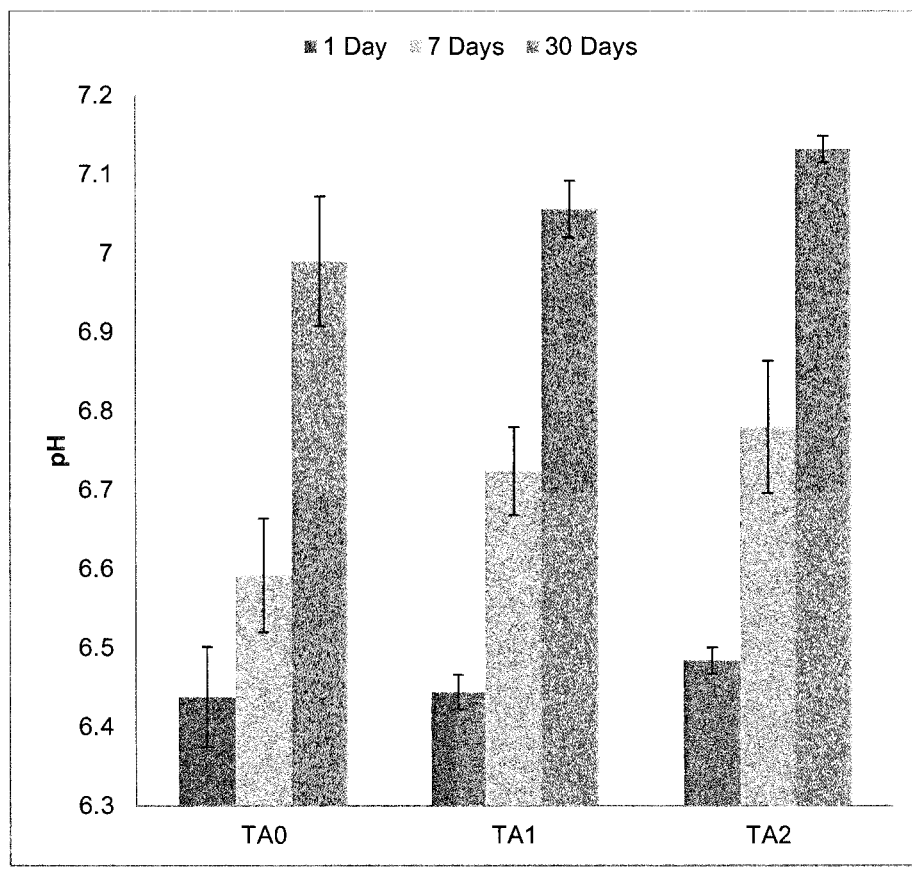
FIG. 10 is a plot of pH measurements of the glass series during glass solubility in deionized water for TA0 (left), TA1 (middle) and TA2 (right). Error bars represent standard deviation from the mean.
Figure 11:
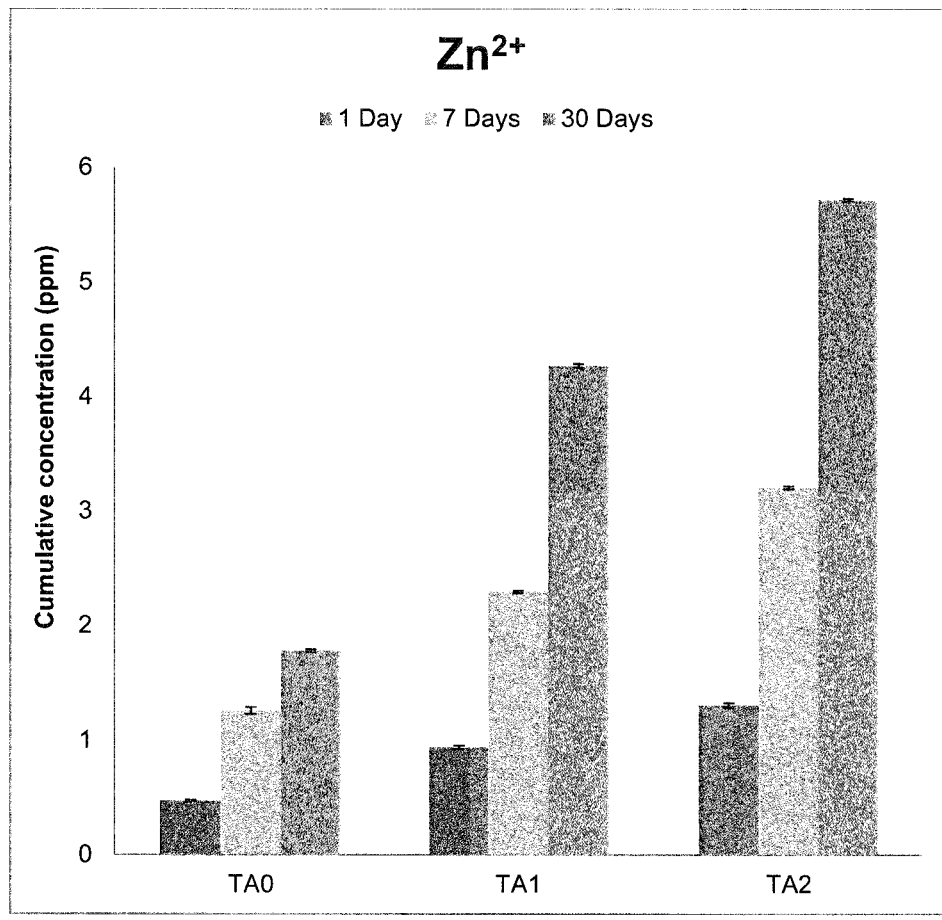
FIG. 11 is a plot of the ion release profile of $Zn^{2+}$ ions during glass solubility in deionized water over time for TA0 (left), TA1 (middle) and TA2 (right). Error bars represent standard deviation from the mean.
Figure 12:
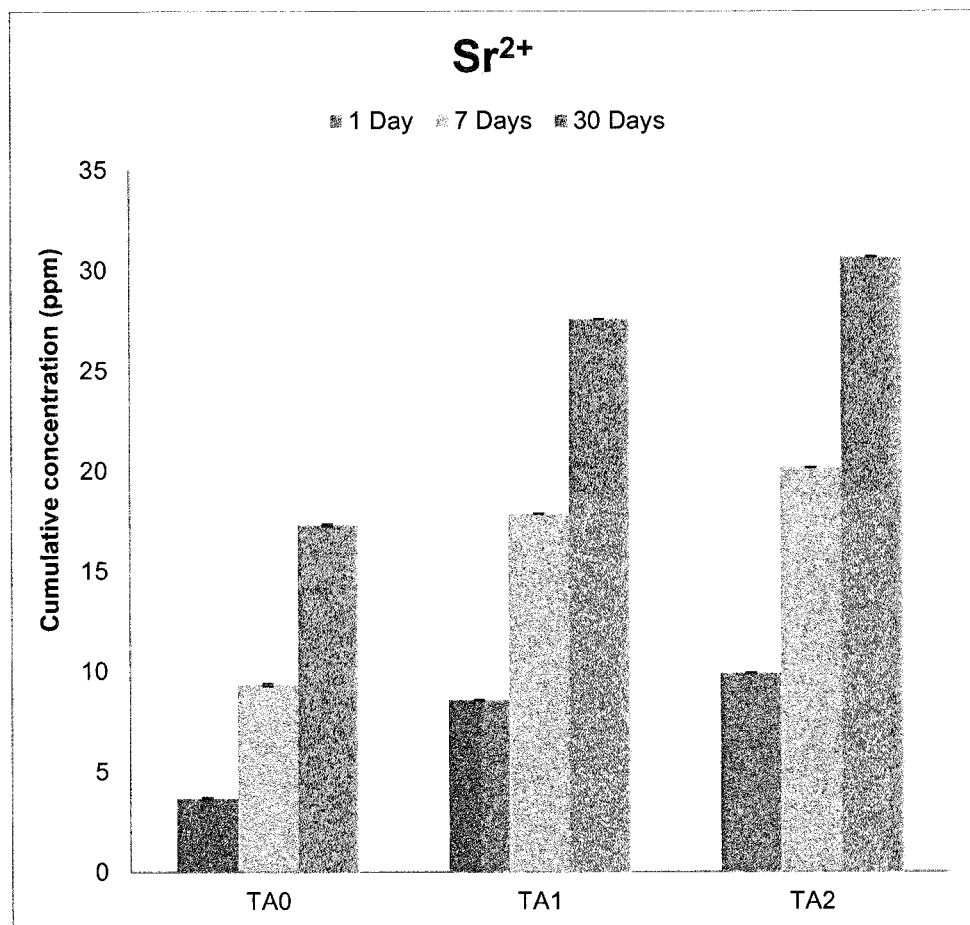
FIG. 12 is a plot of the ion release profile of $Sr^{2+}$ ions during glass solubility in deionized water over time for TA0 (left), TA1 (middle) and TA2 (right). Error bars represent standard deviation from the mean.

As discussed above, substituting $Ta_2O_5$ with ZnO resulted in an increased BO/NBO ratio which correlated with a shift in the thermal events in these glasses to higher temperatures. However, incorporation of $Ta_2O_5$s, replacing ZnO, was found to increase the cumulative % weight loss per unit area of the glasses under study (see FIG. 9). The results of pH measurements (FIG. 10) as well as ion release studies of $Zn^{2+}$ (FIG. 11) and $Sr^{2+}$ ions (FIG. 12) reflected the degradation behavior of the glasses.

The TA2 formulation exhibits greater cumulative % weight loss, pH values and cumulative $Zn^{2+}$ and $Sr^{2+}$ ion concentration over a period of 30 days of maturation, when compared to TA1 and/or TA0 glasses. Tables 7 and 8 show the statistics around these studies, which consider both the effect of $Ta_2O_5$ content and aging on the obtained results. Significant differences (Table 7, p<0.05) in the cumulative % weight loss were observed when comparing 1 day with 30 day results for TA0 and TA2 samples. However, no significant difference (Table 8, p>0.05) in the cumulative % weight loss was observed when results were compared with respect to $Ta_2O_5$ content.

Significant changes (Table 7, p<0.05) in the pH measurements were obtained when results were compared with respect to all time modalities. With regards to $Ta_2O_5$ content, there were significant differences in pH measurements (Table 8, p<0.05) between TA0 and TA1 measured at day 7 and between TA0 and TA2 measured at 7 and 30 days.

Ion release studies of both $Zn^{2+}$ and $Sr^{2+}$ showed significant differences (p<0.05) when results were compared with respect to aging time as well as $Ta_2O_5$ content (see Tables 7 and 8).

TABLE 7

Glass solubility statistics (with respect to aging time).

|  |  | TA0 | TA1 | TA2 |
|---|---|---|---|---|
| % weight loss | 1 day vs. 7 day | 0.082 | 0.615 | 0.059 |
|  | 7 day vs. 30 day | 0.536 | 0.921 | 0.984 |
|  | 1 day vs. 30 day | 0.006* | 0.099 | 0.009* |
| pH | 1 day vs. 7 day | 0.018* | 0.000* | 0.000* |
|  | 7 day vs. 30 day | 0.000* | 0.000* | 0.000* |
|  | 1 day vs. 30 day | 0.000* | 0.000* | 0.000* |

TABLE 7-continued

Glass solubility statistics (with respect to aging time).

|  |  | TA0 | TA1 | TA2 |
|---|---|---|---|---|
| Sr ion release | 1 day vs. 7 day | 0.000* | 0.000* | 0.000* |
|  | 7 day vs. 30 day | 0.000* | 0.000* | 0.000* |
|  | 1 day vs. 30 day | 0.000* | 0.000* | 0.000* |
| Zn ion release | 1 day vs. 7 day | 0.001* | 0.000* | 0.000* |
|  | 7 day vs. 30 day | 0.018* | 0.000* | 0.000* |
|  | 1 day vs. 30 day | 0.000* | 0.000* | 0.000* |

*The mean difference is significant at the 0.05 level.

TABLE 8

Glass solubility statistics (with respect to $Ta_2O_5$ content).

|  |  | TA0 vs. TA1 | TA1 vs. TA2 | TA0 vs. TA2 |
|---|---|---|---|---|
| % weight loss | 1 day | 1.000 | 1.000 | 1.000 |
|  | 7 day | 1.000 | 1.000 | 0.965 |
|  | 30 day | 1.000 | 1.000 | 1.000 |
| pH | 1 day | 1.000 | 0.417 | 0.280 |
|  | 7 day | 0.038* | 0.716 | 0.004* |
|  | 30 day | 0.212 | 0.124 | 0.003* |
| Sr ion release | 1 day | 0.000* | 0.000* | 0.000* |
|  | 7 day | 0.000* | 0.001* | 0.000* |
|  | 30 day | 0.000* | 0.001* | 0.000* |
| Zn ion release | 1 day | 0.001* | 0.005* | 0.000* |
|  | 7 day | 0.000* | 0.000* | 0.000* |
|  | 30 day | 0.000* | 0.000* | 0.000* |

*The mean difference is significant at the 0.05 level.

Considering the former role of $Ta_2O_5$ and its substitution with ZnO in the formulated glasses, the solubility properties were expected to decrease. This assumption can be attributed to the fact that dissolution rates must decrease with additional cross-links formed between the silicate groups and tantalum ions. However, the solubility behavior of the glasses under study showed that water can diffuse into the glass structure causing some cations to release into the surrounding medium, resulting in increased % weight loss and consequently higher pH and ion release profiles. Previous studies [67, 68] have shown that solubility of a glass system strongly depends on the glass composition. It can be generalized that the addition of network modifiers disrupts bonds within the glass network resulting in increased number of NBOs and subsequently increased hydration/solubility when aged in a medium such as water or simulated body fluid. Vice versa, the addition of a glass former results in the formation of additional cross-linking within the glass structure resulting in increased network connectivity, reducing solubility. In this study, the results obtained, while not wishing to be limited by theory, may suggest that increasing the $Ta_2O_5$ content in the formulated silica-based glasses is accompanied by a rapid dissolution of the unstable residual glass phase at the initial stage of the interaction. While not wishing to be limited by theory, this may happen due to the physical and chemical characteristics of Ta. Ta is a basic metal that has a highly reactive surface. The surface of the $Ta_2O_5$ is protected by a thin oxide layer [69], thus preventing its reaction with water. While not wishing to be limited by theory, when $Ta_2O_5$ is incorporated in a bioglass system and soaked in water, Ta acts in the same way as Ca or Sr, meaning that it acts as an unstable residual glass particle. This results in its quick dissolution in the water upon immersing. Further, while not wishing to be limited by theory, the solubility behaviour of the glass system under study may have resulted from the fact that Ta is more electropositive than Zn. According to the generalized solubility rules, the more electropositive the central atom, the more basic the oxide. Ta when compared to Zn is a more electropositive metal that increases pH of the medium in which it is immersed due to its rapid dissolution in the surrounding medium. This initial burst of the cations may, for example, be favorable for both cell viability and osseointegration as well as for fighting against bacterial species.

III. Summary

The work herein has shown that the synthesis of amorphous low $Ta_2O$-containing glasses is possible via the melt-quenching process. The incorporation of up to 0.5 mol % $Ta_2O_5$ at the expense of ZnO resulted in structural changes resulting from the insertion of TaO units into the silicate network. Glass solubility experiments showed that minor amounts of Ta incorporation altered the glass solubility. The ability to control glass solubility by minor compositional modifications is useful for the clinical applications of such bioglasses, for example, where the coordination of material solubility with bone remodelling/formation are of importance.

Example 2: A Bioadhesive Based on Glass Polyalkenoate Cement Chemistry

Ta containing GPCs may, for example provide clinicians with an adhesive for use in sternal fixation and repair. The physical, mechanical and biological properties of new adhesive materials based on Ta-containing GPCs have been characterized to study these materials for sternal fixation and repair.

I. Materials and Methods (a) Glass Synthesis

Three glasses were prepared for this study, a $Ta_2O_5$-free $SiO_2$—ZnO—CaO—SrO—$P_2O_5$ glass (TA0) and two $Ta_2O_5$-containing glasses (TA1 and TA2) where Ta incrementally replaced ZnO in the TA0 parent composition (Table 1). Details on the synthesis and composition of glasses TA0, TA1 and TA2 are provided hereinabove in Example 1 and Table 1. After the annealing step, the glasses were used for subsequent cement preparation and characterization.

(b) Cement Preparation

Cement samples were prepared by thoroughly mixing the annealed glass with poly (acrylic acid) (PAA, Mw, ~213,000 and median particle size <90 µm, Sigma-Aldrich, St. Louis, Mich., USA) and distilled water on a glass plate. The cements were formulated in a powder: liquid (P:L) ratio of 1:1, where 1 g of glass was mixed with 0.50 g PAA 200 and 0.50 ml water. Complete mixing was undertaken within 30 s in ambient room temperature (23±1° C.). These cements are also referred to as (TA0, TA1 and TA2) after the glasses that they were fabricated from.

(c) Evaluation of Setting Characteristics

Working and Net Setting (Hardening) Times:

The working time of the cements was measured in ambient air (23±1° C.) using a stopwatch, and was defined as the period of time from the start of mixing during which it was possible to manipulate the material without having an adverse effect on its properties. The setting time of cements was measured in accordance with ISO 9917-1:2007 for dental based cements. An empty mold with internal dimensions 10 mm×8 mm was placed on aluminum foil and filled to a level surface with mixed cement. Sixty seconds after mixing commenced, the entire assembly was placed on a metal block (8 mm×75 mm×100 mm) in an oven maintained at 37° C. Ninety seconds after mixing, a Vicat needle indenter (mass 400 g) was lowered onto the surface of the cement. The needle was allowed to remain on the surface for 5 s, the indent it made was then observed and the process was repeated every 30 s until the needle failed to make a complete circular indent when viewed at ×2 magnification. The net setting time of the three tests was recorded.

Fourier Transform Infrared (FTIR) Spectroscopic Study:

Three cement cylinders (6 mm high, 4 mm diameter) of each composition were prepared and aged for 1 and 7 days in distilled water. ~0.3 g of powdered versions of each cement (<90 µm) were spread onto NaCl crystal discs of 25 mm diameter. Spectra were collected using a Fourier transform infrared spectrometer (Spectrum One FTIR spectrometer, Perkin Elmer Instruments, USA) and background contributions were removed. The sample and the reference background spectra were collected 16 times for each cement formulation in ambient air (23±1° C.). Analysis was performed in the wavenumber ranging from 900 to 3750 $cm^{-1}$ with a spectral resolution of 4 $cm^{-1}$.

(d) Evaluation of pH and Ion Release

Samples Preparation:

GPC cylinders (6 mm high and 4 mm diameter) were prepared from each glass type for pH testing and ion release studies. Sample solutions were prepared by exposing cylindrical samples (n=3) in calculated quantities (10 ml) of sterile de-ionized (DI) water and incubated (37° C.) for 1, 7 and 30 days.

pH Analysis:

Changes in the pH of solutions were monitored using a Corning 430 pH meter. Prior to testing, the pH meter was calibrated using pH buffer solution 4.00±0.02 and 7.00±0.02 (Fisher Scientific, Pittsburgh, Pa.).

Ion Release Studies:

The ion release profile of each specimen was measured using atomic absorption spectroscopy (AAS) on a Perkin-Elmer Analyst 800 (Perkin Elmer, Mass., USA). AAS calibration standards for Sr and Zn elements were prepared from a stock solution on a gravimetric basis. Three target calibration standards were prepared for each ion and DI water was used as a control.

(e) Evaluation of Mechanical Properties

Determination of Compressive Strength:

The compressive strength ($\sigma_c$) of the three GPC compositions were evaluated in ambient air (23±1° C.) according to ISO 9917-1:2007. Cylindrical samples (n=5) were tested after 1, 7 and 30 days ageing (DI water, 37° C.). Testing was undertaken on an Instron Universal Testing Machine (Instron Corp., Massachusetts, USA) using a ±2 kN load cell at a crosshead speed of 1 mm·$min^{-1}$.

Determination of Biaxial Flexural Strength:

The biaxial flexural strengths (of) of the cements (n=5) were evaluated using the method as described by Williams et al. [70]. Cement discs were tested, in the wet state, after being aged for 1, 7 and 30 days in distilled water in a 37° C. incubator. Testing was undertaken on an Instron Universal Testing Machine (Instron Corp., Massachusetts, USA) using a ±2 kN load cell at a crosshead speed of 1 mm·$min^{-1}$. The fracture strength (N) was noted for each sample. The load cell error was calculated at 0.005% at 50 N to 0.04% at 100 N, within which these test samples fracture.

Determination of Vickers Hardness:

Hardness testing was performed on cement discs (2 mm high, 10 mm diameter) with 10 measurements taken per disc and 3 discs used for each glass composition. Samples were tested after 1, 7 and 30 days immersion in sterile DI water at 37° C. A Shimadzu HMV-2000 micro hardness testing machine (Shimadzu Corporation, Kyoto, Japan) was used. Discs were mounted in epoxy resin and polished using 600 grit silicon carbide polishing paper. Ten Vickers indentations at a load of 500 g and a dwelling time of 15 s were made on each disc. Using the attached light microscope and computer, the diagonals created by the indenter were measured and VHN was calculated using Eq. (2):

$$Hv = 1.854 \frac{F}{d^2} \qquad (2)$$

wherein F is the applied load (kgf) and d is the diagonal length (mm).

(f) Evaluation of Radiopacity

Cement discs (12 mm diameter, 1 mm thick) were prepared and incubated (37° C.) for 1 h. Once removed from their molds, the samples were ground using 1200 grit silicon carbide paper until they were 1 mm thick in accordance with ISO 9917-1:2007 [71]. For the test, the three GPC discs were positioned on dental x-ray film, between an aluminum step wedge (10 steps from thickness from 1.35 mm to 12.62 mm) and an 18 mm thick lead plate. Film was exposed to 70 kV at 7 mA for 0.16 seconds from the X-ray source (Phot-X II, Belmont Equipment, Somerset, N.J., USA). Optical densities were measured using a QAS Densitometer (Picker International, Highland Heights, Ohio, USA). Manipulation of results was completed as per the procedure outlined in ISO9917:2007 part 1.

(g) Antimicrobial Analysis

The antimicrobial properties of the cement discs (10 mm in diameter, 2 mm thick, n=3) were evaluated on agar plates, against both prokaryotic and eukaryotic species. Prokaryotic species involved one Gram-negative bacterium (*Escherichia coli*) and two Gram-positive bacteria (*Staphylococcus aureus* and *Streptococcus epidermidis*) while eukaryotic species involved one fungus (*Fusarium solani*). Bacterial lawns were spread on Tryptic Soy Agar (3 g/L Tryptic Soy Broth, 15 g/L agar). The antimycotic properties of the disks were assessed on Yeast Malt Agar plates (10 g/L Dextrose, 5 g/L Peptone, 3 g/L Malt Extract, 3 g/L Yeast Extract, 15 g/L agar, pH 8.0). All chemicals were purchased from Fisher Scientific (Ottawa, ON, Canada). Bacterial cultures were grown to an exponential phase (12-16 h), diluted in Physiological Saline Solution (9 g/L NaCl) to $10^6$ cells/mL and spread onto TSA. Fungal cultures were grown on YMA for 1 month prior to the experiment, and blocks (1 cm×1 cm) excised from the outside of the radial colony and transferred to the center of the YMA test plate. Antimicrobial properties were quantified on the bacterial lawns by measuring and comparing the zones of growth inhibition, whereas antimycotic properties against the fungal colonies were compared by measuring the radial growth of the culture.

Samples were sterilized by spreading them in sterile petri dishes and exposing them to ultraviolet (UV) light in a biological safety cabinet for 16 hours (Bio Klone 2 Series, Class II, Type A2 Biological Safety cabinet, equipped with one integral UV light, Microzone Corporation, Napean, Ontario, Canada).

One disk of each formulated cement (3 disks per plate) was added to each bacterial and fungal plate, evenly spaced on the lawn or around the central fungal colony. Each plate (3 disks per plate) had a single microbial species, and each species was repeated in triplicate for statistical comparisons. The diameters of the inhibition zones, as well as the diameters of the fungal colonies, were measured (mm) and the means and standard deviations of triplicate samples were compared with independent t-tests.

(h) Cytotoxicity Testing

Cytotoxicity of the cement discs (10 mm in diameter, 2 mm thick, n=3) was evaluated using chondrocytes for up to 7 days in culture. Cement discs were first sterilized by soaking in 70% ethanol overnight, followed by exposure to UV light for 16 hours. Primary bovine articular chondrocytes were then isolated from the metacarpal-phalangeal joints of skeletally mature cattle (12-18 months old) from local slaughter houses by sequential enzymatic digestion. Harvested cartilage slices were incubated in a 0.5% protease (w/v) (Sigma Aldrich Ltd., Oakville, ON, Canada) for 1.5 hours at 37° C. followed by 0.15% collagenase A (w/v) (Sigma Aldrich) for 18 hours at 37° C. Chondrocytes were then separated by passing the digest through a 200-mesh filter (Sigma Aldrich). Viable cells (determined by Trypan dye exclusion [72]) were re-suspended in DMEM culture media without phenol red and supplemented with 10% fetal bovine serum and 1% (2 mM) $_L$-glutamine and then seeded on the surface of the cement substrates at a density of 9500 cells per disc. After 1, 3 and 7 days of culture, cell viability was assessed using a Methyl Tetrazolium (MTT) assay kit (Sigma Aldrich) according to the manufacturer's instructions. As the presence of the cement discs would interfere with the absorbance measurements, aliquots of the precipitate solution (without cells) were analyzed separately. All results were compared to control cultures of the same number of cells seeded directly onto tissue culture plastic.

(i) Ex-Vivo Bond Strength Testing

Figure 13:
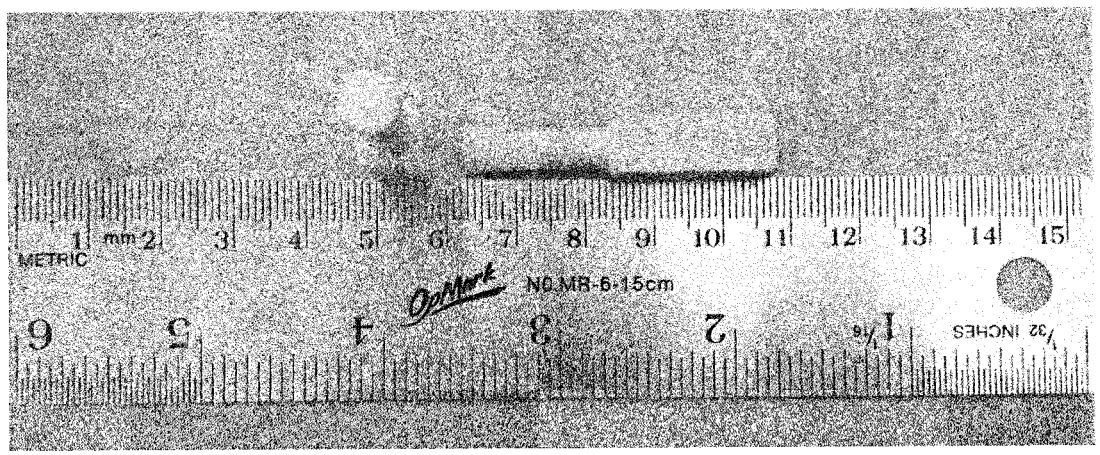
FIG. 13 is a photograph showing a cross-sectional view (left) and side view (right) of a bovine cortical bone sample used for ex-vivo adhesion testing in the examples of the present disclosure. A ruler is provided to show scale.

Samples cut from femur cortical bone and reduced to cylindrical bone samples were utilized to study the ability of the developed materials to adhere to bovine cortical bone. Bone samples were machined to their final geometries using a computer numerical control (CNC) machine (FIG. 13). The dimension of the samples was measured using a caliper. Fresh bone samples shortly after machining were sterilized and then kept in a protector tube at −4° C. Prior to testing, the samples were left for 0.5 h at ambient temperature before applying the adhesive. The adhesive of each material (TA0, TA1 and TA2) was prepared as discussed hereinabove and applied directly on both sides of the bovine bone (n=3). Each sample was held together for one minute to allow for attachment before it was placed in DI water and incubated (37° C., 1 day) prior to testing. Testing was undertaken on an Instron Universal Testing Machine (Instron Corp., Massachusetts, USA) using a ±2 kN load cell at a crosshead speed of 1 mm·min$^{-1}$. The fracture strength (N) was noted for each sample.

(j) Statistical Analysis

A non-parametric Kruskal-Wallis H Test was used to analyze the data. The Mann-Whitney U test was used to compare relative means and to report statistically significant differences when P≤0.05. Statistical analysis was performed on all groups where n≥3. Statistical analysis was performed using SPSS software (IBM SPSS statistics 21, IBM Corp., Armonk, N.Y., USA).

II. Results and Discussion (a) Evaluation of Cement Setting Characteristics

Figure 14:
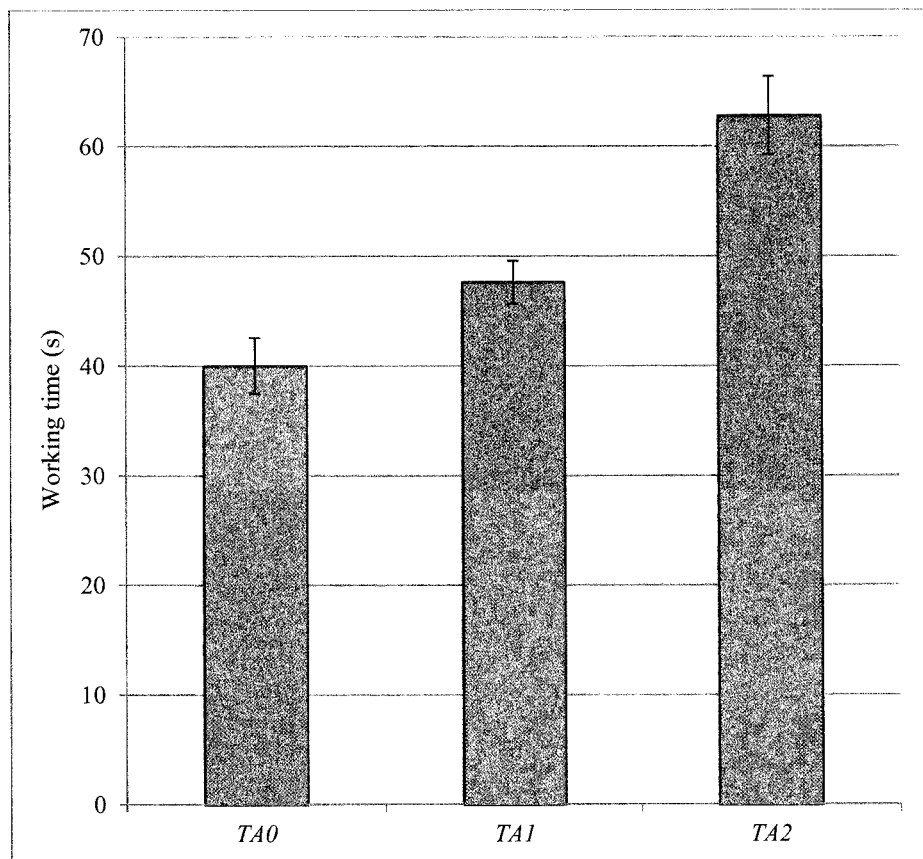
FIG. 14 is a plot showing working times for Ta-containing silica based GPCs TA0 (left), TA1 (middle) and TA2 (right). Error bars represent standard deviation from the mean (n=5).
Figure 15:
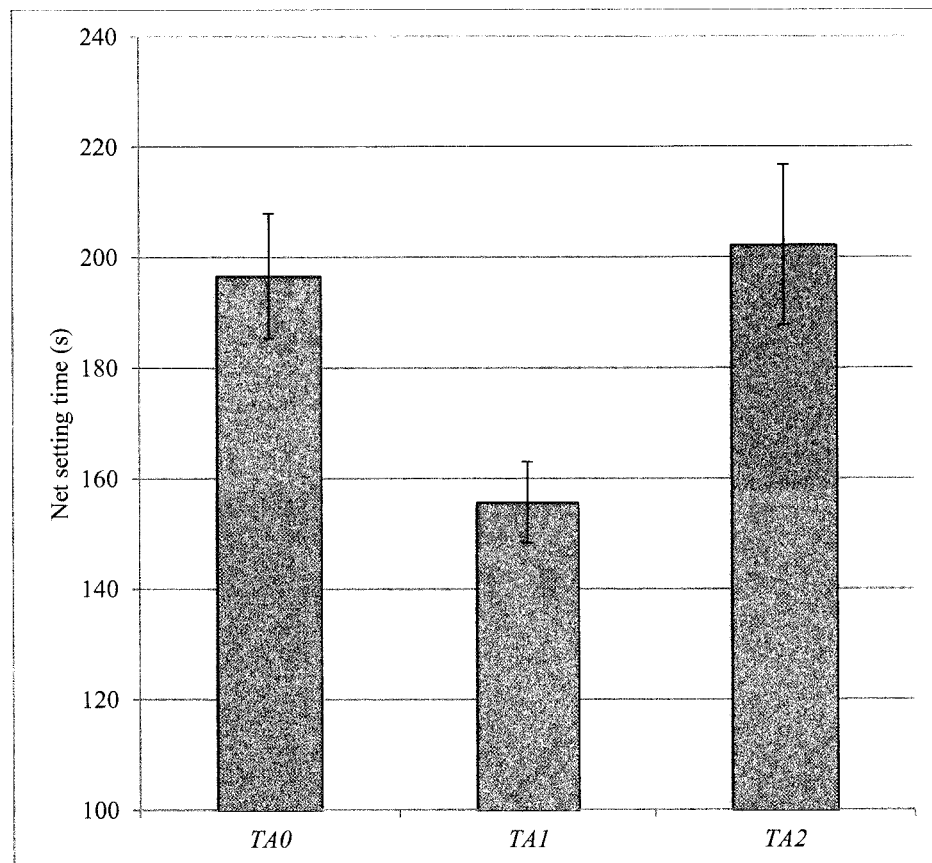
FIG. 15 is a plot showing setting times for Ta-containing silica based GPCs TA0 (left), TA1 (middle) and TA2 (right). Error bars represent standard deviation from the mean (n=5).

Working and Net Setting Times:

The working and setting times of the cement series were evaluated with respect to the increasing concentration of $Ta_2O_5$ in the glass phase, and are presented in FIGS. 14 and 15, respectively. Working times were recorded as 40, 48 and 63 s for TA0, TA1 and TA2, respectively (FIG. 14). The setting times were also recorded (FIG. 15). The $Ta_2O_5$-free GPCs (TA0) presented a setting time of 197 s which decreased significantly to 156 s for TA1 and then increased to 202 s for TA2. The setting chemistry of Ta-containing GPCs has not previously been described in this field. Working and setting times herein were dependent on the concentration of $Ta_2O_5$ incorporated into the glass. The workability of TA0 and TA1 cements is too short to be considered suitable for sternal fixation. However, the workability of TA2 is more suitable for sternal fixation. The setting time of all cement formulations lies within the limits outlined by ISO9917-1:2007 for dental based materials/cements, where a minimum of 90 s and a maximum of 360 s is required [71]. $Ta^{5+}$ acts as a network former by adopting six-fold coordination ($TaO_6$). Zn however may either adopt four-fold coordination in oxygen polyhedron and act as a network former, or adopt six-fold coordination and act as a network modifier [6]. Substituting $Ta^{5+}$ with $Zn^{2+}$ is expected to result in a better glass structure in terms of stability and electro-neutrality. $Ta^{5+}$ provides a larger number of positive charges when compared to $Zn^{2+}$ and therefore acts as a charge-efficient network former. This results in a delay in the gelation process between the COOH groups and $Ta^{5+}$ ions resulting in longer handling times. While not wishing to be limited by theory, the un-expected decrease in the $T_s$ of TA1 can be attributed to the glass particle size, or to slight changes in the glass compositions. The cements with the highest amounts of $Ta_2O_5$(TA2) exhibited longer working times and similar setting times than the $Ta_2O_5$-free GPCs and are advantageous when compared to TA0 and TA1, as clinical materials, for example for use in sternal fixation.

Figure 16:
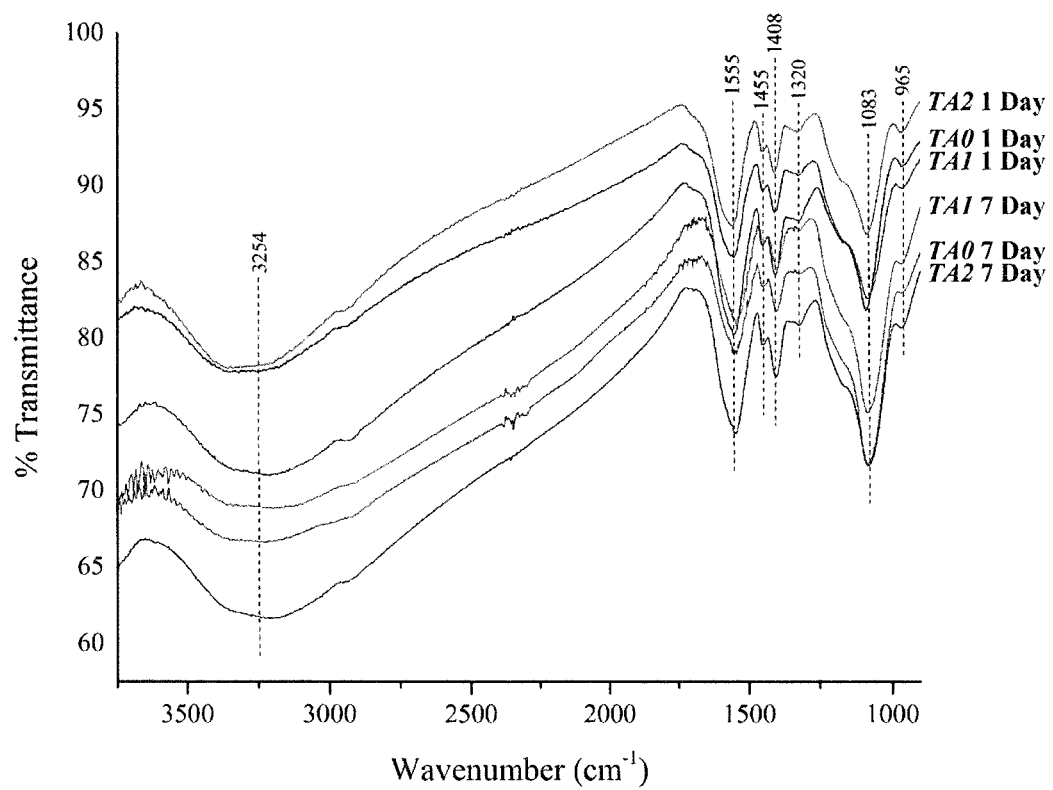
FIG. 16 shows Fourier transform infrared (FTIR) spectra of cement series TA2, TA0 and TA1 over 1 (top three spectra) and 7 days (bottom three spectra), post cement preparation and aging in deionized (DI) water.

FTIR Spectroscopic Study:

FTIR can provide characteristic information on the setting kinetics of GPCs. FTIR transmittance spectra of the cement series, obtained at days 1 and 7, post cement preparation and maturation in DI water, are shown in FIG. 16 in the range 3750-900 $cm^{-1}$. The obtained bands are centered at 3254, 1555, 1455, 1408, 1320, 1083, and 965 $cm^{-1}$. Table 9 shows a complete list of the obtained vibration frequencies and their assignments. The broad peak centered at 3254 $cm^{-1}$ was observed for all spectra and is assigned to the O—H stretch of adsorbed/embedded water within the poly-salt matrix. This O—H peak broadens at 7 days, particularly for TA0 and TA1. However, the peak intensity does not change significantly for TA2 indicating that TA2 retains the absorbed water for longer times, when compared to TA0 and TA1. While not wishing to be limited by theory, this results from the former role of Ta in these materials may indicate that the gelation/hardening reactions within TA2 are longer, resulting in longer setting times. The peaks centered at 1555, 1455, 1408 and 1320 $cm^{-1}$ are assigned to the asymmetric/symmetric stretching vibrations of the carboxyl COO, which could be assumed to be an asymmetrically/symmetrically bonded COO—X molecule, where X represents a possible metal cation. Both COO—$Ca^{2+}$ and COO—$Sr^{2+}$ groups were identified within the range 1630-1540 $cm^{-1}$ and within the range 1490-1460 $cm^{-1}$ [74]. Small shifts to lower wavenumber/frequency were observed for the transmittance bands at 1555, 1455, 1408 and 1320 $cm^{-1}$ with time. This small shift is caused by the increase in cross-linking (bonding) between the dissociated COO— group and metal cations, such as the $Ca^{2+}$, $Sr^{2+}$ and $Zn^{2+}$, to form a metal carboxylate in the cements. Alternatively, while not wishing to be limited by theory, the small shifts in frequency of these bands may suggest the complexation of glass cations to the COOH and the consequent changes within the glass structure, resulting from the insertion of $Ta_2O_5$ within the glass network. This is in good agreement with the literature [34, 75, 76, 77, 78] which also, while not wishing to be limited by theory, suggests that the 1083 $cm^{-1}$ peak represents the Si—O—Si bridges of the cements and as such its relative increase or decrease in intensity correlates to an increase or decrease in the formation of bridging oxygens. While not wishing to be limited by theory, the peak at 1083 $cm^{-1}$ may also represent the Si—O—Ta bridges within the glass structure. The peak at 965 $cm^{-1}$ has been assigned to the Si—OH bridges within the glass network. The peaks obtained from samples matured for 1 and 7 day samples do not show a trend in relation to the $Ta_2O_5$ content, however the TA2 peak was observed at the highest % transmittance (83% t) for 1 day samples. While not wishing to be limited by theory, this may be due to the changes within the glass network in relation to the insertion of $Ta_2O_5$ metallic ions into the silicate network, hence disrupting the network and resulting in longer setting times. The TA2 sample was observed to experience a drop in % transmittance for the 7 day sample (65% t) and, while not wishing to be limited by theory, this may be attributed to the formation of stronger bonds between the glass cations and acidic anions during maturation in DI water indicating that TA2 results in stronger cements upon immersion in a medium such as DI water.

TABLE 9

Characteristic vibration frequencies ($cm^{-1}$) in FTIR spectra of the cement series.

| Infrared band position ($cm^{-1}$) | Peak assignment | Refs. |
|---|---|---|
| 3254 | O—H stretching | [34, 79] |
| 1555-1320 | Asymmetrical COO—X bonding, where X represents a possible metal cation ($Ca^{2+}$, $Sr^{2+}$, $Zn^{2+}$) | [34] |
| 1083 | Si—O—Si/Si—O—Ta stretching vibration | [78] |
| 965 | Si—OH deformation vibration | [78] |

Figure 17:
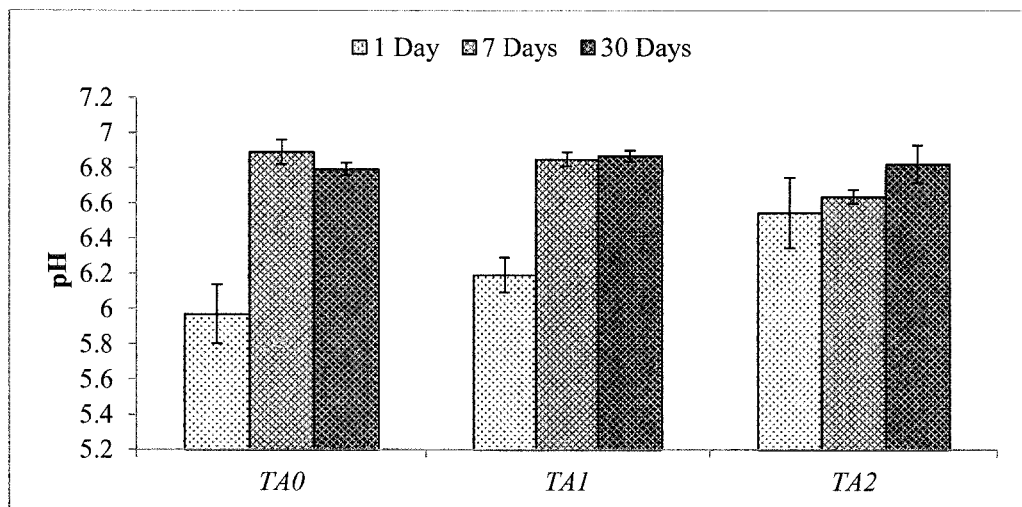
FIG. 17 shows a plot of pH measurements during cement solubility in DI water for 1, 7 and 30 days, post cement preparation. TA0 (left), TA (middle) and TA2 (right). Error bars represent standard deviation from the mean (n=3).

(b) pH and Ion Release Studies pH analysis: The changing pH values of the DI water (pH=6.0) as a function of $Ta_2O_5$ content are plotted in FIG. 17. Comparing TA0 with TA2, there was a significant increase in pH (~6.0-6.6, P=0.000) for 1 day samples, a significant decrease in pH (~6.9-6.6, P=0.000) for 7 day samples and almost identical pH values (~6.82, P=1.000) for 30 day samples. Further, there was no significant difference (P>0.05) in the pH values when comparing TA0 and TA1 for all time intervals. The pH was dependent on immersion time with values varying between ~6 and ~6.9 for all cement formulations. However, slight or no change in pH values (P>0.05) were obtained when comparing 7 and 30 day samples for all cement formulations. When a GPC sample is aged in DI water, hydrogen ions diffuse and dissociate the polycarboxylic chains within the GPC structure and prompt the glass particles to release cations into the environment. This process is controlled by the concentration of hydrogen ions in both the immediate environment (DI water) and the GPC matrix (COOH groups) [80]. In this study, TA2 exhibited the longest working and setting times of the three cement compositions. This resulted in higher pH values, when compared to TA0 and TA1. While not wishing to be limited by theory, the decrease in the pH of TA2 samples at day 7, when compared to that of TA1, indicates that the incorporation of $Ta_2O_5$ facilitates the formation of a stronger network during ageing. Further, identical pH for TA0 and TA2 at day 30 shows that the incorporation of $Ta_2O_5$ at the expense of ZnO does not negatively affect the setting reaction.

Figure 18:
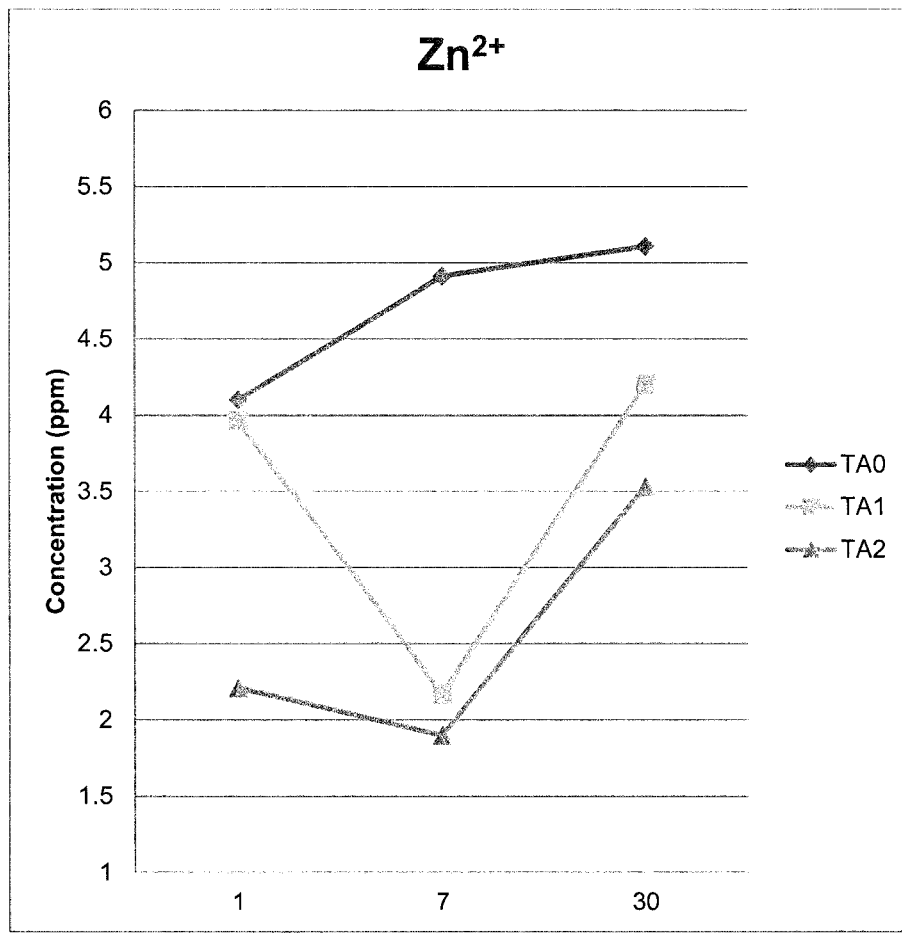
FIG. 18 shows release profiles of $Zn^{2+}$ ions during cement aging in DI water for TA0, TA1 and TA2 samples. Error bars represent standard deviation from the mean (n=3).
Figure 19:
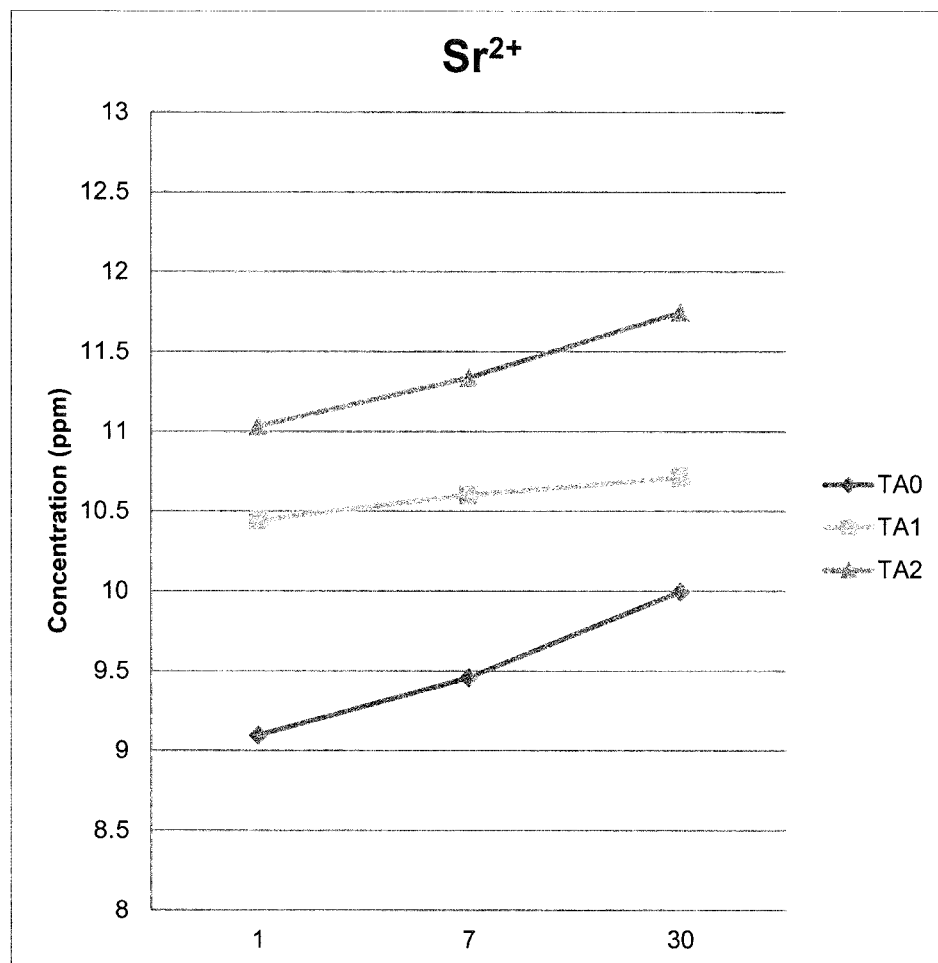
FIG. 19 shows release profiles of $Sr^{2+}$ ions during cement aging in DI water for TA0, TA1 and TA2 samples. Error bars represent standard deviation from the mean (n=3).

Ion release profiles: The changing ion release profiles for $Zn^{2+}$ and $Sr^{2+}$ ions as a function of maturation are plotted in FIGS. 18 and 19, respectively. This study considers the release of $Zn^{2+}$ and $Sr^{2+}$ only due to their content in the precursor glasses and their therapeutic importance in the clinical field. The release of $Zn^{2+}$ decreased with $Ta_2O_5$ content (FIG. 18; Table 10) and was also dependent on immersion time. This was because $Ta_2O_5$ was substituted with ZnO in TA1 and TA2. FIG. 19 and Table 11 show the release of $Sr^{2+}$ ions with both $Ta_2O_5$ content and maturation, peaking at ~11.7 ppm for TA2 cements after 30 days of immersion. Again, while not wishing to be limited by theory, this is attributed to the longer setting reaction of TA2 cements, which retards initial cross-linking after the attack of the PAA on the glass structure. This phenomenon can also be attributed to the slow reaction of the $Ta^{5+}$ ions with the carboxylic groups. Table 10. Release of $Zn^{2+}$ ions over time for the cement series.

TABLE 10

Release of $Zn^{2+}$ ions over time for the cement series.

| | $Zn^{2+}$ concentration (ppm) | | |
|---|---|---|---|
| | 1 Day | 7 Days | 30 Days |
| TA0 | 4.102 | 4.912 | 5.108 |
| TA1 | 3.964 | 2.166 | 4.206 |
| TA2 | 2.212 | 1.898 | 3.532 |

TABLE 11

Release of $Sr^{2+}$ ions over time for the cement series.

| | $Sr^{2+}$ concentration (ppm) | | |
|---|---|---|---|
| | 1 Day | 7 Days | 30 Days |
| TA0 | 9.096 | 9.458 | 9.996 |
| TA1 | 10.442 | 10.602 | 10.712 |
| TA2 | 11.034 | 11.336 | 11.746 |

(c) Evaluation of Mechanical Properties

Figure 20:
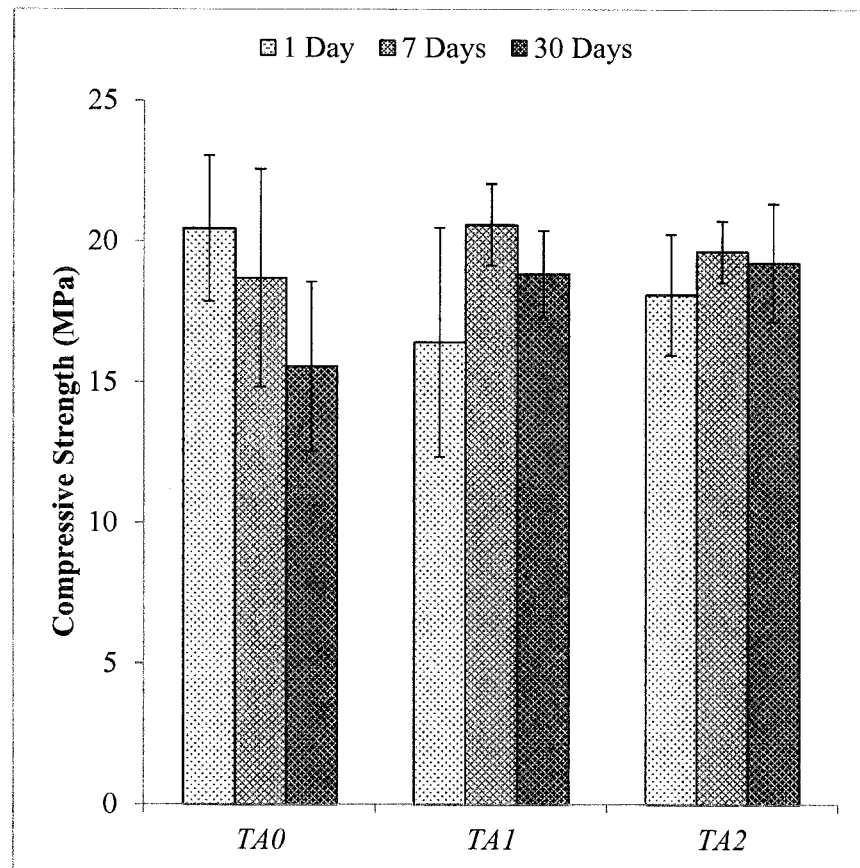
FIG. 20 is a plot of compressive strengths (MPa) of the cement series when aged in DI water for 1, 7 and 30 days. TA0 (left), TA1 (middle) and TA2 (right). Error bars represent standard deviation from the mean (n=5).
Figure 21:
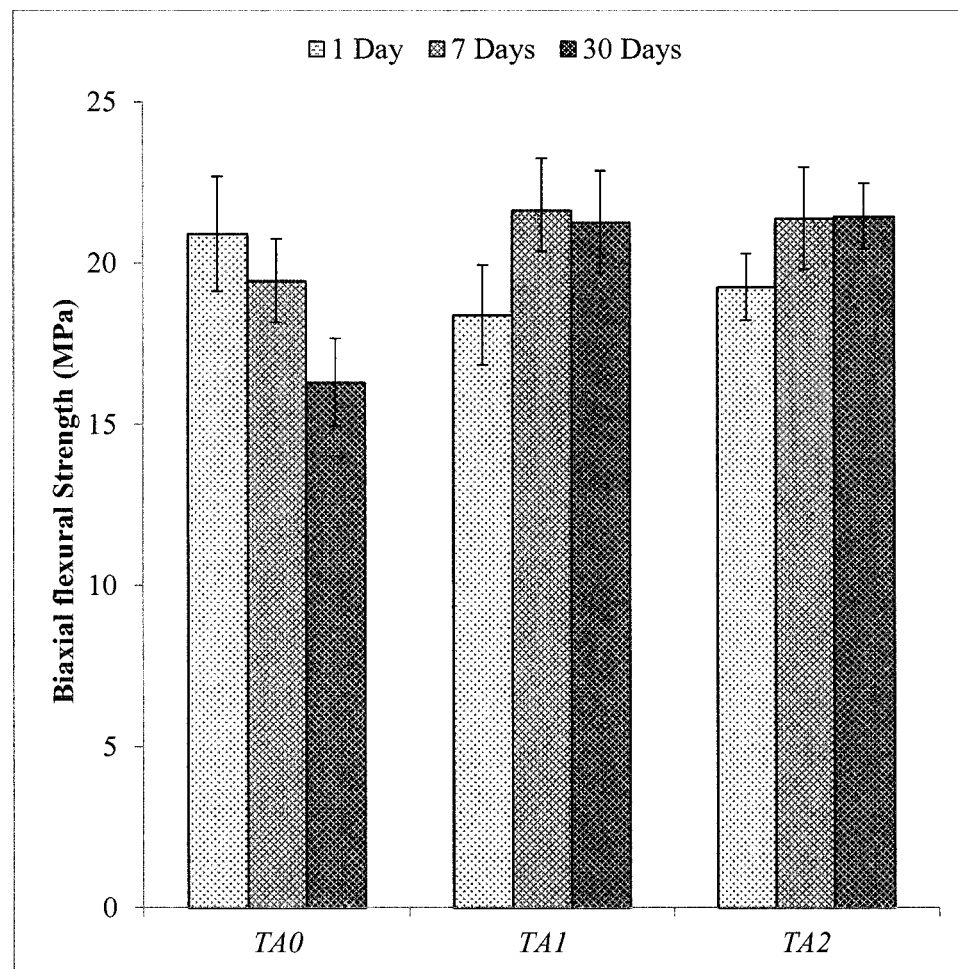
FIG. 21 is a plot of biaxial flexural strengths (MPa) of the cement series when aged in DI water for 1, 7 and 30 days. TA0 (left), TA1 (middle) and TA2 (right). Error bars represent standard deviation from the mean (n=5).

Determination of Compressive and Biaxial Flexural Strengths:

Compressive ($\sigma_c$) and biaxial flexural ($\sigma_f$) strength results of the cement series tested over 1, 7 and 30 days are presented in FIGS. 20 and 21, respectively. The highest $\sigma_c$ and $\sigma_f$ are 21 MPa and 22 MPa, respectively and are obtained for TA1 after 7 days maturation. TA1 had the shortest setting time (FIG. 15) and, while not wishing to be limited by theory, is assumed to have higher strength resulting from the quicker cation-anion reactions within the matrix. However, this behavior was only noted for 7 day results. There was no significant difference (P>0.05) in $\sigma_c$ with respect to either ageing in DI water or $Ta_2O_5$ content in the glass. $\sigma_f$ however, showed variation with respect to both Ta content and maturation. With respect to $Ta_2O_5$ content, there was a significant increase in the $\sigma_f$ (P=0.000) increasing from 16 (TA0) to 21 MPa (TA2), when tested at day 30. With respect to ageing, the $\sigma_f$ of a) TA0 decreased significantly (P=0.001) from 21 (day 1) to 16 MPa (day 30), b) TA1 increased significantly (P=0.029) from 18 (day 1) to 21 MPa (day 30) and c) TA2 increased significantly (P=0.049) from 19 (1 day) to 21 MPa (30 days). The incorporation of Ta has a long-term effect on $\sigma_f$ of the cements prepared from them. While not wishing to be limited by theory, this can be attributed to 1) the slow reactions between Ta and the PAA chains as Ta is impervious to acid attack, 2) the dissolution of the glass particles, i.e. Ta increases the dissolution of the glass particles within the cement matrix resulting in the release of ions that further crosslink PAA chains [81].

Figure 22:
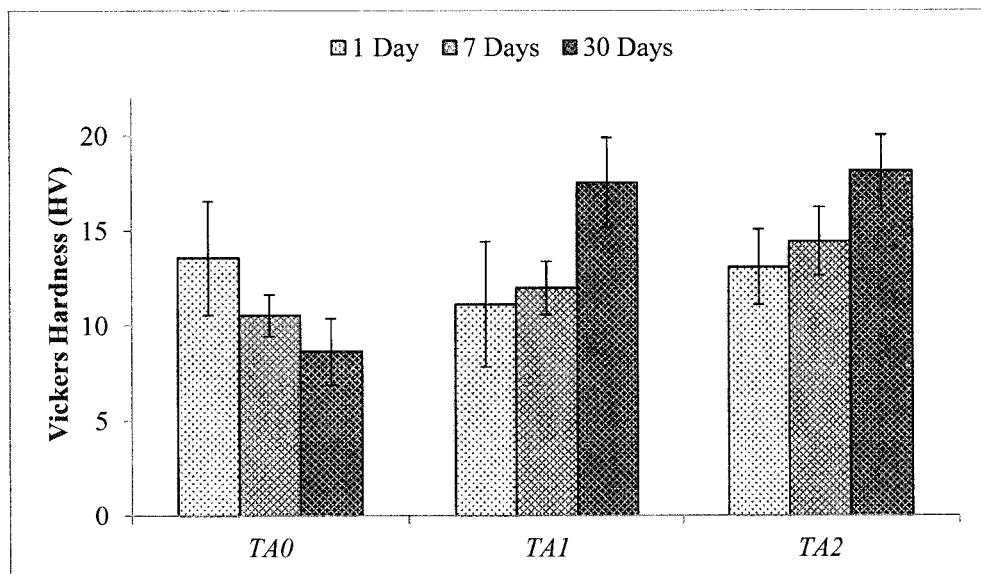
FIG. 22 shows a plot of Vickers hardness (HV) of the cements when matured for 1, 7 and 30 days, post cement preparation. TA0 (left), TA1 (middle) and TA2 (right). Error bars represent standard deviation from the mean (n=5).

Determination of Vickers Hardness:

The Vickers hardness of the cement series is shown in FIG. 22. Hardness varied with $Ta_2O_5$ content and exhibited a similar trend to the compressive and biaxial flexural strength results. Hardness of TA0 decreased with maturation, from 14 to 9 HV. Hardness of TA1 and TA2 however, increased with maturation, from 11 to 18 HV and from 13 to 18 HV, respectively. The incorporation of $Ta_2O_5$ presented higher hardness values and exhibited a significant increase during cement maturation. These results follow the same trend as those of the $\sigma_f$, therefore the $\sigma_f$ discussions, provided above, may hold true for the hardness results.

(d) Evaluation of Radiopacity

Figure 23:
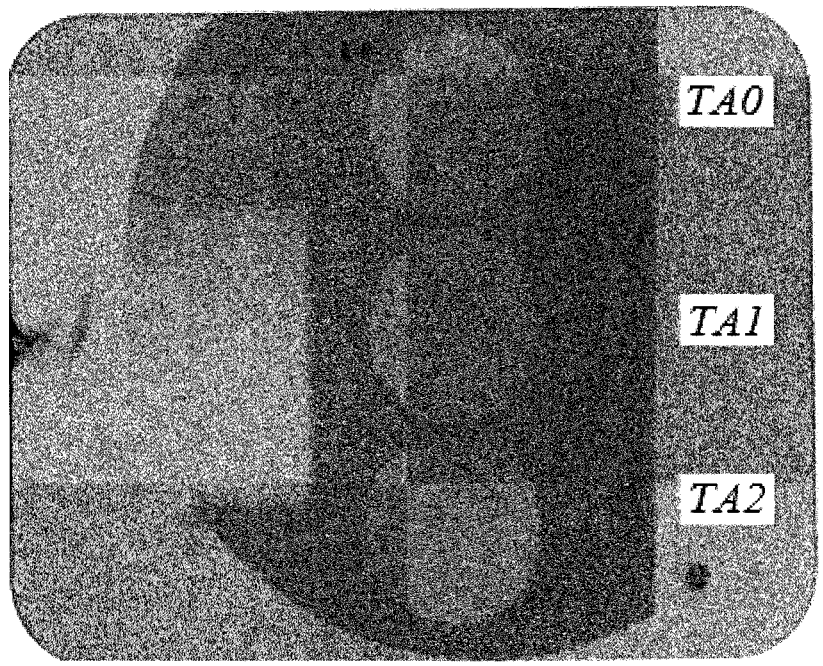
FIG. 23 shows radiographic images of cement discs (right hand side of image, from top to bottom: TA0, TA1 and TA2) and an aluminum step wedge (left hand side of image).
Figure 24:
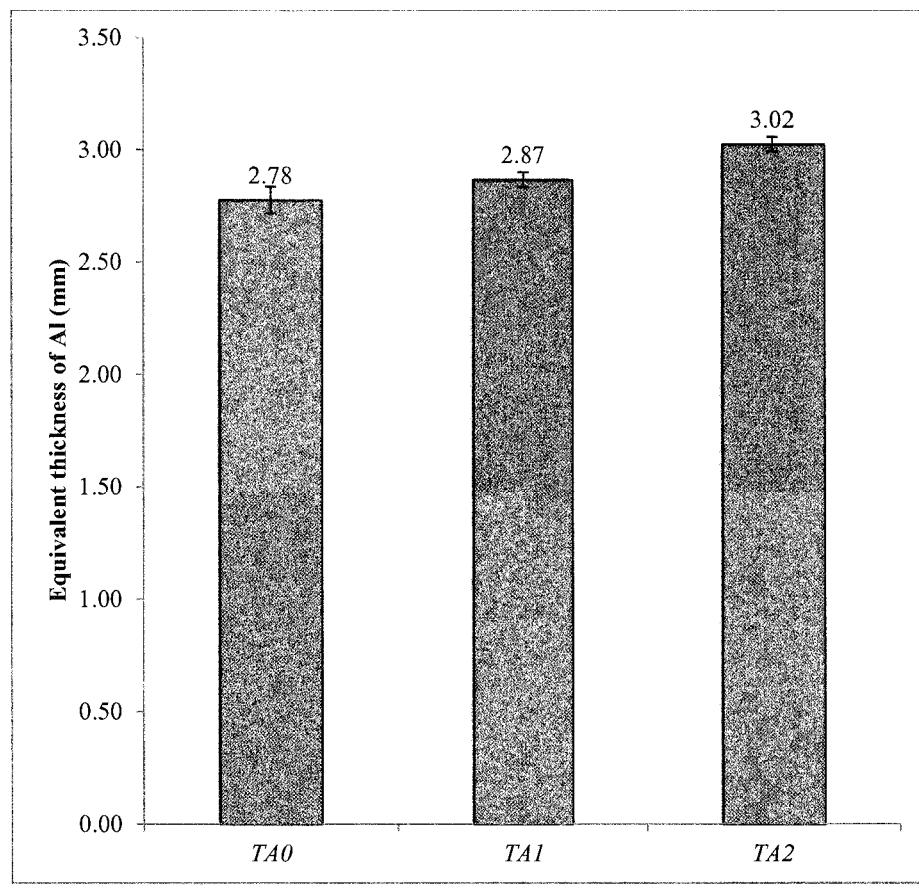
FIG. 24 is a plot showing the radiopacity of the discs of FIG. 23 recorded in mm aluminum (Al), from left to right: TA0, TA1 and TA2. Error bars represent standard deviation from the mean (n=5).

Radiopacity results are shown in FIG. 23 and FIG. 24. All cements exhibited radiopacity higher than that of aluminum (280%, 290% and 300% of that of aluminum for TA0, TA1 and TA2, respectively). TA2 was the most radiopaque cement tested while the $Ta_2O_5$-free cement (TA0) had a similar radiopacity (P>0.05), when compared to that of TA2. The materials developed in this study are more radiopaque than the Zn-GPCs previously produced [31]. The high radiopacity of Zn-based cements was previously attributed to both the ZnO and SrO content [82, 83]. Here, it can be seen that replacing the ZnO with the $Ta_2O_5$ has increased radiopacity, while not wishing to be limited by theory, presumably because $Ta_2O_5$ (8.2 g/cm$^3$) is more radiopaque than ZnO (5.61 g/cm$^3$) [84]. Increased radiopacity allows for easier subcutaneous monitoring of the implant.

(e) Antimicrobial Evaluation

Figure 25:
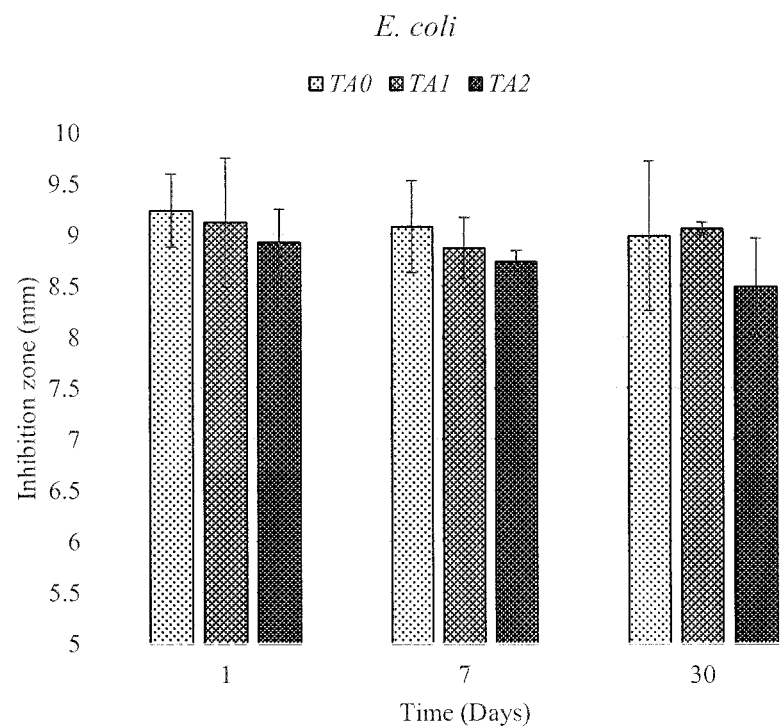
FIG. 25 is a plot of inhibition zones (mm) of *Escherichia coli* lawns on agar media, in response to TA0, TA1 and TA2, evaluated after 1, 7 and 30 days maturation and incubated at 37° C. Error bars represent standard deviation from the mean (n=3).
Figure 26:
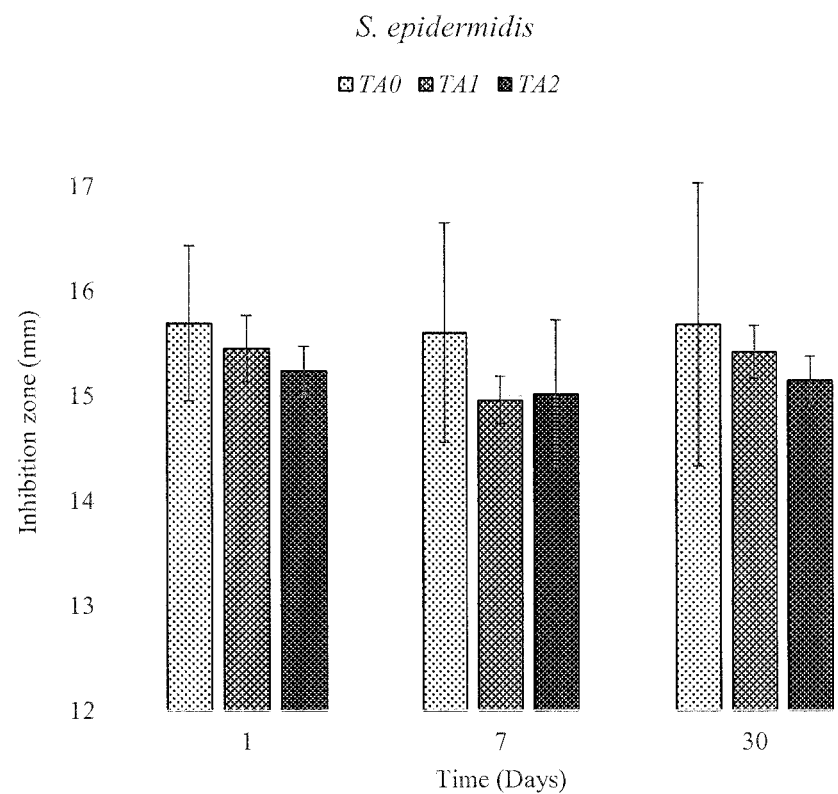
FIG. 26 is a plot of inhibition zones (mm) of *Staphylococcus epidermidis* lawns on agar media, in response to TA0, TA1 and TA2, evaluated after 1, 7 and 30 days maturation and incubated at 37° C. Error bars represent standard deviation from the mean (n=3).
Figure 27:
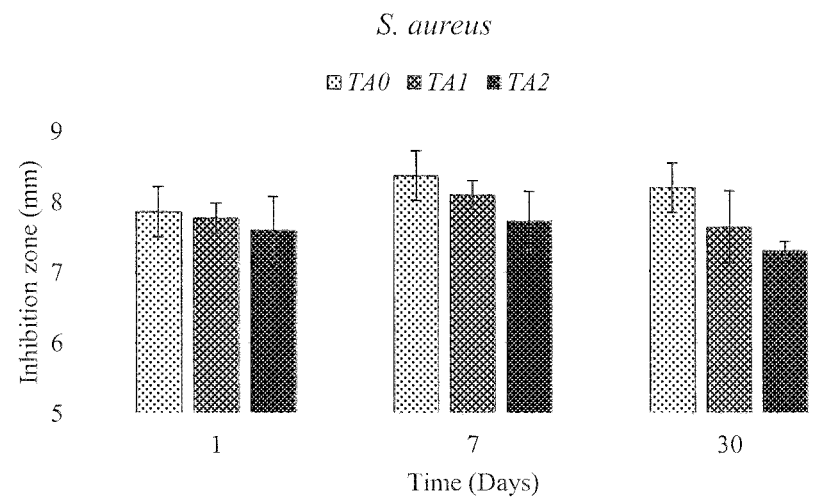
FIG. 27 is a plot of inhibition zones (mm) of *Staphylococcus aureus* lawns on agar media, in response to TA0, TA1 and TA2, evaluated after 1, 7 and 30 days maturation and incubated at 37° C. Error bars represent standard deviation from the mean (n=3).

The antimicrobial properties of Ta-containing GPCs were assessed against both Gram-negative and Gram-positive prokaryotes (FIG. 25, *E. coli*; FIG. 26, *S. epidermidis*; FIG. 27, *S. aureus*), as well as eukaryotes (FIG. 28, *F. solani* at 1 day; FIG. 29, *F. solani* at 7 days; FIG. 30, *F. solani* at 30 days). All GPCs exhibited a level of both antibiotic and antimycotic activity within these experimental parameters.

Within the GPCs assessed in this study, ZnO was substituted with $Ta_2O_5$ (increasingly in TA0, TA1 and TA2; see Table 1 and FIG. 18), and lower levels of antimicrobial activity were thus predicted, since the Zn ion is renowned for its antibiotic effect, whereas Ta is considered less biotoxic [41, 85]. However, the inhibition effect was comparable (P>0.05) with respect to increasing $Ta_2O_5$ content for all bacterial species under study. Similar inhibition zones (8-9 mm±0.4) were obtained for one Gram-positive (*S. aureus*) and one Gram-negative (*E. coli*) strain, while a second Gram-positive bacterium (*S. epidermidis*) was even more susceptible to ion release by the GPCs, with an inhibition zone almost twice as large as the first two strains (15 mm±0.6). This species-dependent activity is in agreement with the literature
, which indicated that factors influencing bacterial proliferation on a material surface are dependent on both the properties of the surface and the bacterial strain, particularly with regards to cell wall composition. It was reported by Wren et al. [87] that $Zn^{2+}$ is particularly inhibitory against *E. coli*, and was thus the ion of interest in this study.

However, as mentioned above, increasing levels of $Ta_2O_5$, accompanied by decreasing levels of ZnO, did not demonstrate any observable influence on the antibiotic properties of the GPCs against any of the bacterial strains of interest. While not wishing to be limited by theory, the uniform antibacterial effect of the materials under study may be attributed to 2 properties: (1) the increased release of Sr (see FIG. 19) with the increased amount of $Ta_2O_5$ (and decreasing amounts of ZnO), and/or (2) the increased wettability of the surface of Ta-containing materials, when compared to Ta-free GPCs. Sr is another ion with reported antimicrobial impact [88] and, although incorporated into the GPCs at the same level in TA0, TA1 and TA2, it is released at increasing levels with higher $Ta_2O_5$ levels due to structural changes in the glass. Thus, while not wishing to be limited by theory, the increasing antimicrobial activity of Sr may offset the decreasing antimicrobial activity of Zn, with the increased incorporation of Ta in the GPCs. It was reported that Ta surfaces result in lower contact angles, higher surface energy and improved antibacterial effect when compared to Ti or HA surfaces, and thus, while not wishing to be limited by theory, Ta itself may have indirect antimicrobial effects as well [89, 90, 91].

During ageing, the antibacterial effect exhibited by these cements was expected to decrease as a result of the continuous cross-linking within the matrix [34], and due to potential time- and morphology-dependent adaptation of microbial species [92, 93]. However, the materials under study have shown that the initial antibacterial effect, while not wishing to be limited by theory, presumably from ions leached into the agar, persisted for up to 30 days with no significant change ($P>0.05$) when compared to day 1.

Figure 28:
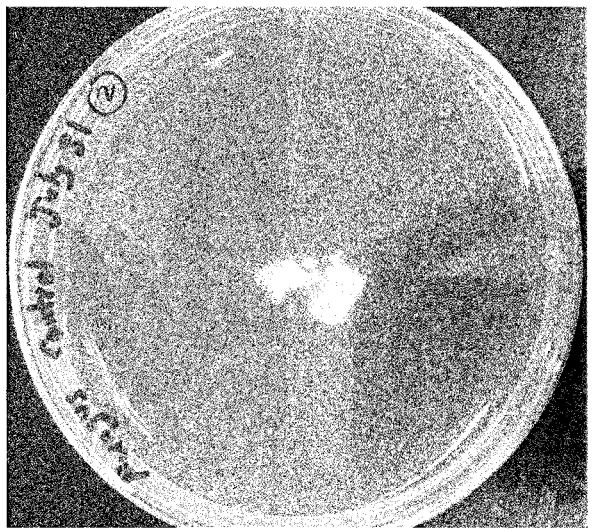
FIG. 28 shows photographs of colony morphology of *Fusarium solani* fungus aged with no samples (control; top image) and tested with TA0, TA and TA2 over a period of 1 day (bottom image).
Figure 28:
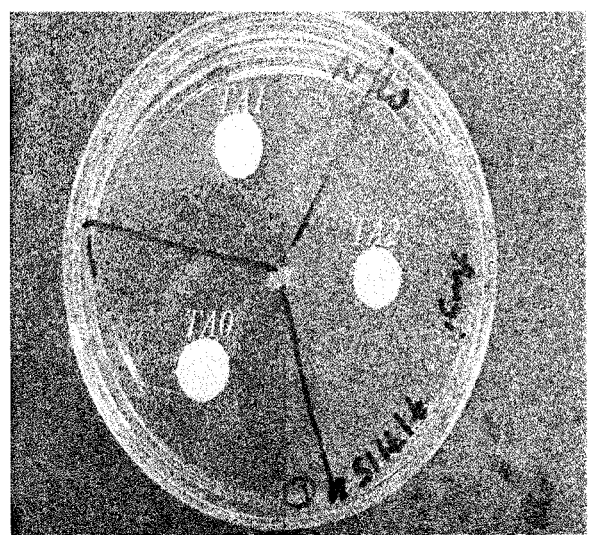
Figure 29:
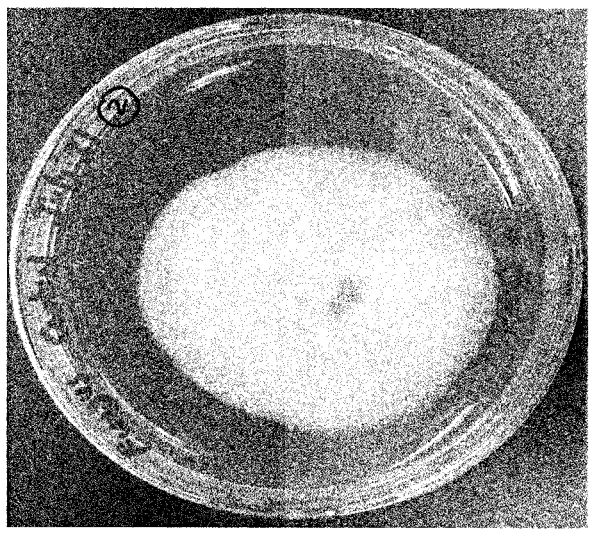
FIG. 29 shows photographs of colony morphology of *Fusarium solani* fungus aged with no samples (control; top image) and tested with TA0, TA1 and TA2 over a period of 7 days.
Figure 29:
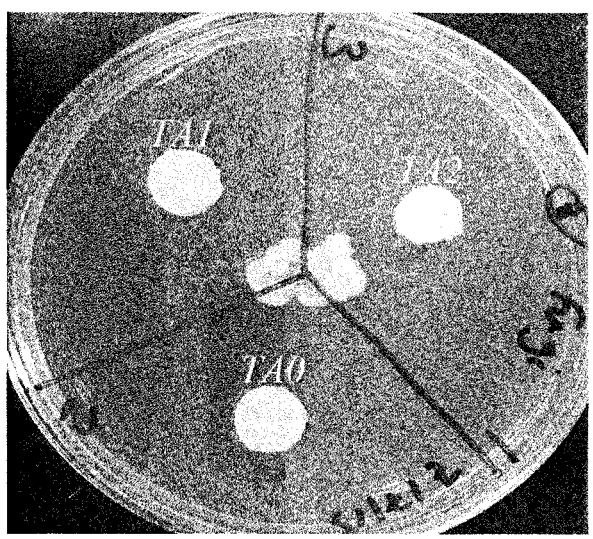
Figure 30:
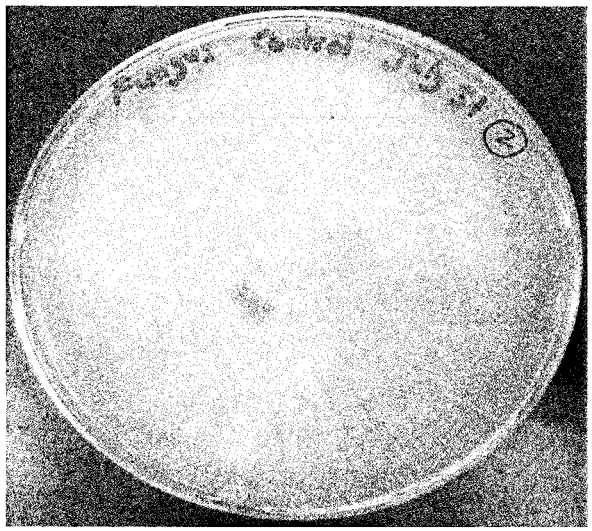
FIG. 30 shows photographs of colony morphology of *Fusarium solani* fungus aged with no samples (control; top image) and tested with TA0, TA1 and TA2 over a period of 30 days.
Figure 30:
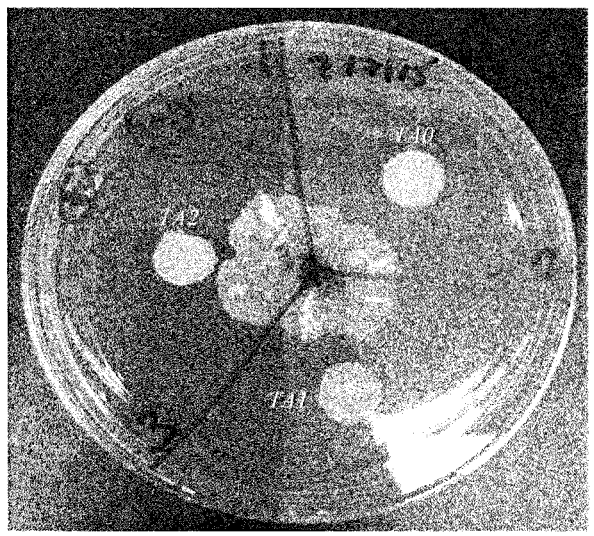

A single fungal eukaryotic strain, *Fusarium solani*, was chosen to explore the antimycotic properties of the GPCs and the results are presented in FIGS. 28-30. A control square fungal colony (3.6×7.2 mm; sourced from the edges of a week-old colony) was transferred onto an agar plate, and its growth monitored over a period of 30 days. At day 1 (FIG. 28; top image), the hyphal colony started to grow outward (14.4×8.6 mm). At day 7 (FIG. 29; top image), the control colony exhibited circular flat shape with a diameter of 52 mm. At day 30 (FIG. 30; top image), the control colony had extended prolifically to a diameter of 73 mm. Similarly, a flat square inoculum block (3.6×7.2 mm) was tested, with the cement substrates (TA0, TA1 and TA2) placed on the surface of the agar plate at equal distances from the central colony. At day 1, day 7 and day 30 (bottom image in FIGS. 28, 29 and 30, respectively), fungal growth and colony morphology was clearly influenced by exposure to the GPCs, as compared to the control. At day 7 (FIG. 29; bottom image), the colony was confined to the center of the plate, growing upward in a raised circular shape, morphologically distinct from the control, with a diameter of 12.5 mm; approximately 20% of the diameter of the control at day 7. At day 30 (FIG. 30; bottom image), colony morphology was similarly influenced by the presence of the GPCs, constrained at 10.6, 2.5 and 4.6 mm away from the center of TA0, TA1 and TA2, respectively. According to the inventors' knowledge, until now, no detailed studies have been disclosed that assess the antifungal performance of GPCs or Ta-containing GPCs. It is clear from the results obtained that the formulated GPCs have antifungal properties. The antifungal properties were shown to (1) decrease with increasing Ta content (and increasing Zn content), and (2) decrease with maturation. While not wishing to be limited by theory, this behavior may be attributed to decreasing the Zn content (FIG. 18) and to the decreasing release of ions with ageing. However, after in-vivo placement of GPCs, any decreasing antimicrobial properties with age should accompany an improvement in immune response/reaction with the healing process, since the skin itself acts as a physical antibiotic barrier during the healing process [94]. Thus, the initial antimicrobial activity is of greatest use. In contrast to the antibacterial observations, increased release of Sr, associated with increasing the Ta content, did not compensate for the decreased release of $Zn^{2+}$, therefore $Sr^{2+}$ is not as antifungal as $Zn^{2+}$. Despite some variation, it can be seen that the formulated cement substrates have clear antibacterial and antifungal activity.

(f) Cytotoxicity Testing

Figure 31:
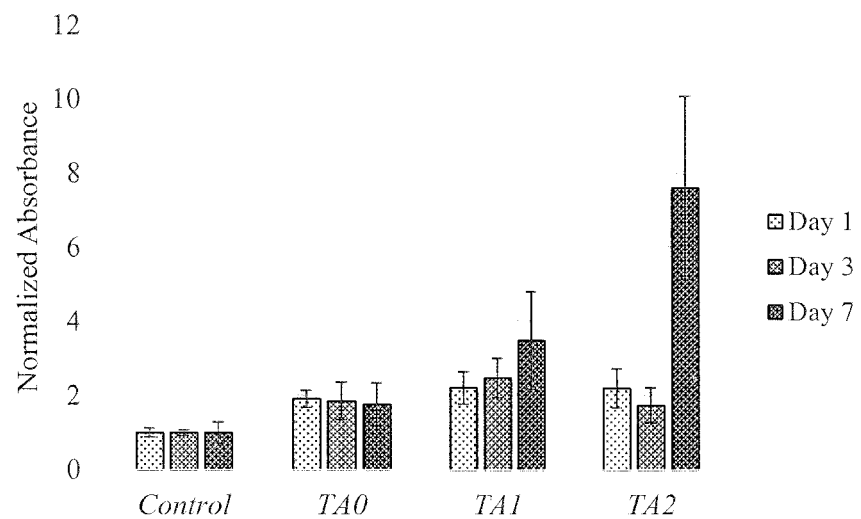
FIG. 31 is a plot showing cell viability results of control fibroblast cells (far left) and the formulated cements (TA0, second from left; TA1, second from right; TA2, far right) over 1, 3 and 7 days, post cement preparation and incubation. Error bars represent standard deviation from the mean (n=3).

FIG. 31 shows the cell viability results of each of the materials tested after 1, 3 and 7 days of culture, compared to chondrocytes seeded on tissue culture plastic (Control). All cements tested did not appear to display any cytotoxic effects as cells appeared to proliferate when cultured on the material surfaces. Cell viability on the TA0 surfaces changed little ($P>0.05$) with culture time reducing from 191% of control (day 1) to 176% (day 7). While not wishing to be limited by theory, this behaviour could be attributed to the ion release products from the cement. Immediately after cell seeding and during the first 24 hours of culture, the cement releases some of its 'unbound' cations at different rates [95]. The release of Si, Sr, Ca, P and Sr ions would be expected to stimulate biological responses such as cell attachment and proliferation [96]. TA1 cements were similar with cell viability ranging between 221% and 349% with no apparent influence of culture time ($P>0.05$). TA2 cements performed differently than the other cements with cell viability ranging between 174-220% (day 1-3) and then increasing to 760% (day 7). While not wishing to be limited by theory, the substitution of $Ta_2O_5$ for ZnO may be responsible for the observed proliferative effect. Cell attachment and proliferation are primarily associated with a material's surface properties such as wettability and the material's bulk/volume composition [41]. An in-vitro study has shown that human osteoblast cells exposed to Ta and HA coatings exhibit equally excellent cellular adherence and viability [97] due to the lower contact angles and higher surface energy of Ta when compared to Ti or HA surfaces [98, 99]. Therefore, Ta incorporation into bioactive glasses may not only stimulate osseo-integration but also their cell-material interactions and long-term mechanical stability. This is supported by a previous in-vivo study of bioactive glass coatings on Ti plates which resulted in enhanced initial tissue attachment, bone growth and rapid osseo-integration [100].

(g) Ex-Vivo Bond Strength Testing

Figure 32:
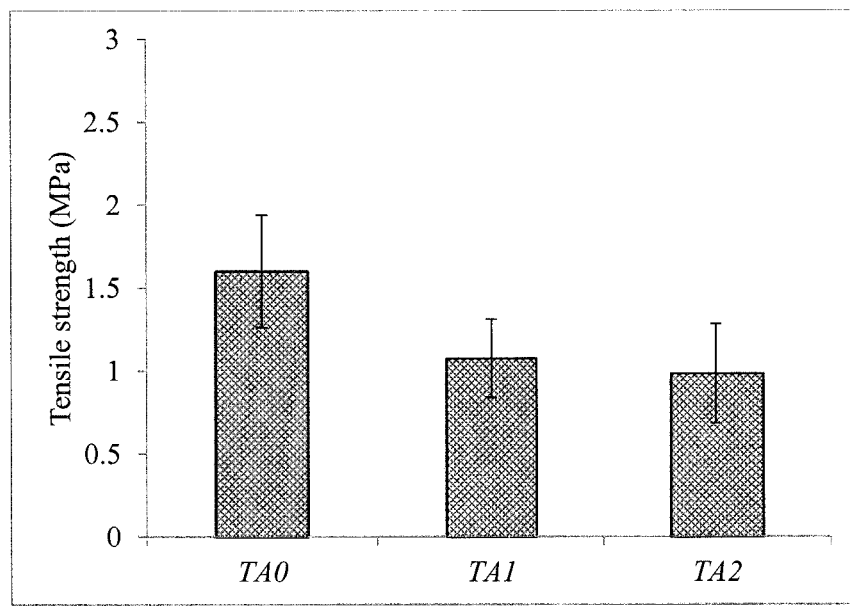
FIG. 32 is a plot showing mechanical testing results for tensile strength (MPa) of bovine femur cortical bones adhered using the formulated cements and aged in DI water for 1 day at 37° C. From left to right: TA0, TA1 and TA2. Error bars represent standard deviation from the mean (n=3).

A preliminary adhesion test was conducted to evaluate the bond strength of the adhesive materials, when applied to bovine femur cortical bone. FIG. 32 shows the tensile strength results obtained at day 1, post sample preparation and incubation. TA0 had the highest strength (1.6 MPa). However, comparable results ($P>0.05$) were obtained for TA1 (1.1 MPa) and TA2 (1.0 MPa) samples. The adhesion and tissue bonding of sternal fixation devices are useful for satisfactory performance. The results of this preliminary study are in line with the mechanical testing results discussed hereinabove. Generally, it was observed that the Ta-containing and Ta-free cements result in comparable strength values at day 1. While not wishing to be limited by theory, comparable results are attributed to the little change in the former glass materials (Table 1). This means that further incorporation of Ta into GPCs may have unfavorable effect on their early strength values resulting from the slow reactivity of Ta with PAA. As discussed above, Ta is impervious to acid attack at the early stage of the reaction, therefore affecting the cation-anion chelating reactions. This however, changes during cement ageing allowing for improved adhesion and mechanical stability. Accordingly, these results suggest that the cements containing the amounts of Ta studied herein have the above-described advantages of Ta but retain the strength of the corresponding cements which do not contain Ta.

III. Summary

The results of this Example suggest that cements based on the tantalum-containing glasses studied herein have the rheology, strength, radiopacity, and antibacterial and in-vitro behavior useful for sternal fixation. This Example has also shown the ability of the formulated materials to adhere to bovine femur cortical bone. When used, for example, as a permanent implant, the formulated adhesives can, for example, be used in conjunction with sternal cable ties to offer additional fixation and/or reduce post-operative complications such as bacterial infections and/or pain from sternal displacement.

Example 3: Effect of $Ta_2O_5$ and $Nb_2O_5$ Content on Setting Time of Cements

I. Materials and Methods

Table 12 presents the glass compositions used in the present Example. TA0 is a tantalum-free glass whereas TA3 to TA6 contain incrementally increasing amounts of Ta at the expense of Zn. NB1 has the same composition as TA3 except with Nb instead of Ta.

TABLE 12

Composition of glass series of Example 3 in mol %.

| Oxide | TA0 | TA3 | NB1 | TA4 | TA5 | TA6 |
| --- | --- | --- | --- | --- | --- | --- |
| $SiO_2$ | 48.0 | 48.0 | 48.0 | 48.0 | 48.0 | 48.0 |
| ZnO | 36.0 | 34.0 | 34.0 | 32.0 | 30.0 | 28.0 |
| CaO | 6.0 | 6.0 | 6.0 | 6.0 | 6.0 | 6.0 |
| SrO | 8.0 | 8.0 | 8.0 | 8.0 | 8.0 | 8.0 |
| $P_2O_5$ | 2.0 | 2.0 | 2.0 | 2.0 | 2.0 | 2.0 |
| $Ta_2O_5$ | 0.0 | 2.0 | 0.0 | 4.0 | 6.0 | 8.0 |
| $Nb_2O_5$ | 0.0 | 0.0 | 2.0 | 0.0 | 0.0 | 0.0 |

Each glass composition in Table 12 (un-annealed) was mixed with the poly(acrylic acid) PAA200 (PAA, Mw, ~213,000 and median particle size <90 μm, Sigma-Aldrich, St. Louis, Mich., USA) and distilled water on a glass plate. The cements were formulated in a powder: liquid (P:L) ratio of 1:1, where 1 g of glass was mixed with 0.50 g PAA200 and 0.50 ml water.

II. Results and Discussion

Results showed that TA0 had a working time of about 20 seconds and set very fast (90 seconds). These times were shorter than those for the TA0 material of Example 2 as the glass compositions used for the preparation of those cements were annealed, which hardens the glass surface thus slowing down its reaction with the acid chains. The Ta-containing glasses showed a rapid increase in the setting and working times, which increased with increasing Ta content). For example, TA3 had a working time of around 20 minutes and a setting time of 1 day and TA6 had a working time of 45 minutes and a setting time of around 3 days. Ta-containing glasses (Table 12) dissolved in water after they set and therefore were not suitable as adhesives for sternal fixation. Mixing the glass with acid and water at different ratios was also attempted. However, the setting time in all trials was too long to be useful for orthopedic applications. For example, a useful setting time for sternal fixation may be up to about 20 minutes or up to about 1 hour. For example, a useful setting time for injectable cements may be longer, for example, up to about 3 hours. In contrast, the Ta-containing glasses of Example 1 did not dissolve in de-ionized water, and resulted in properties favorable for sternal fixation (Example 2).

Niobium pentoxide was also incorporated at 2 mol % into the glass composition to investigate the rheological properties of the resulting cements. The niobium-containing cements had very long working and setting times (very similar to the corresponding Ta cements prepared from glass compositions containing 2 mol % $Ta_2O_5$). While not wishing to be limited by theory, glasses and cements prepared with 0.2 or 0.5 mol % $Nb_2O_5$ are predicted to have similar properties to the corresponding Ta glasses and cements due to the similarities in chemical and physical properties between these two elements therefore glasses containing similar amounts of $Nb_2O_5$ may also be useful in the preparation of niobium-containing cements that have rheological properties suitable for orthopedic applications.

Example 4: Percutaneous Upper Extremity Fracture Fixation Using the Bioglass-Containing Cement Adhesive TA2

This study investigated percutaneous fracture fixation using the injectable glass-based bone adhesive ITA2.

I. Methods (a) Bioglass Synthesis

The glass composition TA2 was used for this study (Table 1). The glass was prepared by weighing out appropriate amounts of the analytical grade reagents (Fisher Scientific, Ottawa and Sigma-Aldrich, Oakville, Canada) and mixing them in a container. Platinum (Pt) crucibles and a Lindberg/Blue M model furnace (Lindberg/Blue M, Asheville, N.C. USA) with a UP-550 controller were used to melt the powders (1650° C., 1.5 hours). The melt was subsequently shock quenched in water to obtain frit which was then dried in an oven (100° C., 1 h), and ground using a ball mill (400 rounds per minute, 15 min). The resulting powder was sieved to collect the <45 μm particles which were utilised for subsequent cement preparation. Further discussion of the glass can be found in Example 1, hereinabove.

(b) Injectable Cement Preparation

Injectable cement samples (ITA2) were prepared by mixing the glass with poly(acrylic acid) (PAA35, $M_w$=50,000, Advanced Healthcare Ltd., Tonbridge, UK) and de-ionized (DI) water on a glass plate at a powder-liquid ratio (P:L) of 1:4, where 1 g of glass was mixed with 2 g PAA and 2 g DI water to create a paste. Complete mixing was achieved within 30 s at ambient room temperature (23±1° C.). The cement was transferred, using a spatula, to a 10 ml syringe and then injected into the fracture site.

(c) Wrist Fixation

Figure 33:
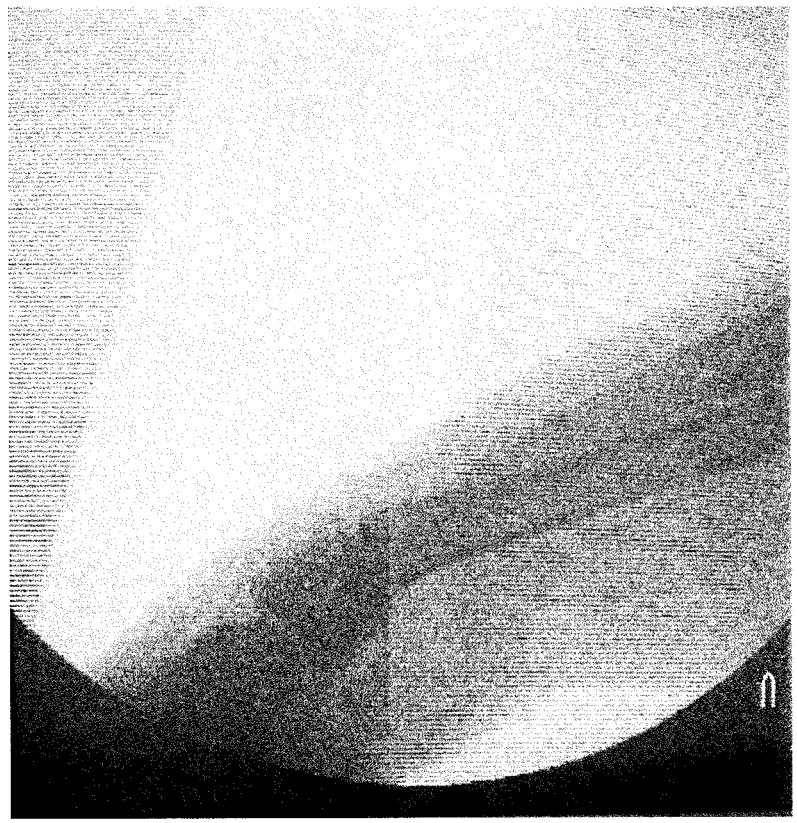
FIG. 33 shows a lateral view of distal radius with osteotomy according to an example embodiment of the disclosure.
Figure 34:
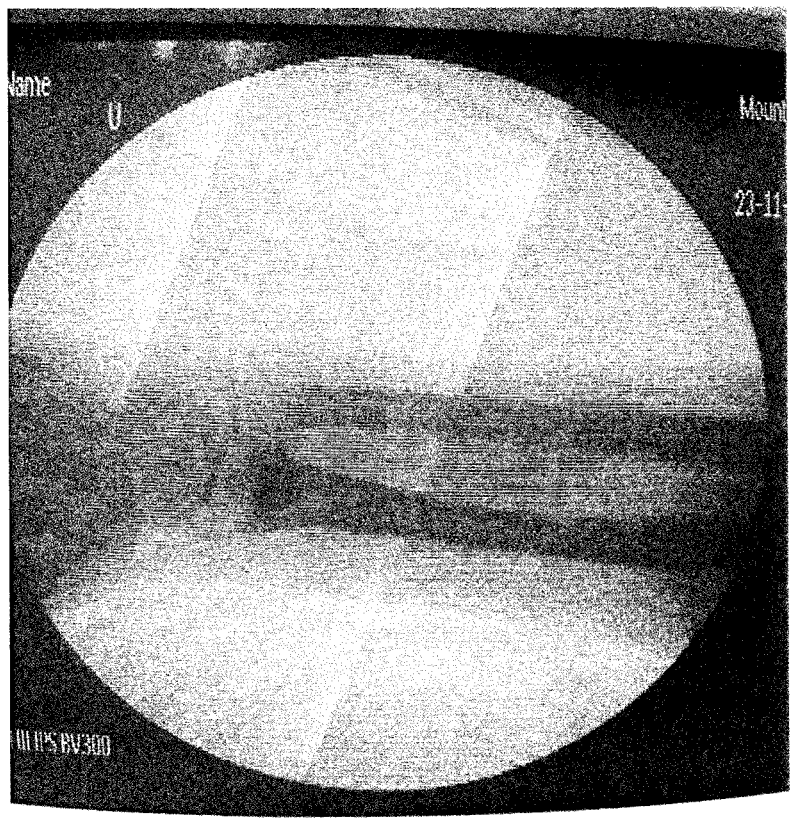
FIG. 34 shows an anteroposterior (AP) view of a distal radius after an injectable cement adhesive prepared from a glass comprising 0.5 mol % $Ta_2O_5$(ITA2) was injected percutaneously according to an example embodiment of the disclosure.

Two right-sided adult upper extremity cadaveric specimens were obtained from the Anatomy Department (University of Toronto, Canada). A percutaneous stab incision through the dorsum of the wrist was used to introduce a ¼ inch osteotome (FIG. 33). A distal radius fracture was simulated and manual force was used to create complete displacement and dorsal angulation. The fracture was verified using biplanar fluoroscopy. Under fluoroscopic guidance, the fracture was reduced with in line longitudinal manual traction. Through the stab incision, 5 cc of the ITA2 cement adhesive was injected into the fracture site using a 16 gauge needle under fluoroscopic guidance. Traction was maintained for 5 minutes. The adhesive was allowed to set for 1 hour. Fluoroscopy was used to verify fracture stability. Soft tissue dissection was then performed to observe adhesive distribution. FIG. 34 shows an anteroposterior (AP) view of distal radius after adhesive applied percutaneously.

(d) Proximal Humerus Fixation

Figure 35:
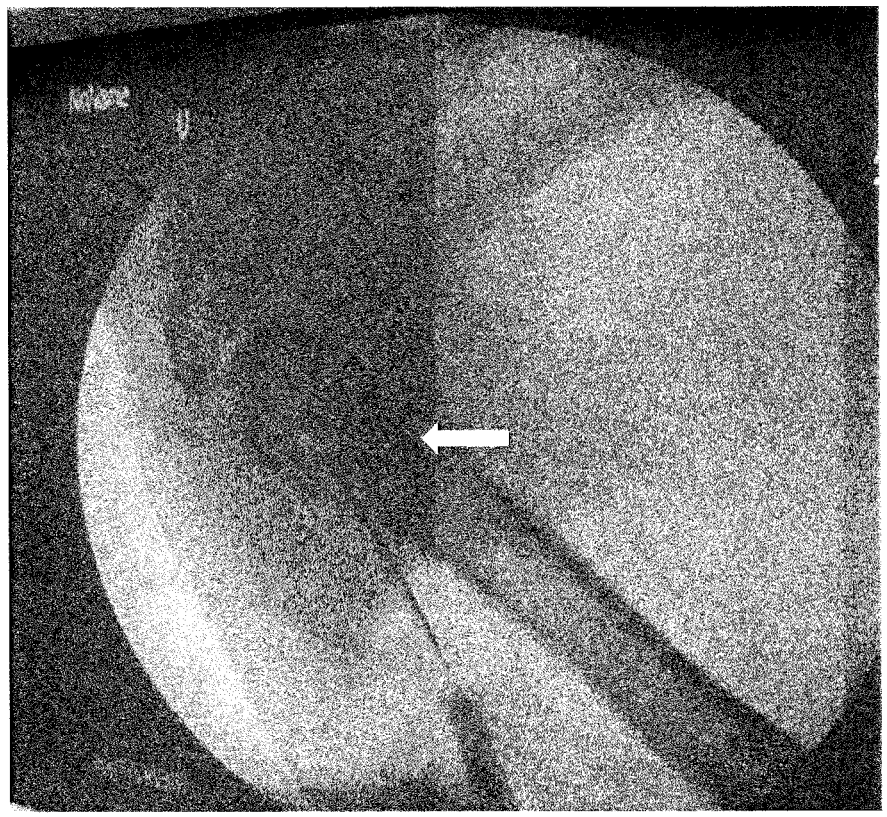
FIG. 35 shows percutaneous injection via a needle of the ITA2 cement adhesive into a proximal humerus fracture according to an example embodiment of the disclosure.

One right-sided adult upper extremity cadaveric specimen was used. A similar procedure as that described above was used to create a fracture through a stab incision on the lateral aspect of the shoulder. 10 cc of the ITA2 cement adhesive was injected into the fracture site (FIG. 35). The ITA2 cement adhesive is indicated by the arrow in FIG. 35. Traction was maintained for 5 minutes then the adhesive was allowed to set for 1 hour. Soft tissue dissection as described above was performed.

III. Results and Discussion

Both the wrist and the proximal humerus fractures were easily accessible through the percutaneous stab incision. The ITA2 cement was readily injected through the 16 gauge needle and could be observed flowing into the fracture site using fluoroscopy. The wrist and shoulder were put through a range of motion and the fracture site appeared stable on fluoroscopy. Soft tissue dissection revealed that the BBA was largely contained in the fracture site with little extravagation into the soft tissues.

IV. Summary

This study investigated a surgical technique for percutaneous upper extremity fracture fixation using the bioglass-containing adhesive ITA2. Three intact upper extremity cadaveric specimens with undisturbed soft tissues were obtained. Two were used to model a wrist fracture, and the third to model a proximal humerus fracture. Fractures were produced using a small osteotome in a percutaneous fashion. The ITA2 cement adhesive was delivered to the fracture site percutaneously using a 16 gauge needle under bi-planar fluoroscopic guidance. After setting of the adhesive, the specimens were dissected to qualitatively assess adhesive delivery and placement. The adhesive could readily be delivered through the 16 gauge needle with an appropriate amount of pressure applied to the syringe. The adhesive could be seen on the fluoroscope to flow into the fracture site with minimal extravagation into the surrounding soft tissues. Successful bonding of the fracture fragments was observed. Based on the results from these cadaveric models, percutaneous delivery of ITA2 cement adhesive into a fracture of the distal radius and/or proximal humerus may be a useful fracture fixation technique.

Example 5: Full Arm Cadaver Test for Injectability

Figure 36:
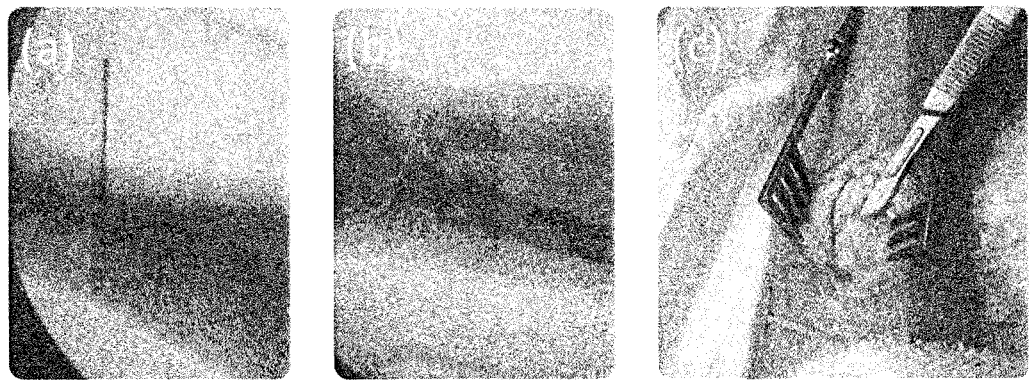
FIG. 36 shows wrist fixation with bioadhesive ITA2 according to example embodiments of the disclosure. In particular, the image labelled (a) shows the needle inserted percutaneously; the image labelled (b) shows the bioadhesive ITA2 injected into the fracture site; and the image labelled (c) shows the fixation site viewed to confirm the rigidity of the bioadhesive ITA2.

Pre-clinical cadaveric trials were conducted on full arm human cadavers at the clinical skills lab in Mt Sinai Hospital. The test showed that the injectable cement ITA2 (prepared as described above in Example 4) was injectable, could be monitored by x-ray guidance and adhere to bone, but not soft tissue (FIG. 36), showing needle inserted percutaneously (image labelled a), the bioadhesive ITA2 injected into the fracture site (image labelled b) and the fixation site viewed to confirm the rigidity of the fracture (image labelled c).

Example 6: Biomechanical Testing of Cadaveric Bones

Tests were conducted to investigate the structural integrity of the bioadhesives for sternal closure and the repair of distal radial fractures.

I. Sternal Tests

Figure 37:
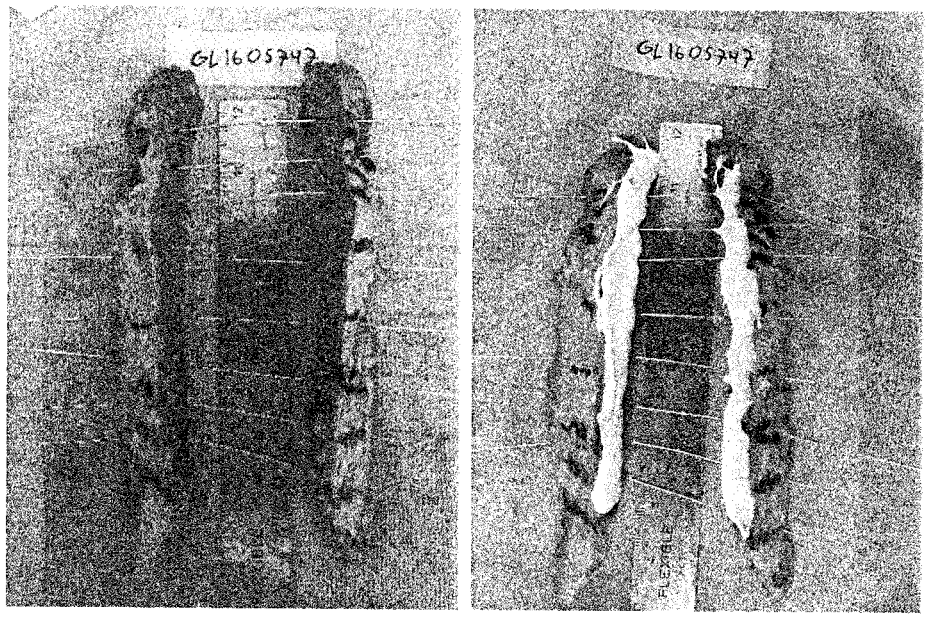
FIG. 37 shows images of a sternum wired using the gold standard technique according to a comparative example of the disclosure (left hand image) and a sternum with bioadhesive TA2 applied and wired according to an example embodiment of the disclosure.

An aim of the sternal tests was to investigate the use of the bioadhesives to reduce or eliminate the relative movement between the two halves of a sternum following a sternotomy. Human cadaveric sterna were first cut in half lengthwise, and put into two comparative groups (matched for average age and sex). For group 1, the sterna were joined using a traditional 'gold standard' wiring technique (FIG. 37, left hand image). For group 2, bioadhesive TA2 (prepared generally as described hereinabove in Example 2 but using a weight ratio of 1:1.5 between the glass and PAA/water such that 10 g of TA2 glass was mixed with 7.5 g of PAA35 and 7.5 mL of DI water) was first applied, and then the sterna were wired as in group 1 (FIG. 37, right hand image). The cement used in this Example had a working time of 4.20 minutes and a setting time of 53.10 minutes, each of which is longer for the TA2 cement prepared with the weight ratio of 1:1 between the glass and PAA/water. PAA35 has a $M_w$ of 50,000 which is lower than the $M_w$ of PAA used in Example 2.

Both sets of sterna were then tested cyclically (force control) in tension using a specially designed jig at forces between 100-500N, while both the force, and the displacement across the sterna were measured. The sternal jig was made up of three main components: U-shaped brackets to secure the sternum, exterior brackets to secure the jig to an Instron and hanger bolts coupled with metal plates to secure the extensometer across the two halves of the sternum. First, using a potting agent, the two halves of the sternum were set into the U-shaped brackets. Care was taken to prevent the bond line from coming in contact with the potting agent. Screws were then fastened through the top of the brackets holding both potting agent and the sternum to eliminate any movement or slippage within the jig. The U-shaped brackets were then inserted into the exterior brackets and securely fastened with flat head screws. The exterior brackets were attached to the Instron machine using swivel joints to allow for the normal to be found under tensile force. Next, two hanger bolts were drilled into each half of the sternum to attach two metal plates across each half. The extensometer was then clipped onto these metal plates to effectively measure displacement directly across the bond line.

Figure 38:
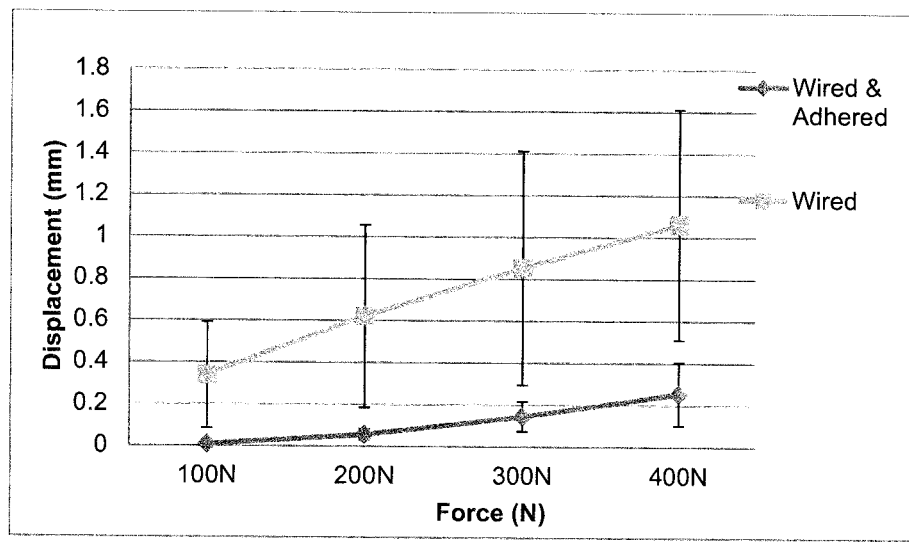
FIG. 38 is a plot showing displacement (mm) across sterna halves as a function of force (N) at various tensile cyclic loads for a sternum wired using the gold standard technique according to a comparative example of the disclosure compared to a sternum with bioadhesive TA2 applied and wired according to an example embodiment of the disclosure.

As seen in FIG. 38, the bioadhesive-augmented group 2 sterna experienced almost an order of magnitude lower displacement at physiological coughing loads than the gold standard wiring technique. The reduction displacement when using TA2 was 97% at 100N and 62% at 400N. Therefore, there is potential to reduce post-operative pain (based, for example, on less displacement as observed in this cadaveric model) and deep sternal wound infection (DSWI; based, for example, on the antimicrobial analysis results described in Examples 1 and 2) associated with relative displacement of the sectioned sternum by use of the bioadhesives such as TA2.

II. Tests of Injectable Cement on Radii

Figure 39:
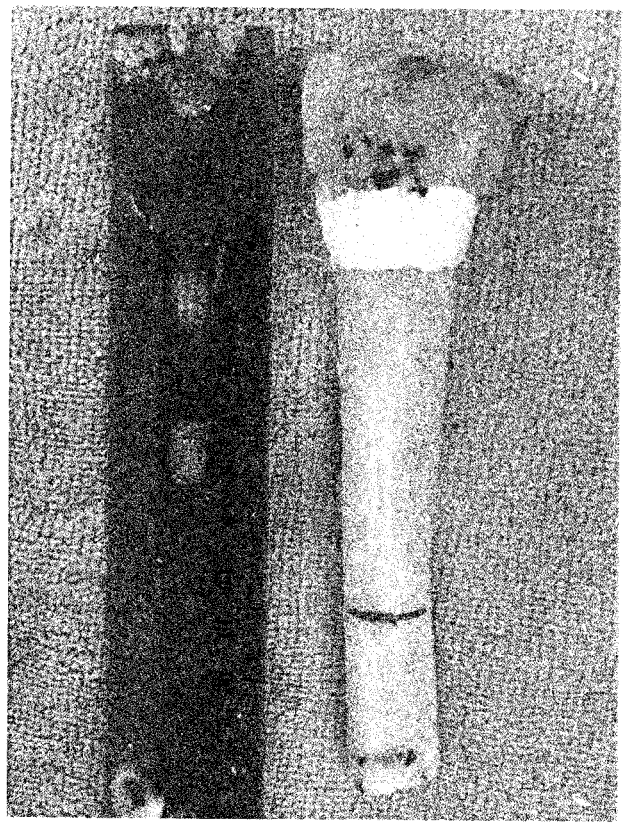
FIG. 39 shows a radius with simulated fracture filled with bioadhesive ITA2 according to an example embodiment of the disclosure.

An aim of the radial tests was to investigate the use of the bioadhesives to treat distal fractures of the radius. A number of paired (left and right arm radii) human cadaveric samples were obtained. For one of the bones in each pair, a 1 cm deep (nearly through the thickness) wedge shaped piece of bone was removed, thus simulating a comminuted fracture. The wedge-shaped gap was filled with bioadhesive ITA2 (prepared generally as described hereinabove in Example 4 but using a weight ratio of 1:2.33 between the glass and PAA/water such that 3 g of TA2 glass was mixed with 3 g of PAA35 and 4 mL of DI water) (FIG. 39). The other bone making up the pair was left intact. The cement used in this Example had a working time of 19.44 minutes and a setting time of 164.30 minutes, each of which is longer for the ITA2 cement prepared with the weight ratio of 1:1 between the glass and PAA/water.

The bones were all tested in compression up to failure using a specially designed setup. The radial jig was made up of two aluminum cups meant to securely hold the radius in place under compressive force. All radii were cut transversely 14 mm from the radial styloid. First, a hanger bolt was fastened into the bottom cup and then inserted into the shaft of the radius from where the transverse cut was made. Next, using 3D printed aligners, the position of the top cup was found. An alignment pin was then sent in from the top cup to determine the position of the radius. The alignment pin was to always rest on the scaphoid facet. Potting agent was then poured into both halves of the jig to secure the alignment and position of the radius. Care was taken to ensure the potting agent did not come in contact with the defect and that its level was always 3.5 mm from where the transverse cut was made. Two screws were then inserted, perpendicular to each other, into both cups to secure the potting agent and prevent any slippage within the jig. The bottom half of the jig was directly pinned to an Instron allowing for zero degrees of freedom. The top half of the jig was not directly fastened to the Instron. Instead, it included a circular indent. By securing a large pin with a rounded bottom to the top of the Instron machine, once in contact with the circular indent of the top cup, 360 degrees of rotation (three degrees of freedom) were allowed ensuring a normal compressive force always being applied.

It was found that the strength of the fractured bone construct with bioadhesive was, on average, about 75% of the strength of the intact (no fracture whatsoever) bone. These results clearly illustrate that bioadhesives such as TA2 may, for example, be useful for wrist fracture applications.

Example 7: Testing of TA2 Cement in In Vivo Ovine Model

Figure 40:
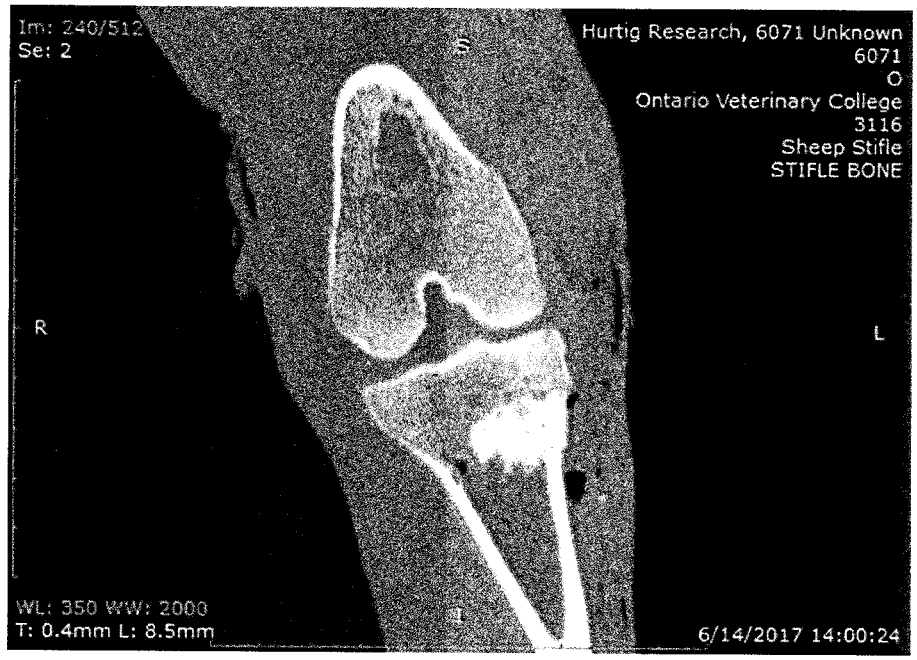
FIG. 40 shows a critical defect created in the proximal tibia of a sheep filled with injectable ITA2 adhesive according to an example embodiment of the disclosure.

ITA2 cements were prepared as described hereinabove in Example 6, part II and were injected in an in vivo sheep model. The surgical sites included the distal femur and proximal tibia. Both non-critical and critical defects are being tested. For 4 of the experiments, non-critical defects (the bone would not be predicted to break in the presence of a non-critical defect) which were 6 mm holes made in the distal femur and proximal tibia were created and filled with ITA2 bone adhesive. One experiment using a larger, critical defect (left untreated, the bone is likely to break in the presence of a critical defect) in the proximal tibia filled with injectable ITA2 adhesive is also underway (FIG. 40). Non-critical defects were tested, for example, to see how well the sheep could walk subsequent to the defect being filled with the ITA2 cement. Critical defects were tested, for example, to determine how well the bone would heal subsequent to being filled with the ITA2 cement. No complications have been encountered in the operative and early post-operative period, and the animals are doing well. Results to date show stability of the adhesive implant and positive bone response with early signs of new bone formation near the adhesive.

While the present disclosure has been described with reference to what are presently considered to be the preferred examples, it is to be understood that the application is not limited to the examples described herein. To the contrary, the present disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

FULL CITATIONS FOR DOCUMENTS REFERRED TO IN THE SPECIFICATION

[1] A. Hoppe, N. S. Guldal, A. R. Boccaccini, A review of the biological response to ionic dissolution products from bioactive glasses and glass-ceramics., Biomaterials. 32 (2011) 2757-2774. doi:10.1016/j.biomaterials.2011.01.004.

[2] J. R. Jones, Review of bioactive glass: from Hench to hybrids., Acta Biomater. 9 (2013) 4457-86. doi:10.1016/j.actbio.2012.08.023.

[3] W. H. Zachariasen, The atomic arrangement in glass., J. Am. Chem. Soc. 54 (1932) 3841-3851. doi:10.1021/ja01349a 006.

[4] S. Grabowsky, M. F. Hesse, C. Paulmann, P. Luger, J. Beckmann, How to Make the Ionic Si—O Bond More Covalent and the Si—O—Si Linkage a Better Acceptor for Hydrogen Bonding, Inorg. Chem. 48 (2009) 4384-4393. doi:10.1021/ic900074r.

[5] S.-P. Szu, L. C. Klein, M. Greenblatt, Effect of precursors on the structure of phosphosilicate gels: 29Si and 31P MAS-NMR study, J. Non. Cryst. Solids. 143 (1992) 21-30. doi:10.1016/S0022-3093(05)80548-4.

[6] A. M. F. Alhalawani, M. R. Towler, The effect of $ZnO*Ta_2O_5$ substitution on the structural and thermal properties of $SiO2-ZnO—SrO—CaO—P2O5$ glasses, Mater. Charact. 114 (2016) 218-224. doi:10.1016/j.matchar.2016.03.004.

[7] R. T. Sanderson, An Interpretation of Bond Lengths and a Classification of Bonds, Science. 114 (1951) 670-672. doi:10.1126/science. 114.2973.670.

[8] H. Darwish, S. Ibrahim, M. M. Gomaa, Electrical and physical properties of $Na_2O—CaO—MgO—SiO2$ glass doped with NdF3, J. Mater. Sci. Mater. Electron. 24 (2012) 1028-1036. doi: 10.1007/s10854-012-0873-8.

[9] M. Eigen, Structural Chemistry of Glasses, Elsevier, 2002. doi:10.1016/B978-008043958-7/50030-3.

[10] G. Calas, L. Cormier, L. Galoisy, P. Jollivet, Structure-property relationships in multicomponent oxide glasses, Comptes Rendus Chim. 5 (2002) 831-843. doi:10.1016/S1631-0748(02)01459-5.

[11] V. K. Balla, S. Bodhak, S. Bose, A. Bandyopadhyay, Porous tantalum structures for bone implants: fabrication, mechanical and in vitro biological properties., Acta Biomater. 6 (2010) 3349-59. doi:10.1016/j.actbio.2010.01.046.

[12] K. B. Sagomonyants, M. Hakim-Zargar, A. Jhaveri, M. S. Aronow, G. Gronowicz, Porous tantalum stimulates the proliferation and osteogenesis of osteoblasts from elderly female patients, J. Orthop. Res. 29 (2011) 609-616. doi: 10.1002/jor.21251.

[13] V. K. Balla, S. Bose, N. M. Davies, A. Bandyopadhyay, Tantalum—A bioactive metal for implants, JOM. 62 (2010) 61-64. doi:10.1007/s11837-010-0110-y.

[14] T. Miyaza, H.-M. Kim, T. Kokubo, C. Ohtsuki, H. Kato, T. Nakamura, Mechanism of bonelike apatite formation on bioactive tantalum metal in a simulated body fluid., Biomaterials. 23 (2002) 827-832.

[15] Y.-Y. Chang, H.-L. Huang, H.-J. Chen, C.-H. Lai, C.-Y. Wen, Antibacterial properties and cytocompatibility of tantalum oxide coatings, Surf. Coatings Technol. 259 (2014) 193-198. doi:10.1016/j.surfcoat.2014.03.061.

[16] M. Roy, V. K. Balla, S. Bose, A. Bandyopadhyay, Comparison of Tantalum and Hydroxyapatite Coatings on Titanium for Applications in Load Bearing Implants, Adv. Eng. Mater. 12 (2010) B637-B641. doi:10.1002/adem.201080017.

[17] J. Black, Biologic performance of tantalum, Clin. Mater. 16 (1994) 167-173. doi:10.1016/0267-6605(94)90113-9.

[18] A. D. Wilson, B. E. Kent, The Glass-Ionomer Cement, a New Translucent Dental Filling Material, Appl. Chem. Biotechnol. 21 (1971)313.

[19] G. Lewis, M. R. Towler, D. Boyd, M. J. German, A. W. Wren, O. M. Clarkin, et al., Evaluation of two novel aluminum-free, zinc-based glass polyalkenoate cements as alternatives to PMMA bone cement for use in vertebroplasty and balloon kyphoplasty., J. Mater. Sci. Mater. Med. 21 (2010) 59-66.

[20] J. W. Nicholson, "Adhesive dental materials—A review," Int. J. Adhes. Adhes., 18 [4] 229-236 (1998).

[21] N. Zainuddin, N. Karpukhina, R. G. Hill, R. V Law, A long-term study on the setting reaction of glass ionomer cements by (27)Al MAS-NMR spectroscopy., Dent. Mater. 25 (2009) 290-5.

[22] J. W. Nicholson, "Chemistry of glass-ionomer cements: a review," Biomaterials, 19 485-494 (1998).

[23] E. A. Wasson, J. W. Nicholson, New aspects of the setting of glass-ionomer cements, J Dent Res. 72 (1993) 481-483.

[24] Alhalawani Adel M F, C. D. J, B. Daniel, and T. M. R, The role of poly(acrylic acid) in conventional glass polyalkenoate cements: a review, J. Polym. Eng., 0 (2015).

[25] A. O. Akinmade and J. W. Nicholson, "Glass-ionomer cements as adhesives," J Mater Sci Mater Med, 4 95-101 (1993).

[26] J. F. McCabe, D. Watts, H. J. Wilson, and H. V Worthington, "An investigation of test-house variability in the mechanical testing of dental materials," J Dent, 18 90-97 (1990).

[27] D. Boyd, M. R. Towler, A. W. Wren, O. M. Clarkin, and D. A. Tanner, "TEM analysis of apatite surface layers observed on zinc based glass polyalkenoate cements," J. Mater. Sci., 43 [3] 1170-1173 (2008).

[28] M. Navarro, A. Michiardi, O. Castano, and J. A. Planell, "Biomaterials in orthopaedics," J. R. Soc. Interface, 5 [27] 1137-1158 (2008).

[29] D. Boyd, O. M. Clarkin, A. W. Wren, and M. R. Towler, "Zinc-based glass polyalkenoate cements with improved setting times and mechanical properties," Acta Biomater., 4 [2] 425-431 (2008).

[30] T. M. Eidem, A. Coughlan, M. R. Towler, P. M. Dunman, and A. W. Wren, "Drug-eluting cements for hard tissue repair: a comparative study using vancomycin and RNPA1000 to inhibit growth of Staphylococcus aureus.," J. Biomater. Appl., 28 [8] 1235-1246 (2014).

[31] G. Lewis, M. R. Towler, D. Boyd, M. J. German, A. W. Wren, O. M. Clarkin, and A. Yates, "Evaluation of two novel aluminum-free, zinc-based glass polyalkenoate cements as alternatives to PMMA bone cement for use in vertebroplasty and balloon kyphoplasty.," J. Mater. Sci. Mater. Med., 21 [1] 59-66 (2010).

[32] O. M. Clarkin, D. Boyd, S. Madigan, and M. R. Towler, "Comparison of an experimental bone cement with a commercial control, Hydroset.," J. Mater. Sci. Mater. Med., 20 [7] 1563-1570 (2009).

[33] A. M. Alhalawani and M. R. Towler, "A review of sternal closure techniques.," J. Biomater. Appl., 28 [4] 483-97 (2013).

[34] A. Alhalawani, D. Curran, B. Pingguan-Murphy, D. Boyd, and M. Towler, "A Novel Glass Polyalkenoate Cement for Fixation and Stabilisation of the Ribcage, Post Sternotomy Surgery: An ex-Vivo Study," J. Funct. Biomater., 4 [4] 329-357 (2013).

[35] M. Darling and R. Hill, "Novel polyalkenoate (glassionomer) dental cements based on zinc silicate glasses," Biomaterials, 15 [4] 299-306 (1994).

[36] M. R. Towler, S. Kenny, D. Boyd, T. Pembroke, M. Buggy, and R. G. Hill, "Zinc ion release from novel hard tissue biomaterials," Biomed Mater Eng., 14 565-572 (2004).

[37] R. B. Saper and R. Rash, "Zinc: an essential micronutrient.," Am. Fam. Physician, 79 [9] 768-772 (2009).

[38] P. J. Marie, P. Ammann, G. Boivin, and C. Rey, "Mechanisms of action and therapeutic potential of strontium in bone.," Calcif. Tissue Int., 69 [3] 121-129 (2001).

[39] V. K. Balla, S. Bodhak, S. Bose, and A. Bandyopadhyay, "Porous tantalum structures for bone implants: fabrication, mechanical and in vitro biological properties.," Acta Biomater., 6 [8] 3349-59 (2010).

[40] K. B. Sagomonyants, M. Hakim-Zargar, A. Jhaveri, M. S. Aronow, and G. Gronowicz, "Porous tantalum stimulates the proliferation and osteogenesis of osteoblasts from elderly female patients," J. Orthop. Res., 29 [4] 609-616 (2011).

[41] V. K. Balla, S. Bose, N. M. Davies, and A. Bandyopadhyay, "Tantalum—A bioactive metal for implants," JOM, 62 [7] 61-64 (2010).

[42] C. Persson, L. Guandalini, F. Baruffaldi, L. Pierotti, and M. Baleani, "Radiopacity of tantalum-loaded acrylic bone cement.," Proc. Inst. Mech. Eng. H., 220 [7] 787-791 (2006).

[43] O. Friberg, L. G. Dahlin, B. Sbderquist, J. Kallman, and R. Svedjeholm, "Influence of more than six sternal fixation wires on the incidence of deep sternal wound infection," Thorac. Cardiovasc. Surg., 54 [7] 468-473 (2006).

[44] D. J. Cohen and L. V Griffin, "A biomechanical comparison of three sternotomy closure techniques.," Ann. Thorac. Surg., 73 [2] 563-568 (2002).

[45] C. Schimmer, W. Reents, S. Berneder, P. Eigel, O. Sezer, H. Scheld, K. Sahraoui, B. Gansera, et al., "Prevention of sternal dehiscence and infection in high-risk patients: a prospective randomized multicenter trial.," Ann. Thorac. Surg., 86 [6] 1897-904 (2008).

[46] L. F. Lopez Almodovar, G. Bustos, P. Lima, A. Canas, I. Paredes, and J. A. Buendia, "Transverse plate fixation of sternum: a new sternal-sparing technique.," Ann. Thorac. Surg., 86 [3] 1016-1017 (2008).

[47] M. Ford, J. Brunelli, D. Song, P. Costello, R. M. Dunn, and K. Billiar, Design of a screw-plate system to minimize loosening in sternal fixation, Bioeng. Conf. (NEBEC), 2011 IEEE 37th Annu. Northeast, 1-2 (2011).

[48] P. W. Fedak, E. Kolb, G. Borsato, D. E. Frohlich, A. Kasatkin, K. Narine, N. Akkarapaka, and K. M. King, "Kryptonite bone cement prevents pathologic sternal displacement," Ann Thorac Surg, 90 979-985 (2010).

[49] P. W. M. Fedak and A. Kasatkin, "Enhancing sternal closure using Kryptonite bone adhesive: technical report.," Surg. Innov., 18 [4] NP8-11 (2011).

[50] M. Holland, K. King, and P. Fedak, "Sternal closure with kryptonite—an innovative approach to a lingering pain in the chest," Can J Cardiol, 26 269-282 (2010).

[51] (a) Lopez Almodovar et al., 2008; (b) C. Schimmer, M. Ozkur, B. Sinha, J. Hain, A. Gorski, B. Hager, and R. Leyh, "Gentamicin-collagen sponge reduces sternal wound complications after heart surgery: a controlled, prospectively randomized, double-blind study.," J. Thorac. Cardiovasc. Surg., 143 [1] 194-200 (2012).

[52] M. N. Mavros, P. K. Mitsikostas, V. G. Alexiou, G. Peppas, and M. E. Falagas, "Gentamicin collagen sponges for the prevention of sternal wound infection: a meta-analysis of randomized controlled trials.," J. Thorac. Cardiovasc. Surg., 144 [5] 1235-1240 (2012).

[53] S. Jolly, B. Flom, and C. Dyke, "Cabled butterfly closure: a novel technique for sternal closure.," Ann. Thorac. Surg., 94 [4] 1359-1361 (2012).

[54] A. W. Wren, A. Coughlan, L. Placek, and M. R. Towler, "Gallium containing glass polyalkenoate anti-cancerous bone cements: Glass characterization and physical properties," J. Mater. Sci. Mater. Med., 23 [8] 1823-1833 (2012).

[55] A. M. F. Alhalawani, L. Placek, A. W. Wren, D. J. Curran, D. Boyd, and M. R. Towler, "Influence of gallium on the surface properties of zinc based glass polyalkenoate cements," Mater. Chem. Phys., 147 [3] 360-364 (2014).

[56] C. Cooper, G. Campion, L. J. Melton, Hip fractures in the elderly: A world-wide projection, Osteoporos. Int. 2 (1992) 285-289.

[57] S. R. Cummings, J. L. Kelsey, M. C. Nevitt, K. J. O'dowd, Epidemiology of osteoporosis and osteoporotic fractures, Epidemiol. Rev. 7 (1985) 178-208.

[58] T. A. Abbott, B. J. Lawrence, S. Wallach, Osteoporosis: the need for comprehensive treatment guidelines, Clin. Ther. 18 (1996) 127-149.

[59] B. L. Riggs, L. J. Melton, The Prevention and Treatment of Osteoporosis, N. Engl. J. Med. 327 (1992) 620-627.

[60] D. Ring, J. B. Jupiter, Treatment of osteoporotic distal radius fractures, Osteoporos. Int. 16 (2005) S80-S84.

[61] D. P. Green, Pins and plaster treatment of comminuted fractures of the distal end of the radius, J. Bone & Jt. Surg. 57 (1975) 304 LP-310. http://jbjs.org/content/57/3/304.abstract.

[62] S. A. Earnshaw, A. Aladin, S. Surendran, C. G. Moran, Closed Reduction of Colles Fractures: Comparison of Manual Manipulation and Finger-Trap Traction, J. Bone & Jt. Surg. 84 (2002) 354 LP-358. http://jbjs.org/content/84/3/354.abstract.

[63] a) F. Fitoussi, W. Y. Ip, S. P. Chow, Treatment of displaced intra-articular fractures of the distal end of the radius with plates, J Bone Jt. Surg. 79A (1997); b) M. G. Jakubietz, J. G. Gruenert, R. G. Jakubietz, The use of beta-tricalcium phosphate bone graft substitute in dorsally plated, comminuted distal radius fractures, J. Orthop. Surg. Res. 6 (2011) 24; c) H. Kapoor, A. Agarwal, B. K. Dhaon, Displaced intraarticular fractures of distal radius: a comparative evaluation of results following closed reduction, external fixation and open reduction with internal fixation, Injury. 31 (2000); d) H. Sakano, T. Koshino, T. Saito, Treatment of the unstable radius fracture with external fixation and a hydroxyapatite spacer, J Hand Surg. 26A (2001); e) J. L. Orbay, D. L. Fernandez, Volar fixed-angle plate fixation for unstable distal radius fractures in the elderly patient., J. Hand Surg. Am. 29 (2004) 96-102.

[64] N. Hidaka, Y. Yamano, Y. Kadoya, N. Nishimura, Calcium phosphate bone cement for treatment of distal radius fractures: a preliminary report, J Orthop Sci. 7 (2002).

[65] T. Kosuge, Y. Benino, V. Dimitrov, R. Sato, T. Komatsu, Thermal stability and heat capacity changes at the glass transition in $K_2O$—WO3-TeO2 glasses, J. Non. Cryst. Solids. 242 (1998) 154-164. doi:10.1016/S0022-3093(98)00800-X.

[66] A. Stamboulis, R. V Law, R. G. Hill, Characterisation of commercial ionomer glasses using magic angle nuclear magnetic resonance (MAS-NMR)., Biomaterials. 25 (2004) 3907-3913. doi:10.1016/j.biomaterials.2003.10.074.

[67] D. S. Brauer, C. Rüssel, J. Kraft, Solubility of glasses in the system P2O5-CaO—MgO—Na2O—TiO2: Experimental and modeling using artificial neural networks, J. Non. Cryst. Solids. 353 (2007) 263-270. doi:10.1016/j.jnoncrysol.2006.12.005.

[68] N. Y. Mikhailenko, E. E. Stroganova, N. V Buchilin, Solubility of Calcium Phosphate Glasses and Glass Ceramic Materials in Water and Physiological Media, Glas. Ceram. 70 (2013) 158-163. doi:10.1007/s10717-013-9531-8.

[69] G. Mohandas, N. Oskolkov, M. T. McMahon, P. Walczak, M. Janowski, Porous tantalum and tantalum oxide nanoparticles for regenerative medicine., Acta Neurobiol. Exp. (Wars). 74 (2014) 188-196.

[70] J. A. Williams, R. W. Billington, and G. J. Pearson, "The effect of the disc support system on biaxial tensile strength of a glass ionomer cement.," Dent. Mater., 18 [5] 376-379 (2002).

[71] ISO 9917-1:2007, Dentistry—Water-based cements—Part 1: Powder/liquid acid-base cements. 2007.

[72] K. E. Kuettner, B. U. Pauli, G. Gall, V. A. Memoli, and R. K. Schenk, "Synthesis of cartilage matrix by mammalian chondrocytes in vitro. I. Isolation, culture characteristics, and morphology," J. Cell Biol., 93 [3] 743-750 (1982).

[73] A. W. Wren, A. Kidari, N. M. Cummins, and M. R. Towler, "A spectroscopic investigation into the setting and mechanical properties of titanium containing glass polyalkenoate cements.," J. Mater. Sci. Mater. Med., 21 [8] 2355-2364 (2010).

[74] S. K. Tomlinson, O. R. Ghita, R. M. Hooper, and K. E. Evans, "Investigation of the dual setting mechanism of a novel dental cement using infrared spectroscopy," Vib. Spectrosc., 45 [1] 10-17 (2007).

[75] Y. Zhang, F. Zhu, J. Zhang, and L. Xia, "Converting Layered Zinc Acetate Nanobelts to One-dimensional Structured ZnO Nanoparticle Aggregates and their Photocatalytic Activity," Nanoscale Res. Lett., 3 [6] 201-204 (2008).

[76] S. Matsuya, Y. Matsuya, and M. Ohta, "Structure of bioactive glass and its application to glass ionomer cement.," Dent. Mater. J., 18 [2] 155-166 (1999).

[77] J. Rajamathi, S. Britto, and M. Rajamathi, "Synthesis and anion exchange reactions of a layered copper-zinc hydroxy double salt, $Cu1.6Zn0.4(OH)3(OAc).H2O$," J. Chem. Sci., 117 [6] 629-633 (2005).

[78] S. Matsuya, T. Maeda, and M. Ohta, "IR and NMR Analyses of Hardening and Maturation of Glass-ionomer Cement," *J Dent Res*, 75 1920-1927 (1996).

[79] M. Driessen, T. Miller, and V. Grassian, "Photocatalytic oxidation of trichloroethylene on zinc oxide: characterization of surface-bound and gas-phase products and intermediates with FT-IR spectroscopy," *J. Mol. Catal. A Chem.*, 131 [1-3] 149-156 (1998).

[80] E. A. Wasson and J. W. Nicholson, "Study on the setting chemistry of glass-ionomer cements," *Clin. Mater.*, 7 289-293 (1991).

[81] A. W. Wren, A. Coughlan, L. Placek, and M. R. Towler, "Gallium containing glass polyalkenoate anti-cancerous bone cement: Glass characterization and physical properties," *J Mater Sci Mater Med*, 23 1823-1833 (2012).

[82] A. W. Wren, A. Coughlan, M. M. Hall, M. J. German, and M. R. Towler, "Comparison of a SiO2-CaO—ZnO—SrO glass polyalkenoate cement to commercial dental materials: ion release, biocompatibility and antibacterial properties," *J. Mater. Sci. Mater. Med.*, 24 [9] 2255-2264 (2013).

[83] L. Grech, B. Mallia, and J. Camilleri, "Investigation of the physical properties of tricalcium silicate cement-based root-end filling materials.," *Dent. Mater.*, 29 [2] e20-8 (2013).

[84] G. M. de Pietro, C. Pereira, R. R. Gongalves, S. J. L. Ribeiro, C. D. Freschi, F. C. Cassanjes, and G. Poirier, "Thermal, Structural, and Crystallization Properties of New Tantalum Alkali-Germanate Glasses," *J. Am. Ceram. Soc.*, 98 [7] 2086-2093 (2015).

[85] A. Coughlan, K. Scanlon, B. P. Mahon, and M. R. Towler, "Zinc and silver glass polyalkenoate cements: an evaluation of their antibacterial nature," *Biomed Mater Eng.*, 20 99-106 (2010).

[86] Y. H. An and R. J. Friedman, "Concise review of mechanisms of bacterial adhesion to biomaterial surfaces.," *J. Biomed. Mater. Res.*, 43 [3] 338-348 (1998).

[87] A. W. Wren, A. Coughlan, F. R. Laffir, and M. R. Towler, "Comparison of a SiO2-CaO—ZnO—SrO glass polyalkenoate cement to commercial dental materials: glass structure and physical properties.", *J Mater Sci Mater Med*, 24 271-280 (2013).

[88] A. Guida, M. R. Towler, and J. G. Wall, "Preliminary work on the antibacterial effect of strontium in glass ionomer cements," *J Mater Sci Lett*, 22 1401-1403 (2003).

[89] V. K. Balla, S. Bodhak, S. Bose, and A. Bandyopadhyay, "Porous tantalum structures for bone implants: fabrication, mechanical and in vitro biological properties.," *Acta Biomater.*, 6 [8] 3349-59 (2010).

[90] Y.-Y. Chang, H.-L. Huang, H.-J. Chen, C.-H. Lai, and C.-Y. Wen, "Antibacterial properties and cytocompatibility of tantalum oxide coatings," *Surf. Coatings Technol.*, 259 193-198 (2014).

[91] M. Roy, V. K. Balla, S. Bose, and A. Bandyopadhyay, "Comparison of Tantalum and Hydroxyapatite Coatings on Titanium for Applications in Load Bearing Implants," *Adv. Eng. Mater.*, 12 [11] B637-B641 (2010).

[92] J. J. Harrison, M. *Rabiei*, R. J. Turner, E. A. Badry, K. M. Sproule, and H. Ceri, "Metal resistance in *Candida* biofilms.," *FEMS Microbiol. Ecol.*, 55 [3] 479-491 (2006).

[93] M. R. Bruins, S. Kapil, and F. W. Oehme, "Microbial resistance to metals in the environment.," *Ecotoxicol. Environ. Saf.*, 45 [3] 198-207 (2000).

[94] O. E. Sorensen, J. B. Cowland, K. Theilgaard-Monch, L. Liu, T. Ganz, and N. Borregaard, "Wound healing and expression of antimicrobial peptides/polypeptides in human keratinocytes, a consequence of common growth factors.," *J. Immunol.*, 170 [11] 5583-5589 (2003).

[95] D. C. Smith, "Development of glass-ionomer cement systems.," *Biomaterials*, 19 [6] 467-478 (1998).

[96] A. Hoppe, N. S. Guldal, and A. R. Boccaccini, "A review of the biological response to ionic dissolution products from bioactive glasses and glass-ceramics.," *Biomaterials*, 32 [11] 2757-2774 (2011).

[97] M. Roy, V. K. Balla, S. Bose, and A. Bandyopadhyay, "Comparison of Tantalum and Hydroxyapatite Coatings on Titanium for Applications in Load Bearing Implants," *Adv. Eng. Mater.*, 12 [11] B637-B641 (2010).

[98] V. K. Balla, S. Bodhak, S. Bose, and A. Bandyopadhyay, "Porous tantalum structures for bone implants: fabrication, mechanical and in vitro biological properties.," *Acta Biomater.*, 6 [8] 3349-59 (2010).

[99] M. Roy, V. K. Balla, S. Bose, and A. Bandyopadhyay, "Comparison of Tantalum and Hydroxyapatite Coatings on Titanium for Applications in Load Bearing Implants," *Adv. Eng. Mater.*, 12 [11] B637-B641 (2010).

[100] N. Moritz, E. Vedel, H. Ylanen, M. Jokinen, M. Hupa, and A. Yli-Urpo, "Characterisation of bioactive glass coatings on titanium substrates produced using a CO2 laser.," *J. Mater. Sci. Mater. Med.*, 15 [7] 787-794 (2004).

The invention claimed is:

1. A glass comprising silicon dioxide ($SiO_2$), zinc oxide (ZnO), calcium oxide (CaO), strontium oxide (SrO), phosphorous pentoxide ($P_2O_5$) and a transition metal pentoxide selected from tantalum pentoxide ($Ta_2O_5$), niobium pentoxide ($Nb_2O_5$) and mixtures thereof, wherein the transition metal pentoxide is present in the glass in an amount of less than 2.0 mol %, wherein the $SiO_2$ is present in an amount of from about 35.0 mol % to about 60.0 mol %;

the ZnO is present in an amount of from about 25.0 mol % to about 40.0 mol %;

the CaO is present in an amount of from about 2.0 mol % to about 12.0 mol %;

the SrO is present in an amount of from about 5.0 mol % to about 15.0 mol %; and the $P_2O_5$ is present in an amount of from about 1.0 mol % to about 5.0 mol %.

2. The glass of claim 1, wherein the transition metal pentoxide is present in an amount of from about 0.2 mol % to about 0.5 mol %.

3. The glass of claim 2, wherein the ZnO is present in an amount of about 35.5 mol %; and the transition metal pentoxide is present in an amount of about 0.5 mol %.

4. The glass of claim 2, wherein the ZnO is present in an amount of about 35.8 mol %; and the transition metal pentoxide is present in an amount of about 0.2 mol %.

5. The glass of claim 2, wherein the transition metal pentoxide is tantalum pentoxide ($Ta_2O_5$).

6. A glass polyalkenoate cement prepared from mixing the glass as defined in claim 1 with an aqueous solution of a polyalkenoic acid.

7. The cement of claim 6, wherein the polyalkenoic acid is poly(acrylic acid).

8. The cement of claim 7, wherein the poly(acrylic acid) has a weight average molecular weight (Mw) of about 35,000 to about 250,000.

9. The cement of claim 6, wherein the glass is annealed prior to mixing with the aqueous solution of the polyalkenoic acid.

10. The cement of claim 6, wherein the ratio by weight of the glass:aqueous solution of polyalkenoic acid is from about 1:5 to about 1.5:1.

11. The cement of claim 6, wherein the ratio by weight of the polyalkenoic acid:water is about 1:1.

12. A method of repairing a bone or tooth in need thereof, the method comprising applying a cement as defined in claim 6 to a site of the bone or tooth in need-of repair.

13. The method of claim 12, wherein the method is for repairing a bone.

14. The method of claim 13, wherein the method is for fixation/closure and repair of a sternum that has been divided into at least two segments, and the method comprises applying the cement to the segments and closing the sternum.

15. The method of claim 14, wherein the method further comprises applying an additional technique for sternal closure.

16. The method of claim 14, wherein the fixation/closure and repair is of a sternum that has been divided during a median sternotomy.

17. The method of claim 14, wherein the method is for fixation, stabilization and/or repair of a fracture in a bone in the wrist, elbow, knee, shoulder, spine and/or hip and the method comprises applying the cement to the fracture and setting the cement to fixate, stabilize and/or repair the fracture.

18. The method of claim 17, wherein the applying comprises percutaneously injecting the cement into the fracture.

19. A kit for the preparation of a glass polyalkenoate cement, comprising:
   a glass as defined in claim 1;
   a polyalkenoic acid; and
   optionally instructions for mixing the glass with an aqueous solution of the polyalkenoic acid to prepare the cement.

* * * * *